(12) United States Patent
Ahluwalia et al.

(10) Patent No.: US 7,998,492 B2
(45) Date of Patent: Aug. 16, 2011

(54) METHODS AND PRODUCTS RELATED TO TREATMENT AND PREVENTION OF HEPATITIS C VIRUS INFECTION

(75) Inventors: Navneet K. Ahluwalia, Ottawa (CA); Susan M. Efler, Woodlawn (CA); Heather L. Davis, Dunrobin (CA); Jörg Vollmer, Düsseldorf (DE)

(73) Assignees: Coley Pharmaceutical Group, Inc., New York, NY (US); Coley Pharmaceutical GmbH, Lagenfeld (DE)

( * ) Notice: Subject to any disclaimer, the term of this patent is extended or adjusted under 35 U.S.C. 154(b) by 601 days.

(21) Appl. No.: 10/532,746

(22) PCT Filed: Oct. 29, 2003

(86) PCT No.: PCT/IB03/05520
§ 371 (c)(1),
(2), (4) Date: Sep. 9, 2005

(87) PCT Pub. No.: WO2004/039829
PCT Pub. Date: May 13, 2004

(65) Prior Publication Data
US 2006/0246035 A1    Nov. 2, 2006

Related U.S. Application Data

(60) Provisional application No. 60/421,987, filed on Oct. 29, 2002.

(51) Int. Cl.
| A61K 39/00 | (2006.01) |
| A61K 39/12 | (2006.01) |
| A61K 39/38 | (2006.01) |
| A61K 45/00 | (2006.01) |
| A61K 47/00 | (2006.01) |
| A61K 48/00 | (2006.01) |

(52) U.S. Cl. ............... 424/278.1; 424/184.1; 424/204.1; 514/44 R

(58) Field of Classification Search .................. None
See application file for complete search history.

(56) References Cited

U.S. PATENT DOCUMENTS

| 4,806,463 A | 2/1989 | Goodchild et al. |
| 5,004,810 A | 4/1991 | Draper |
| 5,023,243 A | 6/1991 | Tullis |
| 5,166,195 A | 11/1992 | Ecker |
| 5,248,670 A | 9/1993 | Draper et al. |
| 5,264,423 A | 11/1993 | Cohen et al. |
| 5,276,019 A | 1/1994 | Cohen et al. |
| 5,457,189 A | 10/1995 | Crooke et al. |
| 5,514,577 A | 5/1996 | Draper et al. |
| 5,565,354 A | 10/1996 | Ostberg et al. |
| 5,567,604 A | 10/1996 | Rando et al. |
| 5,576,302 A | 11/1996 | Cook et al. |
| 5,594,122 A | 1/1997 | Friesen |
| 5,658,891 A | 8/1997 | Draper et al. |
| 5,663,153 A | 9/1997 | Hutcherson et al. |
| 5,665,580 A | 9/1997 | Crooke et al. |
| 5,681,944 A | 10/1997 | Crooke et al. |
| 5,684,147 A | 11/1997 | Agrawal et al. |
| 5,723,335 A | 3/1998 | Hutcherson et al. |
| 5,728,518 A | 3/1998 | Carmichael |
| 5,780,448 A | 7/1998 | Davis |
| 5,817,637 A | 10/1998 | Weiner et al. |
| 5,843,770 A | 12/1998 | Ill et al. |
| 5,854,418 A | 12/1998 | Chang et al. |
| 5,858,987 A | 1/1999 | Beer-Romero et al. |
| 5,985,662 A | 11/1999 | Anderson et al. |
| 6,030,955 A | 2/2000 | Stein et al. |
| 6,107,062 A | 8/2000 | Hu et al. |
| 6,114,167 A | 9/2000 | Symonds et al. |
| 6,133,244 A | 10/2000 | Michel et al. |
| 6,147,123 A | 11/2000 | Chojkier et al. |
| 6,184,369 B1 | 2/2001 | Rando et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,228,642 B1 | 5/2001 | Baker et al. |
| 6,239,116 B1 | 5/2001 | Krieg et al. |
| 6,339,068 B1 | 1/2002 | Krieg et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,479,504 B1 | 11/2002 | Macfarlane et al. |
| 6,498,147 B2 | 12/2002 | Nerenberg et al. |

(Continued)

FOREIGN PATENT DOCUMENTS

CN            1 468 957          1/2004

(Continued)

OTHER PUBLICATIONS

Infante-Duarte et al., Th1/Th2 balance in infection. Springer Seminars in Immunopathology, 1999, 21: 317-338.*

Aoki et al. Use of cytokines in infection. Expert Opin. Emerg. Drugs, 2004, vol. 9, No. 2, 223-236.*

Bohn et al., Ambiguous role of interleukin-12 in *Yersinia enterocolitica* infection in susceptible and resistant mouse strains. Infect. Immune., 1998, vol. 66, 2213-2220.*

Sakao et al. IL-18-deficient mice are resistant to endotoxin-induced liver injury but highly susceptible to endotoxin shock. Int. Immunol., 1999, vol. 11, 471-480.*

(Continued)

*Primary Examiner* — N. M Minnifield
(74) *Attorney, Agent, or Firm* — Wolf, Greenfield & Sacks, P.C.; Gregg C. Benson

(57) ABSTRACT

The invention provides methods for identifying and treating subjects having hepatitis C infections. In some instances, the subjects are those that are non-responsive to non-CpG therapy. Preferably, the subjects are treated with C class CpG immunostimulatory nucleic acids having a semi-soft backbone.

1 Claim, 6 Drawing Sheets

U.S. PATENT DOCUMENTS

| | | |
|---|---|---|
| 6,503,533 B1 | 1/2003 | Korba et al. |
| 6,514,948 B1 | 2/2003 | Raz et al. |
| 6,521,637 B2 | 2/2003 | Macfarlane |
| 6,534,062 B2 | 3/2003 | Raz et al. |
| 6,552,006 B2 | 4/2003 | Raz et al. |
| 6,558,670 B1 | 5/2003 | Friede et al. |
| 6,562,798 B1 | 5/2003 | Schwartz |
| 6,589,940 B1 | 7/2003 | Raz et al. |
| 6,610,308 B1 | 8/2003 | Haensler |
| 6,610,661 B1 | 8/2003 | Carson et al. |
| 6,653,292 B1 | 11/2003 | Krieg et al. |
| 6,727,230 B1 | 4/2004 | Hutcherson et al. |
| 6,737,066 B1 | 5/2004 | Moss |
| 6,821,957 B2 | 11/2004 | Krieg et al. |
| 6,835,395 B1 | 12/2004 | Semple et al. |
| 6,943,240 B2 | 9/2005 | Bauer et al. |
| 6,949,520 B1 | 9/2005 | Hartmann et al. |
| 6,962,709 B2 | 11/2005 | Koelle et al. |
| 6,984,729 B1 | 1/2006 | Frank et al. |
| 7,001,890 B1 | 2/2006 | Wagner et al. |
| 7,157,437 B2 | 1/2007 | Van Nest |
| 7,223,741 B2 | 5/2007 | Krieg |
| 7,271,156 B2 | 9/2007 | Krieg et al. |
| 7,354,711 B2 | 4/2008 | Macfarlane |
| 7,402,572 B2 | 7/2008 | Krieg et al. |
| 7,410,975 B2 | 8/2008 | Lipford et al. |
| 7,488,490 B2* | 2/2009 | Davis et al. ............... 424/278.1 |
| 7,514,414 B2* | 4/2009 | Klinman et al. ............. 514/44 R |
| 7,517,861 B2* | 4/2009 | Krieg et al. ................. 514/44 R |
| 7,524,828 B2 | 4/2009 | Krieg et al. |
| 7,534,772 B2 | 5/2009 | Weiner et al. |
| 7,566,703 B2 | 7/2009 | Krieg et al. |
| 7,569,553 B2 | 8/2009 | Krieg |
| 7,576,066 B2 | 8/2009 | Krieg |
| 7,585,847 B2 | 9/2009 | Bratzler et al. |
| 7,605,138 B2 | 10/2009 | Krieg |
| 7,615,227 B2* | 11/2009 | Klinman et al. ............. 424/198.1 |
| 7,615,539 B2* | 11/2009 | Uhlmann et al. ............. 514/44 R |
| 7,666,674 B2* | 2/2010 | Klinman et al. ............... 435/375 |
| 7,674,777 B2* | 3/2010 | Krieg et al. ................. 514/44 R |
| 7,713,529 B2* | 5/2010 | Krieg et al. ................. 424/184.1 |
| 7,723,022 B2* | 5/2010 | Krieg et al. ........................ 435/5 |
| 7,723,500 B2* | 5/2010 | Krieg et al. ................... 536/23.1 |
| 7,758,876 B2* | 7/2010 | Klinman et al. ............. 424/278.1 |
| 7,776,344 B2* | 8/2010 | Hartmann et al. ......... 424/278.1 |
| 7,795,235 B2* | 9/2010 | Krieg et al. ................. 514/44 R |
| 7,807,803 B2* | 10/2010 | Krieg ........................... 536/23.1 |
| 7,820,379 B2 | 10/2010 | Bauer et al. |
| 7,825,097 B2* | 11/2010 | Davis et al. ................. 514/44 R |
| 7,879,810 B2 | 2/2011 | Krieg et al. |
| 7,888,327 B2 | 2/2011 | Krieg et al. |
| 2001/0044416 A1 | 11/2001 | McCluskie et al. |
| 2001/0046967 A1 | 11/2001 | Van Nest et al. |
| 2002/0028784 A1 | 3/2002 | Van Nest et al. |
| 2002/0064515 A1 | 5/2002 | Krieg et al. |
| 2002/0065236 A1 | 5/2002 | Yew et al. |
| 2002/0091097 A1 | 7/2002 | Bratzler et al. |
| 2002/0098199 A1 | 7/2002 | Van Nest et al. |
| 2002/0107212 A1 | 8/2002 | Van Nest et al. |
| 2002/0142977 A1 | 10/2002 | Raz et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0168340 A1 | 11/2002 | Agrawal |
| 2002/0192184 A1 | 12/2002 | Carpentier et al. |
| 2002/0198165 A1 | 12/2002 | Bratzler et al. |
| 2003/0026782 A1 | 2/2003 | Krieg |
| 2003/0026801 A1 | 2/2003 | Weiner et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0072762 A1 | 4/2003 | Van de Winkel et al. |
| 2003/0091599 A1 | 5/2003 | Davis et al. |
| 2003/0100527 A1 | 5/2003 | Krieg et al. |
| 2003/0119773 A1 | 6/2003 | Raz et al. |
| 2003/0125279 A1 | 7/2003 | Junghans et al. |
| 2003/0139364 A1 | 7/2003 | Krieg et al. |
| 2003/0143213 A1 | 7/2003 | Raz et al. |
| 2003/0147870 A1 | 8/2003 | Raz et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0176389 A1 | 9/2003 | Raz et al. |
| 2003/0181406 A1 | 9/2003 | Schetter et al. |
| 2003/0186921 A1 | 10/2003 | Carson et al. |
| 2003/0191079 A1 | 10/2003 | Krieg et al. |
| 2003/0199466 A1 | 10/2003 | Fearon et al. |
| 2003/0212028 A1 | 11/2003 | Raz et al. |
| 2003/0216340 A1 | 11/2003 | Van Nest et al. |
| 2003/0224010 A1 | 12/2003 | Davis et al. |
| 2003/0232074 A1 | 12/2003 | Lipford et al. |
| 2003/0232856 A1 | 12/2003 | Macfarlane |
| 2004/0006010 A1 | 1/2004 | Carson et al. |
| 2004/0006034 A1 | 1/2004 | Raz et al. |
| 2004/0009942 A1 | 1/2004 | Van Nest et al. |
| 2004/0009949 A1 | 1/2004 | Krieg |
| 2004/0030118 A1 | 2/2004 | Wagner et al. |
| 2004/0038922 A1 | 2/2004 | Haensler et al. |
| 2004/0047869 A1 | 3/2004 | Garcon et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092468 A1 | 5/2004 | Schwartz et al. |
| 2004/0092472 A1 | 5/2004 | Krieg |
| 2004/0105872 A1 | 6/2004 | Klinman et al. |
| 2004/0106568 A1 | 6/2004 | Krieg et al. |
| 2004/0115219 A1 | 6/2004 | Ahn et al. |
| 2004/0131628 A1 | 7/2004 | Bratzler et al. |
| 2004/0132063 A1 | 7/2004 | Gierse |
| 2004/0132685 A1 | 7/2004 | Krieg et al. |
| 2004/0136948 A1 | 7/2004 | Fearon et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0191833 A1 | 9/2004 | Fink et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0004144 A1 | 1/2005 | Carson et al. |
| 2005/0009774 A1 | 1/2005 | Krieg et al. |
| 2005/0013812 A1 | 1/2005 | Dow et al. |
| 2005/0031638 A1 | 2/2005 | Dalemans et al. |
| 2005/0032734 A1 | 2/2005 | Krieg et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054590 A1 | 3/2005 | Averett |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0059626 A1 | 3/2005 | Van Nest et al. |
| 2005/0064401 A1 | 3/2005 | Olek et al. |

| | | |
|---|---|---|
| 2005/0070491 A1 | 3/2005 | Krieg et al. |
| 2005/0075302 A1 | 4/2005 | Hutcherson et al. |
| 2005/0079152 A1 | 4/2005 | Bot et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartman et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0196411 A1 | 9/2005 | Moss et al. |
| 2005/0197314 A1 | 9/2005 | Krieg et al. |
| 2005/0209184 A1 | 9/2005 | Klinman et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0255124 A1 | 11/2005 | Hougton et al. |
| 2005/0256073 A1 | 11/2005 | Lipford et al. |
| 2005/0266015 A1 | 12/2005 | Clerici et al. |
| 2005/0266025 A1 | 12/2005 | Voss |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2005/0287167 A1 | 12/2005 | zur Megede et al. |
| 2006/0003955 A1 | 1/2006 | Krieg et al. |
| 2006/0003962 A1 | 1/2006 | Ahluwalia et al. |
| 2006/0019239 A1 | 1/2006 | Ivins et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0165713 A1 | 7/2006 | Gough et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0251623 A1 | 11/2006 | Bachmann et al. |
| 2006/0251677 A1 | 11/2006 | Bachmann et al. |
| 2006/0264391 A1 | 11/2006 | Van Nest |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0226649 A1 | 9/2008 | Schetter et al. |
| 2009/0017021 A1 | 1/2009 | Davis et al. |
| 2009/0060927 A1 | 3/2009 | Wagner et al. |
| 2009/0142362 A1 | 6/2009 | Krieg et al. |
| 2009/0155212 A1 | 6/2009 | Bratzler et al. |
| 2009/0155307 A1 | 6/2009 | Davis et al. |
| 2009/0191188 A1 | 7/2009 | Krieg et al. |
| 2009/0202575 A1 | 8/2009 | Krieg et al. |
| 2009/0214578 A1 | 8/2009 | Bauer |
| 2009/0306177 A1 | 12/2009 | Uhlmann et al. |
| 2009/0311277 A1 | 12/2009 | Krieg |
| 2010/0166780 A1 | 7/2010 | Debelak et al. |
| 2010/0183639 A1 | 7/2010 | Uhlmann et al. |
| 2010/0285041 A1 | 11/2010 | Uhlmann et al. |
| 2011/0033421 A1 | 2/2011 | Hartmann et al. |

FOREIGN PATENT DOCUMENTS

| | | |
|---|---|---|
| EP | 0 302 758 A1 | 2/1989 |
| EP | 0 468 520 A2 | 1/1992 |
| KR | 2001063153 | 7/2001 |
| WO | WO 91/12811 A1 | 9/1991 |
| WO | WO 92/03456 A1 | 3/1992 |
| WO | WO 93/15207 A2 | 8/1993 |
| WO | WO 94/16737 A1 | 8/1994 |
| WO | WO 94/19945 A1 | 9/1994 |
| WO | WO 95/03407 A2 | 2/1995 |
| WO | WO 96/02555 A1 | 2/1996 |
| WO | WO 97/28259 A1 | 8/1997 |
| WO | WO 98/16247 A1 | 4/1998 |
| WO | WO 98/32462 A1 | 7/1998 |
| WO | WO 98/49288 A1 | 11/1998 |
| WO | WO 98/55495 A2 | 12/1998 |
| WO | WO 99/33488 A2 | 7/1999 |
| WO | WO 99/52549 A1 | 10/1999 |
| WO | WO 99/56755 A1 | 11/1999 |
| WO | WO 99/62923 A2 | 12/1999 |
| WO | WO 00/06588 A1 | 2/2000 |
| WO | WO 00/14217 A2 | 3/2000 |
| WO | WO 00/15256 A2 | 3/2000 |
| WO | WO 00/20039 A1 | 4/2000 |
| WO | WO 00/21556 A1 | 4/2000 |
| WO | WO 00/41463 A2 | 7/2000 |
| WO | WO 00/54803 A2 | 9/2000 |
| WO | WO 00/61151 A2 | 10/2000 |
| WO | WO 00/62787 A1 | 10/2000 |
| WO | WO 00/67023 A1 | 11/2000 |
| WO | WO 00/67787 A2 | 11/2000 |
| WO | WO 01/00232 A2 | 1/2001 |
| WO | WO 01/02007 A1 | 1/2001 |
| WO | WO 01/12223 A2 | 2/2001 |
| WO | WO 01/17550 A2 | 3/2001 |
| WO | WO 01/17551 A2 | 3/2001 |
| WO | WO 01/22990 A2 | 4/2001 |
| WO | WO 01/35991 A2 | 5/2001 |
| WO | WO 01/45750 A1 | 6/2001 |
| WO | WO 01/54719 A2 | 8/2001 |
| WO | WO 01/55341 A2 | 8/2001 |
| WO | WO 01/68077 A2 | 9/2001 |
| WO | WO 01/68078 A2 | 9/2001 |
| WO | WO 01/68103 A2 | 9/2001 |
| WO | WO 01/68116 A2 | 9/2001 |
| WO | WO 01/68117 A2 | 9/2001 |
| WO | WO 02/28428 A2 | 4/2002 |
| WO | WO 03/002065 A2 | 1/2003 |
| WO | WO 03/020889 A2 | 3/2003 |
| WO | WO 03/024481 A2 | 3/2003 |
| WO | WO 03/025119 A2 | 3/2003 |
| WO | WO 03/030656 A2 | 4/2003 |
| WO | WO 03/035836 A2 | 5/2003 |
| WO | WO 03/043572 A2 | 5/2003 |
| WO | WO 03/094963 A2 | 11/2003 |
| WO | WO 03/100040 A1 | 12/2003 |
| WO | WO 2004/007743 A2 | 1/2004 |
| WO | WO 2004/026888 A2 | 4/2004 |
| WO | WO 2004/094671 A2 | 11/2004 |
| WO | WO 2005/004907 A1 | 1/2005 |
| WO | WO 2005/004910 A2 | 1/2005 |
| WO | WO 2005/023289 A1 | 3/2005 |
| WO | WO 2005/025583 A2 | 3/2005 |
| WO | WO 2005/079419 A2 | 9/2005 |
| WO | WO 2006/032674 A1 | 3/2006 |

| WO | WO 2006/080946 A2 | 8/2006 |
| WO | WO 2006/108358 A1 | 10/2006 |
| WO | WO 2007/031877 A2 | 3/2007 |
| WO | WO 2007/038720 A2 | 4/2007 |
| WO | WO 2007/068747 A1 | 6/2007 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 A2 | 6/2008 |
| WO | WO 2008/139262 A2 | 11/2008 |

OTHER PUBLICATIONS

Zaitseva et al. Interferon gamma and interleukin 6 modulate the susceptibility of macrophages to human immunodeficiency virus type 1 infection. Blood, 2000, vol. 96, 3109-3117.*

Masihi, K. Fighting infection using immunomodulatory agents. Expert Opin. Biol. Ther., 2001, vol. 1, No. 4, 641-653.*

Krieg et al., CpG motif in bacterial DNA and their immune effects. Annu. Rev. Immunol., 2002, vol. 20, 709-760.*

Mutwiri et al. Biological activity of immunostimulatory CpG DNA motifs in domestic animals. Veterinary Immunology and Immunopathology, 2003, vol. 91, 89-103.*

Yamamoto et al., Oligodeoxyribonucleotides with 5'ACGT-3' or 5TCGA-3 sequence induce production of interferons. Curr. Top. Microbiol. Immunol. 2000, vol. 247, 23-40.*

Equils et al. Toll-like receptor 2 (TLR2) and TLR9 signaling resulted from HIV-long terminal repeat transactivation and HIV replication in HIV-1 transgenic mouse spleen cells: implications of simultaneous activation of TLRs on HIV replication. J. Immunol. 2003, 170, 5159-5164.*

Agrawal, et al. Was induction of HIV1 through TLR9? J. Immunol. 2003, 171, 1621-1621.*

Olbrich et al. Preinfection treatment of resistant mice with CpG oligodeoxynucleotides renders them susceptible to friend retrovirus-induced leukemia. J. Virol., 2003, 77, 10658-10662.*

Knipe DM, Howley PM, eds. Fields virology. 4th ed. vol. 1. Philadelphia: Lippincott Williams & Wilkins, 2001, 1004-1016 and 1127-1161.*

Hahn. Subversion of immune responses by hepatitis C virus: immunomodulatory strategies beyond evasion? Current opinion in Immunology, 2003, vol. 15, 443-449.*

De Francesco et al. Challenges and successes in developing new therapies of hepatitis C. Nature, 2005, vol. 436, 953-960.*

Witherell et al. ISIS-14803 ISIS Pharmaceuticals. Current Opinion in Investigational Drugs, 2001, vol. 2, No. 11, 1523-1529.*

Kamal et al. Peginterferon alone or with ribavirin enhances HCV-specific CD4+ T-helper 1 responses in patients with chronic hepatitis C. Gastroenterology, Oct. 5, 2002, vol. 123, 1070-1083.*

Hanecak et al. Antisense oligonucleotide inhibition of hepatitis C virus gene expression in transformed hepatocytes. Journal of Virology, Aug. 1996, vol. 70, No. 8, 5203-5212.*

[No Author Listed] "Hepatitis C: Safety and Efficacy of CPG 10101," Hepatitis Journal Review. Hepatitis C Support Project. Dec. 10, 2007;4(22):1-3.

[No Author Listed] "Coley Pharmaceutical Group Updates Hepatitis C Drug Development Strategy," Press Release, Wellesley, MA, Jan. 22, 2007/PRNewswire-FirstCall—Coley Pharmaceutical Group, Inc.

Deutsch et al., Old and emerging therapies in chronic hepatitis C: an update. J Viral Hepat. Jan. 2008;15(1):2-11.

Jacobson et al., "CPG10101 HCV Toll-Receptor 9 Antagonist Phase II Study Results," 57th Annual Meeting of the American Association for the Study of Liver Diseases. Oct. 27-31, 2006. Boston, MA. 11 pages.

McHutchison et al., "Early Viral Response to New HCV Drug CPG 10101 Toll-Receptor Antagonist, in Combination with Pegylated Interferon and/or Ribavirin, in Chronic HCV Gentoype 1 Infected Patients with Prior Relapse Response," 41st Meeting of the European Association for the Study of Liver Diseases. Apr. 26-30, 2006. Vienna, Austria. 8 pages.

McHutchison et al., "Phase 1B Study Shows Toll-Like Receptor 9 Agonist CPG 10101 Decreases HCV RNA in Patients with Chronic Hepatitis C," 58th Annual Meeting of the American Association for the Study of Liver Diseases. Nov. 2-6, 2007. Boston, MA. 2 pages.

McHutchison et al., "Early Viral Response to CPG 10101 in Combination with Pegylated Interferon and/or Ribavirin, in Chronic HCV Gentoype 1 Infected Patients with Prior Relapse Response," 2006 European Association for the Study of the Liver (EASL) Apr. 26-30, 2006. Abstract. 1 page.

[No Author Listed] Antiviral Agents Bulletin. 5(6), 1992.

[No Author Listed] CPG10101 HCV Toll-Receptor 9 Antagonist Phase II Study Results. 57th Annual Meeting of the American Association for the Study of Liver Diseases. Oct. 27-311, 2006. Boston, MA. 9 pages.

Agrawal et al., Medicinal chemistry and therapeutic potential of CpG DNA. Trends Mol. Med. Mar. 2002;8(3):114-21.

Agrawal et al., Chapter 19: Pharmacokinetics and bioavailability of antisense oligonucleotides following oral and colorectal administrations in experimental animals. 1998:525-43.

Agrawal et al., Pharmacokinetics of antisense oligonucleotides. Clin Pharmacokinet. Jan. 1995;28(1):7-16. Review.

Agrawal et al., Inhibition of human immunodeficiency virus in early infected and chronically infected cells by antisense oligodeoxynucleotides and their phosphorothioate analogues. Proc Natl Acad Sci U S A. Oct. 1989;86(20):7790-4.

Ahluwalia et al., Immunostimulatory profiles from two classes of CpG ODN administered subcutaneously to healthy subjects. ICI FOCIS 2004. Poster.

Askew et al., CpG DNA induces maturation of dendritic cells with distinct effects on nascent and recycling MHC-II antigen-processing mechanisms. J Immunol. Dec. 15, 2000;165(12):6889-95.

Azad et al., Antiviral activity of a phosphorothioate oligonucleotide complementary to RNA of the human cytomegalovirus major immediate-early region. Antimicrob Agents Chemother. Sep. 1993;37(9):1945-54.

Bain et al., Impaired allostimulatory function of dendritic cells in chronic hepatitis C infection. Gastroenterology. Feb. 2001;120(2):512-24.

Ballas et al., Induction of NK activity in murine and human cells by CpG motifs in oligodeoxynucleotides and bacterial DNA. J Immunol. Sep. 1, 1996;157(5):1840-5.

Bassett et al., Protective immune response to hepatitis C virus in chimpanzees rechallenged following clearances of primary infection. Hepatology. Jun. 2001;33(6):1479-87.

Bauer et al., Human TLR9 confers responsiveness to bacterial DNA via species-specific CpG motif recognition. Proc Natl Acad Sci U S A. Jul. 31, 2001;98(16):9237-42.

Bauer et al., DNA activates human immune cells through a CpG sequence-dependent manner. Immunology. Aug. 1999;97(4):699-705.

Bauer et al., Bacterial CpG-DNA triggers activation and maturation of human CD11c-, CD123+ dendritic cells. J Immunol. Apr. 15, 2001;166(8):5000-7.

Boggs et al., Characterization and modulation of immune stimulation by modified oligonucleotides. Antisense Nucleic Acid Drug Dev. Oct. 1997;7(5):461-71.

Branda et al., Immune stimulation by an antisense oligomer complementary to the rev gene of HIV-1. Biochem Pharmacol. May 25, 1993;45(10):2037-43.

Branda et al., Amplification of antibody production by phosphorothioate oligodeoxynucleotides J Lab Clin Med. Sep. 1996;128(3):329-38.

Branda et al., B-cell proliferation and differentiation in common variable immunodeficiency patients produced by an antisense oligomer to the rev gene of HIV-1. Clin Immunol Immunopathol. May 1996;79(2):115-21.

Brazolot Millan et al., CpG DNA can induce strong Th1 humoral and cell-mediated immune responses against hepatitis B surface antigen in young mice. Proc Natl Acad Sci U S A. Dec. 22, 1998;95(26):15553-8.

Cacciarelli et al., Immunoregulatory cytokines in chronic hepatitis C virus infection: pre- and posttreatment with interferon alfa. Heptaology. Jul. 1996;24(1):6-9.

Calarota et al., Cellular cytotoxic response induced by DNA vaccination in HIV-1-infected patients. Lancet. May 2, 1998;351(9112):1320-5.

Cattaneo et al., Signals regulating hepatitis B surface antigen transcription. Nature. Sep. 22-28, 1983;305(5932):336-8.
Cella et al., Plasmacytoid monocytes migrate to inflamed lymph nodes and produce large amounts of type I interferon. Nat Med. Aug. 1999;5(8):919-23.
Chace et al., Bacterial DNA-induced NK cell IFN-gamma production is dependent on macrophage secretion of IL-12. Clin Immunol Immunopathol. Aug. 1997;84(2):185-93.
Chan et al., CpG-A and CpG-B oligodeoxynucleotides differentially affect the cytokine profile, chemokine receptor expression and T-cell priming function of human plasmacytoid dendritic cells. Blood. 2002;100:50b. Abstract #3666.
Chu et al., CpG oligodeoxynucleotides act as adjuvants that switch on T helper 1 (Th1) immunity. J Exp Med. Nov. 17, 1997;186(10):1623-31.
Collette et al., Specific Th1 cytokine down-regulation associated with primary clinically derived human immunodeficiency virus type 1 Nef gene-induced expression. J Immunol. Jan. 1, 1996;156(1):360-70.
Cooper et al., Safety and immunogenicity of CPG 7909 injection as an adjuvant to Fluarix influenza vaccine. Vaccine. Aug. 13, 2004;22(23-24):3136-43.
Cooper et al., CPG 7909 adjuvant improves hepatitis B virus vaccine seroprotection in antiretroviral-treated HIV-infected adults. AIDS. Sep. 23, 2005;19(14):1473-9.
Cooper et al., CPG 7909, an immunostimulatory TLR9 agonist oligodeoxynucleotide, as adjuvant to Engerix-B HBV vaccine in healthy adults: a double-blind phase I/II study. J Clin Immunol. Nov. 2004;24(6):693-701.
Cossum et al., Disposition of the 14C-labeled phosphorothioate oligonucleotide ISIS 2105 after intravenous administration to rats. J Pharmacol Exp Ther. Dec. 1993;267(3):1181-90.
Cowdery et al., Bacterial DNA induces NK cells to produce IFN-gamma in vivo and increases the toxicity of lipopolysaccharides. J Immunol. Jun. 15, 1996;156(12):4570-5.
Cowsert et al., In vitro evaluation of phosphorothioate oligonucleotides targeted to the E2 mRNA of papillomavirus: potential treatment for genital warts. Antimicrob Agents Chemother. Feb. 1993;37(2):171-7.
Dalod et al., Interferon alpha/beta and interleukin 12 responses to viral infections: pathways regulating dendritic cell cytokine expression in vivo. J Exp Med. Feb. 18, 2002;195(4):517-28.
Dalpke et al., CpG DNA in the prevention and treatment of infections. BioDrugs. 2002;16(6):419-31. Abstract only.
Davis et al., CpG DNA is a potent enhancer of specific immunity in mice immunized with recombinant hepatitis B surface antigen. J Immunol. Jan. 15, 1998;160(2):870-6.
Davis, Use of CpG DNA for enhancing specific immune responses. Curr Top Microbiol Immunol. 2000;247:171-83.
Davis et al., CpG ODN is safe and highly effective in humans as adjuvant to HBV vaccine: Preliminary results of Phase I trial with CpG ODN 7909. Third Annual Conference on Vaccine Res. 2000. Abstract s25, No. 47.
Davis et al., CpG DNA overcomes hyporesponsiveness to hepatitis B vaccine in orangutans. Vaccine. Mar. 17, 2000;18(18):1920-4.
Fields et al., Fields' Virology. 2001;1:1153.
Gallichan et al., Intranasal immunization with CpG oligodeoxynucleotides as an adjuvant dramatically increases IgA and protection against herpes simplex virus-2 in the genital tract. J Immunol. Mar. 1, 2001;166(5):3451-7.
Geissler et al., Enhancement of cellular and humoral immune responses to hepatitis C virus core protein using DNA-based vaccines augmented with cytokine-expressing plasmids. J Immunol. Feb. 1, 1997;158(3):1231-7.
Goldberg et al., Beyond danger: unmethylated CpG dinucleotides and the immunopathogenesis of disease. Immunol Lett. Jul. 3, 2000;73(1):13-8.
Gramzinski et al., Immune response to a hepatitis B DNA vaccine in Aotus monkeys: a comparison of vaccine formulation, route, and method of administration. Mol Med. Feb. 1998;4(2):109-18.
Halperin et al., A phase I study of the safety and immunogenicity of recombinant hepatitis B surface antigen co-administered with an immunostimulatory phosphorothioate oligonucleotide adjuvant. Vaccine. Jun. 2, 2003;21(19-20):2461-7.
Halpern et al., Bacterial DNA induces murine interferon-gamma production by stimulation of interleukin-12 and tumor necrosis factor-alpha. Cell Immunol. Jan. 10, 1996;167(1):72-8.
Harandi et al., A protective role of locally administered immunostimulatory CpG oligodeoxynucleotide in a mouse model of genital herpes infection. J Virol. Jan. 2003;77(2):953-62.
Hartmann et al., CpG DNA and LPS induce distinct patterns of activation in human monocytes Gene Ther. May 1999;6(5):893-903.
Hartmann et al., Mechanism and function of a newly identified CpG DNA motif in human primary B cells. J Immunol. Jan. 15, 2000;164(2):944-53.
Hartmann et al., Delineation of a CpG phosphorothioate oligodeoxynucleotide for activating primate immune responses in vitro and in vivo. J Immunol. Feb. 1, 2000;164(3):1617-24.
Hartmann et al., CpG DNA: a potent signal for growth, activation, and maturation of human dendritic cells. Proc Natl Acad Sci U S A. Aug. 3, 1999;96(16):9305-10.
Heeg et al., CpG DNA as a Th1 trigger. Int Arch Allergy Immunol. Feb. 2000;121(2):87-97.
Herbst et al., Immunostimulatory CpG treatment for genital HSV-2 infections. J Antimicrob Chemother. Dec. 2003;52(6):887-9. Epub Oct. 29, 2003. Review.
Ho, Toward HIV eradication or remission: the tasks ahead. Science. Jun. 19, 1998;280(5371):1866-7.
Hopkin et al., Curbing the CpGs of Bacterial and Viral DNA. BioMedNet. Jun. 25, 1999; Issue 57.
Horner et al., Mucosal adjuvanticity of immunostimulatory DNA sequences. Springer Semin Immunopathol. 2000;22(1-2):133-46.
Huang et al., Induction and regulation of Th1-inducing cytokines by bacterial DNA, lipopolysaccharide, and heat-inactivated bacteria. Infect Immun. Dec. 1999;67(12):6257-63.
Iho et al., Oligodeoxynucleotides containing palindrome sequences with internal 5'-CpG-3' act directly on human NK and activated T cells to induce IFN-gamma production in vitro. J Immunol. Oct. 1, 1999;163(7):3642-52.
Imai et al., Relation of interferon therapy and hepatocellular carcinoma in patients with chronic hepatitis C. Osaka Hepatocellular Carcinoma Prevention Study Group. Ann Intern Med. Jul. 15, 1998;129(2):94-9.
Ito et al., CpG oligodeoxynucleotides increase the susceptibility of normal mice to infection by Candida albicans. Infect Immun. Sep. 2005;73(9):6154-6.
Iversen et al., Pharmacokinetics of an antisense phosphorothioate oligodeoxynucleotide against rev from human immunodeficiency virus type 1 in the adult male rat following single injections and continuous infusion. Antisense Res Dev. 1994 Spring;4(1):43-52.
Jakob et al., Activation of cutaneous dendritic cells by CpG-containing oligodeoxynucleotides: a role for dendritic cells in the augmentation of Th1 responses by immunostimulatory DNA. J. Immunol. Sep. 15, 1998;161(6):3042-9.
Jakob et al., Bacterial DNA and CpG-containing oligodeoxynucleotides activate cutaneous dendritic cells and induce IL-12 production: implications for the augmentation of Th1 responses. Int. Arch Allergy Immunol. Feb.-Apr. 1999;118(2-4):457-61.
Jiang et al., Enhancing immunogenicity by CpG DNA. Curr Opin Mol Ther. Apr. 2003;5(2):180-5.
Jiao et al., Enhanced hepatitis C virus NS3 specific Th1 immune responses induced by co-delivery of protein antigen and CpG with cationic liposomes. J Gen Virol. Jun. 2004;85(Pt 6):1545-53.
Johnson et al., Non-specific resistance against microbial infections induced by polyribonucleotide complexes. In: Immunopharmacology of infection diseases: Vaccine adjuvants and modulators of non-specific resistance. 1987: 291-301.
Joseph et al., Liposomal immunostimulatory DNA sequence (ISS-ODN): an efficient parenteral and mucosal adjuvant for influenza and hepatitis B vaccines. Vaccine. Sep. 10, 2002;20(27-28):3342-54.
Kandimalla et al., Towards optimal design of second-generation immunomodulatory oligonucleotides. Curr Opin Mol Ther. Apr. 2002;4(2):122-9.

Kataoka et al., Immunotherapeutic potential in guinea-pig tumor model of deoxyribonucleic acid from Mycobacterium bovis BCG complexed with poly-L-lysine and carboxymethylcellulose. Jpn J Med Sci Biol. Oct. 1990;43(5):171-82.

Kimura et al., Binding of oligoguanylate to scavenger receptors is required for oligonucleotides to augment NK cell activity and induce IFN. J Biochem (Tokyo). Nov. 1994;116(5):991-4.

Klinman et al., Immunotherapeutic applications of CpG-containing oligodeoxynucleotides. Drug News Perspect. Jun. 2000;13(5):289-96.

Klinman et al., Immunotherapeutic uses of CpG oligodeoxynucleotides. Nat Rev Immunol. Apr. 2004;4(4):249-58.

Klinman et al., Repeated administration of synthetic oligodeoxynucleotides expressing CpG motifs provides long-term protection against bacterial infection. Infect Immun. Nov. 1999;67(11):5658-63.

Klinman et al., Activation of the innate immune system by CpG oligodeoxynucleotides: immunoprotective activity and safety. Springer Semin Immunopathol. 2000;22(1-2):173-83.

Klinman et al., Immune recognition of foreign DNA: a cure for bioterrorism? Immunity. Aug. 1999;11(2):123-9.

Klinman et al., Contribution of CpG motifs to the immunogenicity of DNA vaccines. J Immunol. Apr. 15, 1997;158(8):3635-9.

Klinman et al., CpG motifs present in bacteria DNA rapidly induce lymphocytes to secrete interleukin 6, interleukin 12, and interferon gamma. Proc Natl Acad Sci U S A. Apr. 2, 1996;93(7):2879-83.

Knipe et al., eds., Fields' Virology. 2001;1:1564.

Kovarik et al., CpG oligodeoxynucleotides can circumvent the Th2 polarization of neonatal responses to vaccines but may fail to fully redirect Th2 responses established by neonatal priming. J Immunol. Feb. 1, 1999;162(3):1611-7.

Kranzer et al. CpG-oligodeoxynucleotides enhance T-cell receptor-triggered interferon-gamma production and up-regulation of CD69 via induction of antigen-presenting cell-derived interferon type I and interleukin-12. Immunology. Feb. 2000;99(2):170-8.

Krieg et al., Immune effects and therapeutic applications of CpG motifs in bacterial DNA. Immunopharmacology. Jul. 25, 2000;48(3):303-5.

Krieg et al., Lymphocyte activation mediated by oligodeoxynucleotides or DNA containing novel unmethylated CpG motifs. American College of Rheumatology 58th National Scientific Meeting. Minneapolis, Minnesota, Oct. 22, 1994. Abstracts. Arthritis Rheum. Sep. 1994;37(9 Suppl).

Krieg et al., Oligodeoxynucleotide modifications determine the magnitude of B cell stimulation by CpG motifs. Antisense Nucleic Acid Drug Dev. 1996 Summer;6(2):133-9.

Krieg et al., Phosphorothioate oligodeoxynucleotides: antisense or anti-protein? Antisense Res Dev. 1995 Winter;5(4):241.

Krieg et al., Leukocyte stimulation by oligodeoxynucleotides. In: Applied Antisense Oligonucleotide Technology. 1998:431-48.

Krieg et al., CpG motifs in bacterial DNA trigger direct B-cell activation. Nature. Apr. 6, 1995;374(6522):546-9.

Krieg et al., The role of CpG dinucleotides in DNA vaccines. Trends Microbiol. Jan. 1998;6(1):23-7.

Krieg, An innate immune defense mechanism based on the recognition of CpG motifs in microbial DNA. J Lab Clin Med. Aug. 1996;128(2):128-33.

Krieg et al., Direct immunologic activities of CpG DNA and implications for gene therapy. J Gene Med. Jan.-Feb. 1999;1(1):56-63.

Krieg et al., CpG motifs in bacterial DNA and their immune effects. Annu Rev Immunol. 2002;20:709-60.

Krieg et al., Causing a commotion in the blood: immunotherapy progresses from bacteria to bacterial DNA. Immunol Today. Oct. 2000;21(10):521-6.

Krieg et al., Chapter 8: Immune Stimulation by Oligonucleotides. In: Antisense Research and Application. Crooke, Ed. 1998:243-62.

Krieg et al., A role for endogenous retroviral sequences in the regulation of lymphocyte activation. J Immunol. Oct. 15, 1989;143(8):2448-51.

Krieg et al,. Bacterial DNA or oligonucleotides containing CpG motifs protect mice from lethal L. monocytogenes challenge. 1996 Meeting on Molecular Approaches to the Control of Infectious Diseases. Cold Spring Harbor Laboratory, Sep. 9-13, 1996:116.

Krieg et al., Enhancing vaccines with immune stimulatory CpG DNA. Curr Opin Mol Ther. Feb. 2001;3(1):15-24.

Krieg, Chapter 7: CpG oligonucleotides as immune adjuvants. Ernst Schering Research Found Workshop 2001; 30:105-18.

Krieg, Immune effects and mechanisms of action of CpG motifs. Vaccine. Nov. 8, 2001;19(6):618-22.

Krieg et al., Chapter 17:Immune stimulation by oligonucleotides. in Antisense Drug Tech. 2001;1394:471-515.

Krieg et al., Mechanisms and applications of immune stimulatory CpG oligodeoxynucleotides. Biochim Biophys Acta. Dec. 10, 1999;1489(1):107-16.

Krieg et al., The CpG motif: Implications for clinical immunology. BioDrugs. Nov. 1, 1998;10(5):341-6.

Krieg, The role of CpG motifs in innate immunity. Curr Opin Immunol. Feb. 2000;12(1):35-43.

Krieg et al., Mechanisms and therapeutic applications of immune stimulatory CpG DNA Pharmacol Ther. Nov. 1999;84(2):113-20.

Krieg et al., Sequence motifs in adenoviral DNA block immune activation by stimulatory CpG motifs. Proc Natl Acad Sci U S A. Oct. 13, 1998;95(21):12631-6.

Krieg et al., CpG DNA induces sustained IL-12 expression in vivo and resistance to Listeria monocytogenes challenge. J Immunol. Sep. 1, 1998;161(5):2428-34.

Krieg et al., CpG DNA: a novel immunomodulator. Trends Microbiol. Feb. 1999;7(2):64-5.

Krieg, Signal transduction induced by immunostimulatory CpG DNA. Springer Semin Immunopathol. 2000;22(1-2):97-105.

Krieg et al., How to exclude immunostimulatory and other nonantisense effects of antisense oligonucleotides. Manual of Antisense. 1999:79-89.

Krieg et al., Unmethylated CpG DNA protects mice from lethal listeria monocytogenes challenge Vaccines. 1997; 97:77-9.

Krieg et al., Infection. In: McGraw Hill Book. 1996:242-3.

Krieg et al., Lymphocyte activation by CpG dinucleotide motifs in prokaryotic DNA. Trends Microbiol. Feb. 1996;4(2):73-6.

Krieg et al., Mechanism of action of CpG DNA. Curr Top Microbiol Immunol. 2000;247:1-21.

Krieg, Therapeutic potential of Toll-like receptor 9 activation. Nat Rev Drug Discov. Jun. 2006;5(6):471-84.

Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71.

Krieg et al., Identification of an oligodeoxynucleotide sequence motif that specifically inhibits phosphorylation by protein tyrosine kinases. Antisense Nucleic Acid Drug Dev. Apr. 1997;7(2):115-23.

Krieg, Now I know my CpGs.Trends Microbiol. Jun. 2001;9(6):249-52.

Krieg, Antiinfective applications of toll-like receptor 9 agonists. Proc Am Thorac Soc. Jul. 2007;4(3):289-94.

Krug et al., Identification of CpG oligonucleotide sequences with high induction of IFN-alpha/beta in plasmacytoid dendritic cells. Eur J Immunol. Jul. 2001;31(7):2154-63.

Krug et al., Toll-like receptor expression reveals CpG DNA as a unique microbial stimulus for plasmacytoid dendritic cells which synergizes with CD40 ligand to induce high amounts of IL-12 Eur J Immunol. Oct. 2001;31(10):3026-37.

Kuhober et al., DNA immunization induces antibody and cytotoxic T cell responses to hepatitis B core antigen in H-2b mice. J Immunol. May 15, 1996;156(10):3687-95. Abstract only.

Kulkarni et al., Effect of dietary nucleotides on response to bacterial infections JPEN J Parenter Enteral Nutr. Mar.-Apr. 1986;10(2):169-71.

Kuramoto et al., Oligonucleotide sequences required for natural killer cell activation. Jpn J Cancer Res. Nov. 1992;83(11):1128-31.

Kuramoto et al., In situ infiltration of natural killer-like cells induced by intradermal injection of the nucleic acid fraction from BCG. Microbiol Immunol. 1989;33(11):929-40.

Kwant et al., Intravaginal immunization with viral subunit protein plus CpG oligodeoxynucleotides induces protective immunity against HSV-2. Vaccine. Aug. 13, 2004;22(23-24):3098-104.

Lamm et al., Mechanisms of Ig-A mediated mucosal defense. Vaccine Research. 1992;1(3):169-173.

Le Borgne et al., In vivo induction of specific cytotoxic T lymphocytes in mice and rhesus macaques immunized with DNA vector encoding an HIV epitope fused with hepatitis B surface antigen. Virology. Jan. 20, 1998;240(2):304-15. Abstract only.

Lee et al., Immuno-stimulatory effects of bacterial-derived plasmids depend on the nature of the antigen in intramuscular DNA inoculations. Immunology. Jul. 1998;94(3):285-9.

Lipford et al., CpG-containing synthetic oligonucleotides promote B and cytotoxic T cell responses to protein antigen: a new class of vaccine adjuvants. Eur J Immunol. Sep. 1997;27(9):2340-4.

Lipford et al., Immunostimulatory DNA: sequence-dependent production of potentially harmful or useful cytokines. Eur J Immunol. Dec. 1997;27(12):3420-6.

Lipford et al., Bacterial DNA as immune cell activator. Trends Microbiol. Dec. 1998;6(12):496-500.

Liu et al., Immunization of non-human primates with DNA vaccines. Vaccine. Jun. 1997;15(8):909-12.

Ma et al., DNA-based vaccination against hepatitis C virus (HCV): effect of expressing different forms of HCV E2 protein and use of CpG-optimized vectors in mice. Vaccine. Sep. 10, 2002;20(27-28):3263-71.

Major et al. Chapter 34 Hepatitis C Viruses. In Fields' Virology. 2001; 1:1127-61.

Malanchere-Bres et al., CpG oligodeoxynucleotides with hepatitis B surface antigen (HbsAg) for vaccination in HbsAg-transgenic mice. J Virol. Jul. 2001;75(14):6482-91.

Martin-Orozco et al., Enhancement of antigen-presenting cell surface molecules involved in cognate interactions by immunostimulatory DNA sequences. Int Immunol. Jul. 1999;11(7):1111-8.

Matsukura et al., Regulation of viral expression of human immunodeficiency virus in vitro by an antisense phosphorothioate oligodeoxynucleotide against rev (art/trs) in chronically infected cells. Proc Natl Acad Sci U S A. Jun. 1989;86(11):4244-8.

McCluskie et al., CpG DNA as mucosal adjuvant. Immunol Letts. 1999;69(1):30-1. Abstract #5.2.

McCluskie et al., CpG DNA is a potent enhancer of systemic and mucosal immune responses against hepatitis B surface antigen with intranasal administration to mice. J Immunol. Nov. 1, 1998;161(9):4463-6.

McCluskie et al., CpG DNA as mucosal adjuvant. Vaccine. 2000;18: 231-7.

McCluskie et al., Oral, intrarectal and intranasal immunizations using CpG and non-CpG oligodeoxynucleotides as adjuvants. Vaccine. Oct. 15, 2000;19(4-5):413-22.

McCluskie et al., Immunization against hepatitis B virus by mucosal administration of antigen-antibody complexes. Viral Immunol. 1998;11(4):245-52.

McCluskie et al., CpG DNA is an effective oral adjuvant to protein antigens in mice. Vaccine. Nov. 22, 2000;19(7-8):950-7.

McCluskie et al., The potential of oligodeoxynucleotides as mucosal and parenteral adjuvants. Vaccine. Mar. 21, 2001;19(17-19):2657-60.

McCluskie et al., The use of CpG DNA as a mucosal vaccine adjuvant. Curr Opin Investig Drugs. Jan. 2001;2(1):35-9.

McCluskie et al., Parenteral and mucosal prime-boost immunization strategies in mice with hepatitis B surface antigen and CpG DNA. FEMS Immunol Med Microbiol. Feb. 18, 2002;32(3):179-85.

McCluskie et al., The role of CpG in DNA vaccines. Springer Semin Immunopathol. 2000;22(1-2):125-32.

McCluskie et al., Treatment of intravaginal HSV-2 infection in mice: a comparison of CpG oligodeoxynucleotides and resiquimod (R-848). Antiviral Res. Feb. 2006;69(2):77-85. Epub Dec. 5, 2005.

McHutchison et al., Final results of a multi-center phase 1B, randomized, placebo-controlled, dose-escalation trial of CpG 10101 in patients with chronic hepatitis C virus. 41st Annual Meeting of European Association for the Study of the Liver (EASL). Apr. 30, 2006, Vienna, Austria; Presented Abstract #111.

McHutchison et al., Early clinical results with CpG 10101, a new investigational antiviral TLR9 agonist being developed for treatment of subjects chronically infected with hepatitis C virus. 12th International Symposium on Viral Hepatitis and Liver Disease (ISVHLD). Jul. 3, 2006, Paris, France; Presented Abstract #O105.

Messina et al., The influence of DNA structure on the in vitro stimulation of murine lymphocytes by natural and synthetic polynucleotide antigens. Cell Immunol. Mar. 1993;147(1):148-57.

Mojcik et al., Administration of a phosphorothioate oligonucleotide antisense to murine endogenous retroviral MCF env causes immune effects in vivo in a sequence-specific manner. Clin Immunol Immunopathol. May 1993;67(2):130-6.

Moldoveanu et al., CpG DNA, a novel immune enhancer for systemic and mucosal immunization with influenza virus. Vaccine. Jul. 1998;16(11-12):1216-24.

Moseman et al., Human plasmacytoid dendritic cells activated by CpG oligodeoxynucleotides induce the generation of CD4+CD25+ regulatory T cells. J Immunol. Oct. 1, 2004;173(7):4433-42.

Moss et al., In vitro immune function after vaccination with an inactivated, gp120-depleted HIV-1 antigen with immunostimulatory oligodeoxynucleotides. Vaccine. Jan. 6, 2000;18(11-12):1081-7.

Nesburn et al., Local and systemic B cell and Th1 responses induced following ocular mucosal delivery of multiple epitopes of herpes simplex virus type 1 glycoprotein D together with cytosine-phosphate-guanine adjuvant. Vaccine. Jan. 4, 2005;23(7):873-83.

Oxenius et al., CpG-containing oligonucleotides are efficient adjuvants for induction of protective antiviral immune responses with T-cell peptide vaccines. J Virol. May 1999;73(5):4120-6.

Payette et al., History of vaccines and positioning of current trends. Curr Drug Targets Infect Disord. Nov. 2001;1(3):241-7.

Pisetsky et al., The immunologic properties of DNA. J Immunol. Jan. 15, 1996;156(2):421-3.

Pisetsky et al., Immunological properties of bacterial DNA. Ann N Y Acad Sci. Nov. 27, 1995;772:152-63.

Pisetsky et al., Stimulation of murine lymphocyte proliferation by a phosphorothioate oligonucleotide with antisense activity for herpes simplex virus. Life Sci. 1994;54(2):101-7.

Pisetsky, Immunologic consequences of nucleic acid therapy. Antisense Res Dev. 1995 Fall;5(3):219-25.

Pisetsky et al., Stimulation of in vitro proliferation of murine lymphocytes by synthetic oligodeoxynucleotides. Mol Biol Rep. Oct. 1993;18(3):217-21.

Pisetsky, The influence of base sequence on the immunostimulatory properties of DNA. Immunol Res. 1999;19(1):35-46.

Pisetsky et al., The influence of base sequence on the immunological properties of defined oligonucleotides. Immunopharmacology. Nov. 1998;40(3):199-208.

Polanczyk et al., Immunostimulatory effects of DNA and CpG motifs. Cent Eur J of Immunol. 2000;25(3):160-6.

Rankin et al., CpG motif identification for veterinary and laboratory species demonstrates that sequence recognition is highly conserved. Antisense Nucleic Acid Drug Dev. Oct. 2001;11(5):333-40.

Raz et al., Potential role of immunostimulatory DNA sequences (ISS) in genetic immunization and autoimmunity. ACR Poster Session C: Cytokines and Inflammatory Mediators. Oct. 20, 1996; Abstract 615.

Rees et al., CpG-DNA protects against a lethal orthopoxvirus infection in a murine model. Antiviral Res. Feb. 2005;65(2):87-95.

Roffi et al., Breakthrough during recombinant interferon alfa therapy in patients with chronic hepatitis C virus infection: prevalence, etiology, and management. Hepatology. Mar. 1995;21(3):645-9.

Roman et al., Immunostimulatory DNA sequences function as T helper-1-promoting adjuvants. Nat Med. Aug. 1997;3(8):849-54.

Rothenfusser et al., Recent advances in immunostimulatory CpG oligonucleotides. Curr Opin Mol Ther. Apr. 2003;5(2):98-106.

Rynkiewicz et al., Marked enhancement of antibody response to anthrax vaccine adsorbed with CPG 7909 in healthy volunteers. 45th Intersci. Conf. Antimicrob. Agents Chemother. Sep. 21-24, 2005; New Orleans, Louisiana. Meeting Poster.

Sajic et al., Parameters of CpG oligodeoxynucleotide-induced protection against intravaginal HSV-2 challenge. J Med Virol. Dec. 2003;71(4):561-8.

Sato et al., Immunostimulatory DNA sequences necessary for effective intradermal gene immunization. Science. Jul. 19, 1999;273(5273):352-4.

Satoh et al., The study of mechanisms in CpG oligodeoxynucleotides-induced aggravation in murine allergic contact dermititis to 2,4-dinitrofluorobenzene. Fukushima Igaku Zasshi. 2002;52(3):237-50.
Scheule, The role of CpG motifs in immunostimulation and gene therapy. Adv Drug Deliv Rev. Nov. 15, 2000;44(2-3):119-34.
Schirmbeck et al., Nucleic acid vaccination primes hepatitis B virus surface antigen-specific cytotoxic T lymphocytes in nonresponder mice. J Virol. Oct. 1995;69(10):5929-34.
Schlaak et al., Interleukin 12 enhances deficient HCV-antigen-induced Th1-type immune response of peripheral blood mononuclear cells. J Med Virol. Oct. 1998;56(2):112-7.
Schwartz et al., Bacterial DNA or oligonucleotides containing unmethylated CpG motifs can minimize lipopolysaccharide-induced inflammation in the lower respiratory tract through an IL-12-dependent pathway. J Immunol. Jul. 1, 1999;163(1):224-31.
Schwartz et al., CpG motifs in bacterial DNA cause inflammation in the lower respiratory tract. J Clin Invest. Jul. 1, 1997;100(1):68-73.
Sester et al., Phosphorothioate backbone modification modulates macrophage activation by CpG DNA. J Immunol. Oct. 15, 2000;165(8):4165-73.
Siegrist et al., Co-administration of CpG oligonucleotides enhances the late affinity maturation process of human anti-hepatitis B vaccine response. Vaccine. Dec. 16, 2004;23(5):615-22.
Singh et al., Cationic microparticles are an effective delivery system for immune stimulatory CpG DNA. Pharm Res. Oct. 2001;18(10):1476-9.
Sonehara et al., Hexamer palindromic oligonucleotides with 5'-Cg-3' motif(s) induce production of interferon. J Interferon Cytokine Res. Oct. 1996;16(10):799-803.
Sparwasser et al., Bacterial DNA causes septic shock. Nature. Mar. 27, 1997;386(6623):336-7.
Sparwasser et al., Bacterial DNA and immunostimulatory CpG oligonucleotides trigger maturation and activation of murine dendritic cells. Eur J Immunol. Jun. 1998;28(6):2045-54.
Sparwasser et al., Macrophages sense pathogens via DNA motifs: induction of tumor necrosis factor-alpha-mediated shock. Eur J Immunol. Jul. 1997;27(7):1671-9.
Stein et al., Problems in interpretation of data derived from in vitro and in vivo use of antisense oligodeoxynucleotides. Antisense Res Dev. 1994 Summer;4(2):67-9.
Stein et al., Non-antisense effects of oligodeoxynucleotides. Antisense Technology. 1997; Ch.11: 241-64.
Stein et al., Antisense oligonucleotides as therapeutic agents—is the bullet really magical? Science. Aug. 20, 1993;261(5124):1004-12.
Stevceva et al., Mucosal HIV vaccines: where are we now? Curr HIV Res. Jan. 2004;2(1):1-10.
Sun et al. Type I interferon-mediated stimulation of T cells by CpG DNA. J Exp Med. Dec. 21, 1998;188(12):2335-42.
Sun et al. Multiple effects of immunostimulatory DNA on T cells and the role of type I interferons. Springer Semin Immunopathol. 2000;22(1-2):77-84.
Tacket et al., Phase 1 safety and immune response studies of a DNA vaccine encoding hepatitis B surface antigen delivered by a gene delivery device. Vaccine. Jul. 16, 1999;17(22):2826-9.
Tokunaga et al., Synthetic oligonucleotides with particular base sequences from the cDNA encoding proteins of Mycobacterium bovis BCG induce interferons and activate natural killer cells Microbiol Immunol. 1992;36(1):55-66.
Tokunaga, Response of the organism to DNA—With a focus on immunostimulatory DNA. Kansen Ensho Meneki. 2001 Autumn; 31(3): 1-12. Japanese.
Uhlmann et al., Recent advances in the development of immunostimulatory oligonucleotides. Curr Opin Drug Discov Devel. Mar. 2003;6(2):204-17.
Verthelyi et al., CpG oligodeoxynucleotides improve the response to hepatitis B immunization in healthy and SIV-infected rhesus macaques. AIDS. Apr. 30, 2004;18(7):1003-8.
Verthelyi et al., Human peripheral blood cells differentially recognize and respond to two distinct CPG motifs. J Immunol. Feb. 15, 2001;166(4):2372-7.
Vollmer et al., Highly immunostimulatory CpG-free oligodeoxynucleotides for activation of human leukocytes. Antisense Nucleic Acid Drug Dev. Jun. 2002;12(3):165-75.
Vollmer et al., Immunopharmacology of CpG oligodeoxynucleotides and ribavirin. Antimicrob Agents Chemother. Jun. 2004;48(6):2314-7.
Vollmer et al., Characterization of three CpG oligodeoxynucleotide classes with distinct immunostimulatory activities. Eur J Immunol. Jan. 2004;34(1):251-62.
Vollmer et al., Modulation of CpG oligodeoxynucleotide-mediated immune stimulation by locked nucleic acid (LNA). Oligonucleotides. 2004 Spring;14(1):23-31.
Vollmer et al., Identification of a new class of CpG oligonucleotides capable of inducing both B cell proliferation and high IFN-alpha secretion from PBMC of HCV chronic carriers. Antivir Ther 2002; 7:L115.
Vollmer, TLR9 in health and disease. Int Rev Immunol. May-Aug. 2006;25(3-4):155-81.
Wagner, Interactions between bacterial CpG-DNA and TLR9 bridge innate and adaptive immunity. Curr Opin Microbiol. Feb. 2002;5(1):62-9.
Wang et al., CpG oligonucleotides partially inhibit growth of Mycobacterium tuberculosis, but not Salmonella or Listeria, in human monocyte-derived macrophages. FEMS Immunol Med Microbiol. Aug. 1, 2005;45(2):303-10.
Warren et al., APC stimulated by CpG oligodeoxynucleotide enhance activation of MHC class I-restricted T cells. J Immunol. Dec. 1, 2000;165(11):6244-51.
Weeratna et al., Reduction of antigen expression from DNA vaccines by coadministered oligodeoxynucleotides. Antisense Nucleic Acid Drug Dev. Aug. 1998;8(4):351-6.
Weeratna et al., Cpg ODN allows lower dose of antigen against hepatitis B surface antigen in BALB/c mice. Immunol Cell Biol. Feb. 2003;81(1):59-62.
Weeratna et al., CpG ODN can re-direct the Th bias of established Th2 immune responses in adult and young mice. FEMS Immunol Med Microbiol. Dec. 2001;32(1):65-71.
Weeratna et al., CpG DNA induces stronger immune responses with less toxicity than other adjuvants. Vaccine. Mar. 6, 2000;18(17):1755-62.
Weeratna et al., Priming of immune responses to hepatitis B surface antigen in young mice immunized in the presence of maternally derived antibodies. FEMS Immunol Med Microbiol. Apr. 2001;30(3):241-7.
Weighardt et al., Increased resistance against acute polymicrobial sepsis in mice challenged with immunostimulatory CpG oligodeoxynucleotides is related to an enhanced innate effector cell response. J Immunol. Oct. 15, 2000;165(8):4537-43.
Weiner et al., The immunobiology and clinical potential of immunostimulatory CpG oligodeoxynucleotides. J Leukoc Biol. Oct. 2000;68(4):455-63.
Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.
Yamamoto et al., Unique palindromic sequences in synthetic oligonucleotides are required to induce IFN [correction of INF] and augment IFN-mediated [correction of INF] natural killer activity. J Immunol. Jun. 15, 1992;148(12):4072-6.
Yamamoto et al., [Commemorative lecture of receiving Imamura Memorial Prize. II. Mode of action of oligonucleotide fraction extracted from Mycobacterium bovis BCG] Kekkaku. Sep. 1994;69(9):571-4. Japanese.
Yamamoto et al., Ability of oligonucleotides with certain palindromes to induce interferon production and augment natural killer cell activity is associated with their base length. Antisense Res Dev. 1994 Summer;4(2):119-22.
Yamamoto et al., Synthetic oligonucleotides with certain palindromes stimulate interferon production of human peripheral blood lymphocytes in vitro. Jpn J Cancer Res. Aug. 1994;85(8):775-9.
Yi et al., Rapid induction of mitogen-activated protein kinases by immune stimulatory CpG DNA. J Immunol. Nov. 1, 1998;161(9):4493-7.

Yi et al., Rapid immune activation by CpG motifs in bacterial DNA. Systemic induction of IL-6 transcription through an antioxidant-sensitive pathway. J Immunol. Dec. 15, 1996;157(12):5394-402.

Yi et al., IFN-gamma promotes IL-6 and IgM secretion in response to CpG motifs in bacterial DNA and oligodeoxynucleotides. J Immunol. Jan. 15, 1996;156(2):558-64.

Yi et al., CpG oligodeoxyribonucleotides rescue mature spleen B cells from spontaneous apoptosis and promote cell cycle entry. J Immunol. Jun. 15, 1998;160(12):5898-906.

Yi et al., CpG DNA rescue of murine B lymphoma cells from anti-IgM-induced growth arrest and programmed cell death is associated with increased expression of c-myc and bcl-xL. J Immunol. Dec. 1, 1996;157(11):4918-25.

Yu et al., Accessible 5'-end of CpG-containing phosphorothioate oligodeoxynucleotides is essential for immunostimulatory activity. Bioorg Med Chem Lett. Dec. 4, 2000;10(23):2585-8.

Zelphati et al., Inhibition of HIV-1 replication in cultured cells with antisense oligonucleotides encapsulated in immunoliposomes. Antisense Res Dev. 1993 Winter;3(4):323-38. Abstract only.

Zhang et al., Antisense oligonucleotide inhibition of hepatitis C virus (HCV) gene expression in livers of mice infected with an HCV-vaccinia virus recombinant. Antimicrob Agents Chemother. Feb. 1999;43(2):347-53.

Zhao et al., Pattern and kinetics of cytokine production following administration of phosphorothioate oligonucleotides in mice. Antisense Nucleic Acid Drug Dev. Oct. 1997;7(5):495-502.

Zhu et al., Modulation of ovalbumin-induced Th2 responses by second-generation immunomodulatory oligonucleotides in mice. Int Immunopharmacol. Jul. 2004;4(7):851-62.

Zimmermann et al., CpG oligodeoxynucleotides trigger protective and curative Th1 responses in lethal murine leishmaniasis. J Immunol. Apr. 15, 1998;160(8):3627-30.

Vollmer, Progress in drug development of immunostimulatory CpG oligodeoxynucleotide ligands for TLR9. Expert Opin Biol Ther. May 2005;5(5):673-82. Review.

* cited by examiner

METHODS AND PRODUCTS RELATED TO TREATMENT AND PREVENTION OF HEPATITIS C VIRUS INFECTION

RELATED APPLICATIONS

This application is a national stage filing under 35 U.S.C. §371 of PCT International application PCT/IB2003/005520, filed Oct. 29, 2003, which was published under PCT Article 21(2) in English, and which claims the benefit under 35 U.S.C. §119(e) of U.S. provisional application Ser. No. 60/421,987, filed Oct. 29, 2002, each of which is herein incorporated by reference in its entirety.

FIELD OF THE INVENTION

The invention provides methods and products for the treatment of subjects chronically infected with hepatitis C virus.

BACKGROUND OF THE INVENTION

The hepatitis C virus (HCV) is a positive strand RNA virus of the Flavivirus family that infects hepatocytes of humans and some other primates. First characterized in 1989 (1), HCV has a 9.5 kb genome that encodes for three structural proteins: core and two envelope glycoproteins (E1 and E2), as well as several non-structural (NS) proteins that are involved in the viral replication and interaction with the host cell (2).

HCV is a serious public health concern, causing >90% of parenteral non-A, non-B hepatitis (1). From 0.4 to 1.5% of the world's population is infected (3, 4), including about 300,000 Canadians (Health Canada). Epidemiological statistics are difficult to compile since the vast majority of acute infections are subclinical; however it is estimated that 50-80% of HCV infected individuals fail to clear the virus, and most of these become life-long carriers. About 50% of carriers develop chronic hepatitis and 20% of these will develop liver cirrhosis, many of whom will subsequently develop hepatocellular carcinoma (5-9). Hepatitis C causes an estimated 8,000 to 10,000 deaths annually in the United States (CDC).

In the United States and Canada, there are two different regimens, which have been approved as therapy for hepatitis C: monotherapy with alpha interferon and combination therapy with alpha interferon and Ribavirin. Although more expensive and associated with more side effects, combination therapy consistently yields higher rates of sustained response than monotherapy.

Several forms of alpha interferon are available (alpha-2a, alpha-2b, and consensus interferon (Alfacon)). These interferons are typically given subcutaneously three times weekly. Pegylated interferon, i.e., alpha interferon modified by addition of polyethylene glycol (PEG) in order to increase the duration in the circulation, is another of interferon, and it is given only once weekly. Ribavirin, in contrast, is an oral antiviral agent that is given twice a day in 200 mg capsules.

Side effects of alpha interferon include: fatigue, muscle aches, headaches, nausea and vomiting, skin irritation at the injection site, low-grade fever, weight loss, irritability, depression, suicide, mild bone marrow suppression and hair loss (reversible). For Ribavirin the side effects include; anemia fatigue and irritability, itching, skin rash, nasal stuffiness, sinusitis and cough.

Treatment with interferon alone or in combination with interferon and Ribavirin leads to rapid improvements in serum ALT levels in 50-75% of patients and the disappearance of detectable HCV RNA from the serum in 30-50% of patients. Long-term improvement in liver disease usually occurs only if HCV RNA disappears during therapy and stays undetectable for at least 6 months after therapy is completed. Combination treatment results in both a higher rate of loss of HCV RNA on treatment and a lower rate of relapse when treatment is complete. However, results depend strongly on the genotype of virus, with better results being obtained for genotypes 2 and 3 (about 90% with 1 year of treatment with pegylated IFN-α and Ribavirin), but much poorer results (about 40% sustained response) for genotype 1 HCV. The majority of HCV chronic carriers in North America now are of genotype 1.

The optimal duration of treatment varies depending on whether interferon monotherapy or combination therapy is used, as well as by HCV genotype. Typically, the duration ranges from 6 to 12 months.

There is currently no vaccine against HCV, or highly effective therapy for chronic infection. Thus there is an urgent need for an effective treatment that could be used to treat chronic carriers.

SUMMARY OF THE INVENTION

The invention is premised in part on several surprising findings including the observation that CpG immunostimulatory nucleic acids can be used to treat subjects that are chronically infected with hepatitis C virus (HCV) and that are non-responsive to previously administered non-CpG therapies. The invention is further premised in part on the observation that a synergistic response can be had in such subjects from the combined use of CpG immunostimulatory nucleic acids and an anti-viral agent such as IFN-alpha.

In one aspect, the invention provides a method of treating a subject having an HCV infection that was not successfully treated using a previous non-CpG therapy comprising administering to a subject in need of such treatment a CpG immunostimulatory nucleic acid in an amount effective to treat the infection.

In one embodiment, the non-CpG therapy includes interferon-alpha. In a related embodiment, the interferon-alpha is interferon-alpha-2b, interferon-alpha-2a or consensus interferon-alpha. In another embodiment, the non-CpG therapy includes interferon-alpha and Ribavirin, or interferon-alpha and Ribavirin and emantidine. In some important embodiments, the non-CpG therapy includes pegylated interferon-alpha and an anti-viral such as Ribavirin.

In one embodiment, the CpG immunostimulatory nucleic acid is an A class CpG immunostimulatory nucleic acid. In another embodiment, the CpG immunostimulatory nucleic acid is a B class CpG immunostimulatory nucleic acid.

In yet a further embodiment, the CpG immunostimulatory nucleic acid is a C class CpG immunostimulatory nucleic acid.

The method may optionally comprise administration of an anti-viral such as interferon-alpha to the subject along with the CpG immunostimulatory nucleic acid. The interferon-alpha may be interferon-alpha-2b, interferon-alpha-2a or consensus interferon alpha, but is not so limited. In one embodiment, the anti-viral is administered substantially simultaneously with the CpG immunostimulatory nucleic acid.

In one embodiment, the CpG immunostimulatory nucleic acid comprises a backbone modification. In a related embodiment, the backbone modification is a phosphorothioate backbone modification. In some important embodiment, the CpG immunostimulatory nucleic acid comprises a semi-soft backbone. In other important embodiments, the CpG immunostimulatory nucleic acid is a C class immunostimulatory nucleic acid having a semi-soft backbone.

Thus, in another aspect, a method is provided for treating a subject having an HCV infection that was not successfully treated using a previous non-CpG therapy comprising administering to a subject in need of such treatment a C class CpG immunostimulatory nucleic acid having a semi-soft backbone in an amount effective to treat the infection.

In yet another aspect, a method is provided for treating a subject having an HCV infection that was not successfully treated using a previous non-CpG therapy comprising contacting peripheral blood mononuclear cells from a subject in need of such treatment, with a CpG immunostimulatory nucleic acid in an amount effective to stimulate an immune response, and re-infusing the cells into the subject.

In one embodiment, the peripheral blood mononuclear cells comprise dendritic cells. In another embodiment, the dendritic cells comprise plasmacytoid dendritic cells. In one embodiment, the CpG immunostimulatory nucleic acid is a C class immunostimulatory nucleic acid. In a related embodiment, the C class immunostimulatory nucleic acid has a semi-soft backbone.

In another aspect, the invention provides a method of treating a subject having an HCV infection and likely to be non-responsive to a non-CpG therapy comprising administering to a subject in need of such treatment a CpG immunostimulatory nucleic acid in an amount effective to treat the infection.

In one embodiment, the method further comprises identifying a subject likely to be non-responsive to a non-CpG therapy. In one embodiment, the subject is identified as likely to be non-responsive based on an assay of interferon-alpha produced per dendritic cell. In another embodiment, the subject is identified as likely to be non-responsive based on HCV genotype.

In one embodiment, the non-CpG therapy includes IFN-αlpha. In a related embodiment, the non-CpG therapy includes interferon-alpha and Ribavirin.

In one embodiment, the method further comprises administering to the subject an anti-viral agent. In important embodiments, the anti-viral agent is interferon-alpha. The interferon-alpha may be interferon-alpha-2b, interferon-alpha-2a or consensus interferon alpha, but it is not so limited. In one embodiment, the interferon-alpha is administered in a sub-therapeutic amount, and optionally the combination of the CpG immunostimulatory nucleic acid and the interferon-alpha is synergistic.

In one embodiment, the CpG immunostimulatory nucleic acid used to treat the subject is an A class CpG immunostimulatory nucleic acid, a B class CpG immunostimulatory nucleic acid, or a C class CpG immunostimulatory nucleic acid.

In one embodiment, the CpG immunostimulatory nucleic acid used to identify whether a subject is likely to be non-responsive to a non-CpG therapy is an A class CpG immunostimulatory nucleic acid, or a C class CpG immunostimulatory nucleic acid.

In one embodiment, the anti-viral agent is administered to the subject substantially simultaneously with the CpG immunostimulatory nucleic acid. In other embodiments, the interferon-alpha is administered for a period prior to treatment with the CpG immunostimulatory nucleic acid.

In certain embodiments, the CpG immunostimulatory nucleic acid comprises a backbone modification. In related embodiments, the backbone modification is a phosphorothioate backbone modification. In some preferred embodiments, the CpG immunostimulatory nucleic acid comprises a semi-soft backbone, and some even more preferred embodiments, the CpG immunostimulatory nucleic acid is a C class CpG immunostimulatory nucleic acid having a semi-soft backbone.

In another aspect, a method is provided for treating a subject having an HCV infection and likely to be non-responsive to a non-CpG therapy comprising administering to a subject in need of such treatment a C class CpG immunostimulatory nucleic acid having a semi-soft backbone in an amount effective to treat the infection.

In yet another aspect, the invention provides a method for screening CpG immunostimulatory nucleic acids useful in the treatment of chronic hepatitis C viral infection. The method involves contacting peripheral blood mononuclear cells from a subject having a chronic hepatitis C viral infection, to a CpG immunostimulatory nucleic acid, and measuring a test response of the blood mononuclear cells after exposure. The subject from which the peripheral blood mononuclear cells wherein the subject was not successfully treated using a previous therapy.

In one embodiment, the test response is selected from the group consisting of B cell stimulation, secretion of IL-6, secretion of IL-10, secretion of IL-12, secretion of interferon-gamma, secretion of type 1 interferons (alpha+beta), secretion of IP-10, NK activity, expression of CD80, expression of CD 86, expression of CD83, and upregulation of class II MHC expression.

In another embodiment, the peripheral blood mononuclear cells comprise dendritic cells. In a related embodiment, the dendritic cells comprise plasmacytoid dendritic cells. In still another embodiment, the cells are dendritic cells and the test response is selected from the group consisting of secretion of IL-12, secretion of type 1 interferons, expression of CD80, expression of CD 86, expression of CD83, and upregulation of class II MHC expression.

In one embodiment, the contacting occurs in vitro. In another embodiment, the peripheral blood mononuclear cells are cultured. In yet another embodiment, the CpG immunostimulatory nucleic acid is added to the cultured peripheral blood mononuclear cells.

In one embodiment, the previous therapy is a non-CpG therapy. In another embodiment, the non-CpG therapy comprises interferon-alpha. In another embodiment, the non-CpG therapy further comprises Ribavirin. In other embodiments, the interferon-alpha is pegylated interferon-alpha. In one embodiment, the previous therapy is therapy with a CpG nucleic acid of a different sequence or class.

In other embodiments, the method further comprises screening the CpG immunostimulatory nucleic acid for the ability to stimulate a control response from peripheral blood mononuclear cells from a normal subject.

The method may further comprise contacting peripheral blood mononuclear cells to interferon-alpha substantially simultaneously with the CpG immunostimulatory nucleic acid.

In one embodiment, the CpG immunostimulatory nucleic acid comprises a backbone modification. In a related embodiment, the backbone modification is a phosphorothioate backbone modification. In important embodiments, the CpG immunostimulatory nucleic acid comprises a semi-soft backbone. The CpG immunostimulatory nucleic acid may be an A class CpG immunostimulatory nucleic acid, a B class CpG immunostimulatory nucleic acid, or a C class CpG immunostimulatory nucleic acid. In some embodiments, the CpG immunostimulatory nucleic acid is a C class immunostimulatory nucleic acid, and in other embodiments, the CpG immunostimulatory nucleic acid is a C class immunostimulatory nucleic acid with a semi-soft backbone.

In another aspect, the invention provides a method for identifying a subject having an HCV infection and likely to be non-responsive to a non-CpG therapy. The method involves exposing peripheral blood mononuclear cells harvested from a subject having a hepatitis C viral infection to a CpG immunostimulatory nucleic acid, measuring interferon-alpha produced from the cells, and determining an amount of interferon-alpha produced per dendritic cell, wherein an amount that is below 1.0 pg/ml is indicative of a subject that is likely to be non-responsive to a non-CpG therapy. In one embodiment, an amount that is below 0.5 pg/ml is indicative of a subject that is likely to be non-responsive to a non-CpG therapy.

In one embodiment, the non-CpG therapy comprises interferon-alpha. In another embodiment, the non-CpG therapy comprises Ribavirin. In another embodiment, the IFN-alpha is pegylated IFN-alpha.

In some important embodiments, the CpG immunostimulatory nucleic acid is an A class or a C class CpG immunostimulatory nucleic acid.

In still other embodiments, the peripheral blood mononuclear cells are further exposed to an anti-viral agent together with a CpG immunostimulatory nucleic acid. The anti-viral agent may be interferon-alpha, but it is not so limited. In one embodiment, the interferon-alpha is interferon-alpha-2b, interferon-alpha-2a or consensus interferon alpha.

In one embodiment, the peripheral blood mononuclear cells comprise dendritic cells. In another embodiment, the dendritic cells comprise plasmacytoid dendritic cells.

In another embodiment, the hepatitis C viral infection is an acute hepatitis C viral infection.

In another embodiment, the method further comprises determining a genotype of the HCV.

In still a further aspect, a method is provided for identifying a subject having an HCV infection and likely to be non-responsive to a non-CpG therapy comprising exposing peripheral blood mononuclear cells harvested from a subject having a hepatitis C viral infection to an A class or a C class CpG immunostimulatory nucleic acid, measuring interferon-alpha produced from the cells, and determining an amount of interferon-alpha produced per dendritic cell, wherein an amount that is below 1.0 pg/ml is indicative of a subject that is likely to be non-responsive to a non-CpG therapy.

In yet another aspect, the invention provides a method of treating a subject having a hepatitis C viral infection comprising administering to a subject, identified according to the method described above, a CpG immunostimulatory nucleic acid molecule in an amount effective to treat the infection.

In one embodiment, the method further comprises administering to the subject interferon-alpha. In one embodiment, the interferon-alpha is interferon-alpha-2b, interferon-alpha-2a or consensus interferon-alpha.

In one embodiment, the CpG immunostimulatory nucleic acid used to treat the subject is an A class CpG immunostimulatory nucleic acid, a B class CpG immunostimulatory nucleic acid, or a C class CpG immunostimulatory nucleic acid.

In another embodiment, the CpG immunostimulatory nucleic acid comprises a backbone modification. In a related embodiment, the backbone modification is a phosphorothioate backbone modification. In yet another embodiment, the CpG immunostimulatory nucleic acid comprises a semi-soft backbone.

In one embodiment, the hepatitis C viral infection is a chronic hepatitis C viral infection. In another embodiment, the hepatitis C viral infection is an acute hepatitis C viral infection.

Each of the limitations of the invention can encompass various embodiments, of the invention. It is, therefore, anticipated that each of the limitations of the invention involving any one element or combinations of elements can be included in each aspect of the invention.

These and other aspects of the invention are described in greater detail below.

Figure 1:
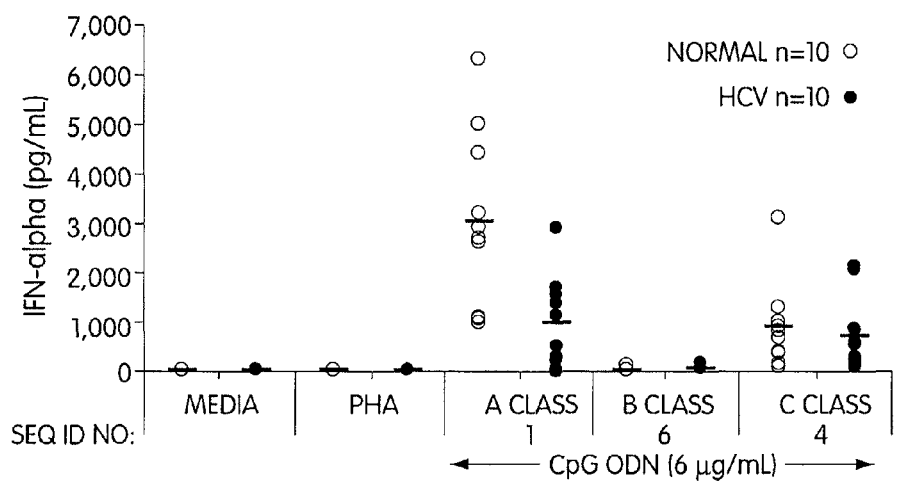
FIG. 1 shows the induction of IFN-α secretion from HCV-infected and normal PBMCs following stimulation with 3 classes of CpG. PBMCs from normal or HCV-infected subjects were incubated with different classes of CpG for 48 h. Cell supernatants were collected and assayed for IFN-α secretion by commercial ELISA kits. The average IFN-α secretion for 10 normal subjects and 10 HCV-infected subjects are shown by the black bars.
Figure 2:
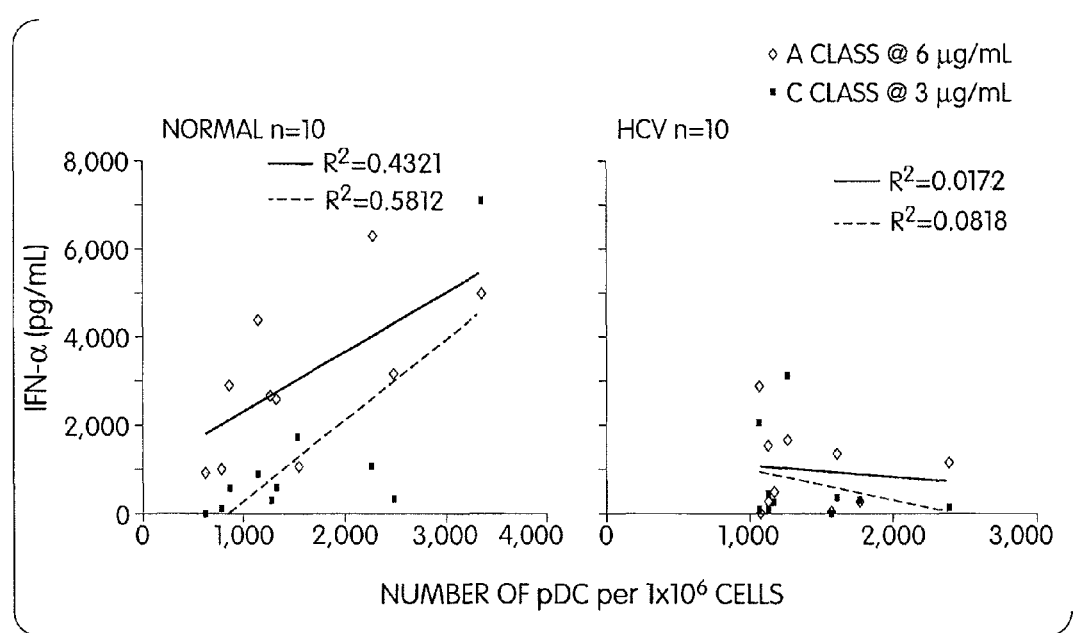
FIG. 2 shows the flow cytometric analysis of freshly isolated PBMCs from chronic HCV carriers and normal subjects. PBMCs were isolated from the blood of HCV infected subjects and from normal healthy donors and immunostained with fluorescent-tagged anti-plasmacytoid dendritic cell (pDC) antibodies. Cells were analyzed on a flow cytometer and results were compared to IFN-α secretion data on these same subjects when stimulated with CpG.

It is to be understood that the figures are not required for enablement of the claimed invention.

DETAILED DESCRIPTION OF THE INVENTION

It has been discovered according to the invention, that CpG oligonucleotides can activate PBMCs from patients chronically infected with HCV, including those who have failed previous interferon-alpha (IFN-α) therapy, in a manner similar to PBMCs from healthy subjects.

It was discovered that endogenous IFN-α secretion was strongly induced from plasmacytoid dendritic cells (PDC), which are thought to be infected by HCV resulting in their dysfunction and reduced ability to respond to other stimuli. In some instances, the A and C CpG classes, which induce high levels of IFN-α in PBMCs from healthy volunteers, were found to induce the highest levels of IFN-α from pDCs. It was further discovered that the semi-soft C class CpG ODN are also particularly useful for this effect. These ODN may be preferred in some embodiments since they will not accumulate in the kidney with repeat dosing.

It has been further discovered according to the invention that neither exogenous IFN-α (Intron A) nor Ribavirin have any detectable direct immune stimulatory effects on PBMCs from normal subjects or HCV chronic carriers, when used alone or together. However, when Intron A and CpG ODN (e.g., B or C classes) are used together, then a strong synergy for production of endogenous IFN-α is observed.

These results indicate that CpG ODN are an effective treatment alone, or together with IFN-α, to treat chronic HCV infection. The invention provides methods and products for preventing and treating HCV infection, based on these findings.

Chronic infection appears to be due, at least in part, to the rapid mutation rate of HCV, resulting in the production of quasi-species that can escape immune surveillance (10, 11). Both humoral and cell-mediated immune (CMI) responses can be detected in chronically infected individuals. While neutralizing antibodies are critical to protection from infection, cell-mediated immunity (CMI) appears to play the major role in viral clearance once infection is established.

In one aspect, the invention provides a method of treating a subject infected with hepatitis C virus (HCV) who is not successfully treated with a previous non-CpG therapy. The method comprises administering to a non-responsive subject in need of such treatment a CpG immunostimulatory nucleic acid in an amount effective to inhibit the infection.

A non-CpG therapy, as used herein, is a therapy that uses active or inactive compounds that are not CpG immunostimulatory nucleic acids. In various embodiments, the non-CpG therapy includes interferon-alpha. Pegylated IFN-αlpha is commonly administered to HCV subjects (e.g., human HCV patients), preferably in combination with Ribavirin and optionally amantadine. The interferon-alpha can be interferon-alpha-2b, interferon-alpha-2a or consensus interferon-alpha. All of the foregoing interferon-alpha treatments are included in the definition of non-CpG therapy.

A subject who is not successfully treated with a previous non-CpG therapy is a subject who notwithstanding prior treatment still has detectable viral load in their bloodstream 6 months after the cessation of therapy. These subjects include those that may respond to a previous non-CpG therapy, but who fail to control the infection and subsequently relapse as indicated by detectable viral load. As used herein and for the sake of simplicity, these subjects are referred to as "non-responders", however this term is to be understood as defined herein, and not as defined in a clinical setting. In other words, although in a clinical setting a "non-responder" defines only that narrow subset of subjects that fail to show any response to a treatment, the invention is directed to a broader category of subjects that while perhaps responding at some level to a previous treatment, are still not successfully treated. A subject that is successfully treated is one that has no detectable viral load in its bloodstream 6 months after the cessation of treatment. Successful treatment means treatment that leads to an undetectable level of viral load in the bloodstream that is sustained for at least 6 months after cessation of treatment. It is to be understood that a non-responder, as used herein, implicitly is also chronically infected with HCV.

As used herein, when referring to treatment using CpG nucleic acids, the methods are used to achieve a successful treatment of subjects. Successful treatment of subjects using CpG treatment is defined as a reduction of viral load to undetectable levels in the bloodstream 6 months after the cessation of therapy. Interestingly, viral loads may not be observed to decrease during or immediately after CpG treatment, but rather may only decrease with time after treatment, with the ultimate result that there is no detectable virus in the bloodstream of these subjects 6 months following the cessation of treatment. To treat an infection therefore means to reduce viral load to an undetectable level in the bloodstream of a subject and to sustain that level for 6 months following the cessation of treatment. Effective amounts of agents are therefore administered to achieve this end result.

In some embodiments, the potential non-responders may be identified prospectively (i.e., prior to actual in vivo treatment with a non-CpG therapy), and the invention provides methods not only for the identification of such subjects but also for their treatment. Potential non-responders may be identified by assessing their ability to respond to CpG immunostimulatory nucleic acids, particularly A class and C class. The ability to respond to CpG immunostimulatory nucleic acids will be assessed by the amount of interferon-alpha that is produced per pDC in HCV infected subjects. It was discovered, according to the invention, that HCV infected subjects that would be unlikely to respond to non-CpG therapy such as IFN-alpha therapy could be identified prior to receiving such treatment. The ability to identify such subjects prior to in vivo therapy eliminates unnecessary treatment and places the subjects in a therapeutically advantageous position for treatment with the CpG immunostimulatory nucleic acids of the invention either alone or in combination with other anti-HCV therapies including but not limited to IFN-alpha. These subjects would suffer from less cytotoxicity and the time period for viral growth would be reduced by not undergoing a treatment that will be unsuccessful. Subjects having below a reasonable level of IFN-alpha induction per pDC are likely not to be successfully treated with IFN-alpha and thus should be treated using the methods provided herein. Measurement of IFN-alpha induction and pDC numbers are described in more detail in the Examples.

It is to be understood that an HCV infected subject that is successfully treated with any of the therapeutic agents and methods discussed herein will probably still have virus in their body. However, while the subject is not able to completely eradicate the virus, it is able to control viral load (to undetectable levels). Although not intending to be bound by any particular theory, it is expected that the maintenance of undetectable viral loads in such subjects involve an immune system that is able to control viral replication and spread.

One of ordinary skill given the teachings provided herein will be able to determine whether a subject is likely to be a "non-responder" to IFN-alpha therapy. As an example, if the IFN-alpha induction were performed with an A class nucleic acid such as nucleic acid designated SEQ ID NO 1, under the culture conditions described in the Examples, a normal response indicative of the ability to respond to IFN-alpha therapy would be at least 1 pg/ml per pDC. An amount less than this is indicative of some pDC dysfunction. Amounts that are less than 0.5 pg/ml per pDC correlate with a higher probability of non-response to IFN-alpha treatment. One of ordinary skill will be able to determine such cutoffs for the particular type of nucleic acid used in the assay, and will therefore be capable of identifying subjects expected not to be successfully treated with IFN-alpha therapy (at least) prior to actually treating such subjects in that manner.

In still other embodiments, the method of identifying a subject who is likely to be a non-responder to non-CpG therapy (e.g., IFN-alpha therapy) may further include identification of the genotype of HCV he/she is infected with. It is more likely that a subject infected with a genotype 1 HCV will not be successfully treated with IFN-αlpha therapy, for example. Therefore, in addition to assessing the production of IFN-αlpha per DC in such subjects, their HCV genotype can also be determined (using methods known in the art), and this combination of information can be used to identify a subject that is likely to be non-responsive to IFN-alpha therapy.

It is to be further understood that in some aspects, the invention provides a method for identifying a subject that is unlikely to be successfully treated using a non-CpG therapy (without actually treating the subject with a non-CpG therapy) and then treating the subject using either CpG immunostimulatory nucleic acids alone or in combination with an anti-viral agent such as but not limited to IFN-αlpha The above methods can also be used to screen subjects for their response to particular CpG immunostimulatory nucleic acids.

In still other embodiments, the methods may involve the additional step of identifying subjects having received previous non-CpG therapy but not successfully treated. Those of ordinary skill, given the teachings provided herein, will be able to identify such subjects. As an example, such subjects would have detectable viral loads in their bloodstream 6 months after the cessation of treatment. In some embodiments, these subjects may also demonstrate a reduction in viral load immediately following treatment, but this reduction is not sustained.

The invention intends to treat subjects not successfully treated with a previous non-CpG therapy using, inter alia, CpG immunostimulatory nucleic acids alone or in combination with other active agents such as those previously described for HCV infection. As broadly defined, CpG immunostimulatory nucleic acids are nucleic acids having at least one CpG dinucleotide motif in which at least the C of the dinucleotide is unmethylated. CpG immunostimulatory nucleic acids include but are not limited to A class, B class and C class CpG immunostimulatory nucleic acids, as described more fully herein and in the patent and patent applications cited herein and incorporated by reference. These classes of CpG immunostimulatory nucleic acid have differing properties and activation profiles.

In important embodiments, the CpG immunostimulatory nucleic acid is a C class immunostimulatory nucleic acid. It was surprisingly found, according to the invention, that C class immunostimulatory nucleic acids were preferred in some embodiments, even though these nucleic acids possessed properties intermediate to those of A class and B class. The Examples provided herein demonstrate that, even though pDC of chronically infected subjects not successfully treated with a previous non-CpG therapy are themselves infected with HCV and thereby dysfunctional in some aspects, exposure of such cells to CpG immunostimulatory nucleic acids, and in particular C class immunostimulatory nucleic acids, restores their function. In some embodiments, it is also preferred that the C class immunostimulatory nucleic acids be either of a "soft" or "semi-soft" variety, as described in greater detail herein. In some preferred embodiments, the CpG immunostimulatory is a semi-soft C class nucleic acid.

In other aspects, the CpG immunostimulatory nucleic acids are used in combination with active agents which preferably include those previously described for HCV treatment. Of particular importance is the use of CpG immunostimulatory nucleic acids with interferon-α (e.g., Intron A). The interferons that can be used in combination with the CpG immunostimulatory nucleic acids of the invention include but are not limited to interferon-alpha-2b, interferon-alpha-2a or consensus interferon alpha. Other anti-virals are described herein. Any of the CpG classes can be used in these combinations. As an example, it was unexpectedly found, according to the invention, that although exogenously administered interferon-α fails to treat these subjects successfully, when combined with CpG immunostimulatory nucleic acids it is therapeutically efficacious. In some embodiments, the CpG immunostimulatory nucleic acid is a C class immunostimulatory nucleic acid. In come preferred embodiments, it is a semi-soft C class nucleic acid.

The timing of administration of the CpG nucleic acid and anti-viral agent (e.g., interferon-alpha) may vary depending upon the subject and the severity of infection. The CpG nucleic acid may be administered substantially simultaneously with the CpG immunostimulatory nucleic acid. This means that the two agents may be combined prior to administration, or may be combined in the process of administration (e.g., with both feeding into an intravenous line in a subject), or they may be administered separately but within a period of time that it would take someone to perform two administrations (e.g., the time to inject a subject twice). Regardless of whether the agents are administered substantially simultaneously or in staggered fashion, the order may vary. Accordingly, in some embodiments, the CpG immunostimulatory nucleic acid may be administered prior to an anti-viral agent such as IFN-alpha while in others it may be administered following the anti-viral agent.

When CpG nucleic acids are used together with other anti-virals (e.g., IFN-αlpha), these compounds may be administered in a combined amount that is therapeutically efficacious. The amount of either compound may therefore be sub-therapeutic or supra-therapeutic (i.e., below or above the amount that would be therapeutically efficacious when administered alone). Alternatively, the compounds each may be administered in a therapeutic amount, but the combination of those agents creates a therapeutic benefit such as a reduction of side effects. In preferred embodiments, if the anti-viral is IFN-αlpha, it is administered in a therapeutic amount. Regardless of the actual amounts administered, the combination of agents may be synergistic. A synergistic response is one that is greater than the additive response expected by the combination of the agents.

In still other aspects and in keeping with the description provided above, the invention provides methods for screening CpG nucleic acids for the ability to stimulate immune cells isolated from a subject chronically infected with HCV and not successfully treated with a non-CpG therapy or likely to be non-responders to non-CpG therapy. These screening methods are generally performed in vitro by contacting peripheral blood mononuclear cells (PBMCs) with a CpG immunostimulatory nucleic acid in an effective amount sufficient to stimulate an immune response. The immune response can be measured by any number of markers, including IFN-alpha production, B cell stimulation, secretion of cytokines such as Il-6, IL-10, IL-12, interferon-gamma, type 1 interferons (alpha+beta), chemokine secretion such as IP-10, NK activity, expression of costimulatory molecules (e.g., CD80, CD 86) and maturation molecules (e.g., CD83) and upregulation of class II MHC expression.

In some important embodiments, the immune cells are dendritic cells, and preferably plasmacytoid dendritic cells (pDCs) and the immune response markers are specific to this cell type. These include but are not limited to expression of costimulatory molecules (e.g., CD80 and CD86) expression of maturation molecules (e.g., CD83), expression and/or secretion of IL-12 and type 1 interferons (alpha+beta), and upregulation of class II MHC expression. It is to be understood that these in vitro assays are not dependent upon isolation of dendritic cells such as pDCs from the remainder of PBMCs. Rather the assays can be carried out in homogeneous populations of PBMCs.

In still another aspect, the invention provides a method for identifying a subject having a chronic hepatitis C viral infection to be treated with a CpG immunostimulatory nucleic acid. The method involves exposing peripheral blood mononuclear cells harvested from a subject having a chronic hepatitis C viral infection to i) a CpG immunostimulatory nucleic acid, and ii) a CpG immunostimulatory nucleic acid and an anti-viral (e.g., interferon-alpha), and measuring response of the peripheral blood mononuclear cells after exposure. A response to a CpG immunostimulatory nucleic acid is indicative of a subject to be treated with a CpG immunostimulatory nucleic acid either following or in place of a non-CpG therapy (as described above, but only after identifying a subject that is unlikely to respond to a non-CpG therapy). A response to a CpG immunostimulatory nucleic acid together with an anti-viral agent (e.g., interferon-alpha) that is greater than the response to CpG immunostimulatory nucleic acid alone is indicative of a subject to be treated with the combination. As described herein, the anti-viral agent can be an interferon-alpha including but not limited to interferon-alpha-2b, interferon-alpha-2a or consensus interferon-alpha. Preferably, the peripheral blood mononuclear cells comprise dendritic cells such as plasmacytoid dendritic cells. The invention further includes treatment of subjects identified as just described using either CpG immunostimulatory nucleic acids alone or in combination with an anti-viral agent (e.g., IFN-alpha), depending upon the outcome of the screening assay.

Clinical strategies comprise local and systemic in vivo administration of such nucleic acids, as well as ex vivo strategies in which pDCs isolated from non-responsive HCV infected subjects are activated in vitro with immunostimulatory nucleic acids and then reinfused into the patient locally or systemically. These therapeutic strategies may include the combination with other growth factors (IL-3, GM-CSF, flt3-ligand, etc.) as well as with other stimuli (superantigens, viral products). Since natural IFN-α is a family of more than a dozen separate gene products, the individual products of which have unique activity profiles, the clinical use of natural interferon may be preferable compared to recombinant IFN-α derived from a single recombinant IFN-α gene.

The invention further provides a method activating pDCs from an Hepatitis C infected subject. The method involves isolating pDCs from the subject in need of such treatment, culturing the isolated pDCs in vitro, contacting the pDCs in vitro with an effective amount of an isolated immunostimulatory nucleic acid, and returning the contacted cells to the subject. The cells can also be contacted in vitro with a growth factor or with a cytokine. The immunostimulatory nucleic acids and conditions calling for treatment with IFN-α according to this aspect of the invention are as described above.

IFN-alpha itself represents a family of more than a dozen related, homologous proteins (isoforms, see Table 1 below), each encoded by a unique gene and each exhibiting a unique activity profile. The activities of the different alpha-interferon species on viruses can vary as much as twenty-fold or more. IFN-alpha products in clinical use are recombinant proteins or highly purified natural proteins of a single isoform. In the United States IFN-α is available as recombinant human IFN-α2a (ROFERON-A), recombinant human IFN-α2b (INTRON A), and as purified natural IFN-αn3 (ALFERON N). Outside the United States, IFN-α is also available as purified natural IFN-αn1 (WELLFERON).

TABLE 1

| Family of Human IFN-α | |
|---|---|
| IFN-αA | (IFN-α2a) |
| IFN-α2 | (IFN-α2b) |
| IFN-α4b | (IFN-α4) |
| IFN-αB2 | (IFN-α8) |
| IFN-αC | (IFN-α10) |
| IFN-αD | (IFN-α1) |
| IFN-αF | (IFN-α21) |

TABLE 1-continued

Family of Human IFN-α

| | |
|---|---|
| IFN-αG | (IFN-α5) |
| IFN-αH2 | (IFN-α14) |
| IFN-αI | (IFN-α17) |
| IFN-αJ1 | (IFN-α7) |
| IFN-αK | (IFN-α6) |
| IFN-αM1 | |
| IFN-αN | |
| IFN-αWA | (IFN-α16) |

Some of the methods of the invention require measurement of immune responses including detecting the presence of IFN-α. Assays for IFN-α are well known in the art. These include direct tests, e.g., enzyme-linked immunosorbent assay (ELISA) specific for at least one IFN-α, and indirect tests, e.g., functional tests including NK cell activation/cytotoxicity (Trinchieri G *Adv Immunol* 47:187-376 (1989) and phenotyping by fluorescence-activated cell sorting (FACS) analysis for class I MHC. Additional specific assay methods well known in the art can be particularly useful in settings where local concentration or local presence of IFN-α is of interest. These methods include, for example, immunohistochemistry, nucleic acid hybridization (e.g., Northern blotting), Western blotting, reverse transcriptase/polymerase chain reaction (RT/PCR), and in situ RT/PCR. Intracellular IFN-α can also be detected using flow cytometry.

The invention in some aspects involves measuring pDC activation. pDC activation can be assayed in a number of ways. These include IFN-α production, expression of costimulatory molecules (e.g., CD80 and CD86), expression of maturation molecules (e.g., CD83), expression of IL-12, and upregulation of class II MHC expression. Unlike administration of exogenous IFN-α, activation of pDC leads to the production of various if not all the forms of IFN-α, as well as other type I IFN such as IFN-β. In some embodiments, therefore, the pDC are activated as measured by their ability to produce type I interferons including IFN-α.

The invention provides various methods that involve immunostimulatory nucleic acids. An immunostimulatory nucleic acid is a nucleic acid molecule which, upon contacting cells of the immune system, is itself capable of inducing contacted cells of the immune system to proliferate and/or to become activated. The contacting can be direct or indirect, e.g., the immunostimulatory nucleic acid may directly stimulate a first type of immune cell to express a product which may in turn stimulate a second type of immune cell which has not been exposed to, or is not responsive to, the immunostimulatory nucleic acid. The immunostimulatory effect of the immunostimulatory nucleic acid is separate from any product that might happen to be encoded by the sequence of the immunostimulatory nucleic acid. Similarly, the immunostimulatory effect of an immunostimulatory nucleic acid is distinct from and does not rely upon any antisense mechanism.

Only certain nucleic acids are immunostimulatory nucleic acids. Originally it was believed that certain palindromic sequences were immunostimulatory. Tokunaga T et al. *Microbiol Immunol* 36:55-66 (1992); Yamamoto T et a. *Antisense Res Dev* 4:119-22 (1994). Further work demonstrated that non-palindromic sequences are also immunostimulatory provided they contained CpG dinucleotides within particular sequence contexts (CpG motifs). Krieg A M et al. *Nature* 374:546-9 (1995).

The immunostimulatory nucleic acids can be single-stranded or double-stranded. Generally, double-stranded nucleic acid molecules are more stable in vivo, while single-stranded nucleic acid molecules have increased immune activity. Thus in some aspects of the invention it is preferred that the immunostimulatory nucleic acid be single-stranded and in other aspects it is preferred that the immunostimulatory nucleic acid be double-stranded.

The methods and products provided in accordance with the invention relate to the use of CpG oligonucleotides. CpG ODN trigger most (>95%) B-cells to proliferate, secrete immunoglobulin (Ig), IL-6 and IL-12, and to be protected from apoptosis. In addition, CpG ODN cause DC maturation and also directly activate DCs, monocytes, and macrophages to secrete IFN-α/β, IL-6, IL-12, GM-CSF, chemokines and TNF-α. These cytokines stimulate natural killer (NK) cells to secrete IFN-γ and have increased lytic activity. Overall, CpG induces a strong Th1-like pattern of cytokine production dominated by IL-12 and IFN-γ with little secretion of Th2 cytokines.

In addition to induction of innate immune responses, CpG DNA also augments antigen-specific responses due to (i) a strong synergy between the B-cell signaling pathways triggered through the B-cell antigen receptor and by CpG, (ii) Th1-like cytokines that replace or augment antigen-specific T-help augmenting both B- and T-cell antigen-specific responses and (iii) up-regulation of co-stimulatory molecules that are required for cellular responses.

CpG ODN has been shown to be a potent adjuvant to HBsAg in BALB/c mice with clear Th1-like responses (predominantly IgG2a antibodies and strong CTL) (49). CpG ODN was found to be superior to other Th1 adjuvants such as monophosphoryl lipid A (MPL, Corixa) or even complete Freund's adjuvant (CFA) which is too toxic for human use. Similar results have been reported using CpG ODN with a variety of other antigens (47, 50-53). CpG ODN have also been reported to redirect a Th2 response previously established by immunization with a Th2 antigen (i.e., Schistosomiasis surface antigen) (54) or a Th2 adjuvant (i.e., alum).

There are at least three basic classes of CpG ODNs found to be effective at stimulating healthy human PBMCs (Table 1). These have differential effects that are likely associated with the different modes of by which CpG ODNs can stimulate immune cells.

The B class of CpG ODN are synthesized with nuclease resistant phosphorothioate backbones and are generally characterized by good B-cell and DC activation, leading to the production of IL-12 and antibody, but only limited NK cell activation. This class of ODN functions well as a vaccine adjuvant, as has already been demonstrated in a phase I/II clinical trial testing CpG (a member of this class) (SEQ ID NO.: 2) as an adjuvant to a commercial hepatitis B vaccine (60).

The A class of CpG ODNs are synthesized with a chimeric backbone where the 5' and 3' ends are phosphorothioate and the central CpG motif region is phosphodiester. These ODNs are characterized by good NK cell and DC activation leading to greater production of IFN-α but limited B-cell activation.

The C class of CpG ODN are synthesized with a phosphorothioate backbone and have stimulatory properties intermediate to the other two classes of CpG ODNs (e.g., good activation of B-cells as well as activation of NK cells and DCs).

TABLE 1

Pattern of in vitro immune activation induced by the three different classes of CpG ODNs

| Class | Backbone | B-cells | Natural Killer cells | Dendritic cells | IFN-α |
|---|---|---|---|---|---|
| A | SOS[2] | + | ++++ | ++++ | ++++ |
| B | S[1] | ++++ | ++ | ++++ | + |
| C | S[1] | +++ | +++ | +++ | +++ |

[1] S-ODN are made with a phosphorothioate backbone
[2] SOS-ODN are made with a chimeric backbone where the central CpG-containing region has phosphodiester linkages and the 3' and 5' ends of the ODN are made with phosphorothioate linkages The methods of the invention may embrace the use of A class, B class and C class CpG immunostimulatory nucleic acids. As to CpG nucleic acids, it has recently been described that there are different classes of CpG nucleic acids. One class is potent for activating B cells but is relatively weak in inducing IFN-α and NK cell activation; this class has been termed the B class. The B class CpG nucleic acids typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class is potent for inducing IFN-α and NK cell activation but is relatively weak at stimulating B cells; this class has been termed the A class. The A class CpG nucleic acids typically have stabilized poly-G sequences at 5' and 3' ends and a palindromic phosphodiester CpG dinucleotide-containing sequence of at least 6 nucleotides. See, for example, published patent application PCT/US00/26527 (WO 01/22990). Yet another class of CpG nucleic acids activates B cells and NK cells and induces IFN-α; this class has been termed the C-class. The C-class CpG nucleic acids, as first characterized, typically are fully stabilized, include a B class-type sequence and a GC-rich palindrome or near-palindrome. This class has been described in U.S. provisional patent application 60/313,273, filed Aug. 17, 2001, U.S. Ser. No. 10/224,523 filed on Aug. 19, 2002, and US the entire contents of which are incorporated herein by reference.

"A class" CpG immunostimulatory nucleic acids have been described in U.S. Non-Provisional patent application Ser. No. 09/672,126 and published PCT application PCT/US00/26527 (WO 01/22990), both filed on Sep. 27, 2000. These nucleic acids are characterized by the ability to induce high levels of interferon-alpha while having minimal effects on B cell activation. The A class CpG immunostimulatory nucleic acid do not necessarily contain a hexamer palindrome GACGTC, AGCGCT, or AACGTT described by Yamamoto and colleagues. Yamamoto S et al. *J Immunol* 148:4072-6 (1992).

Exemplary sequences of A class immunostimulatory nucleic acids are described in U.S. Non-Provisional patent application Ser. No. 09/672,126 and published PCT application PCT/US00/26527 (WO 01/22990), both filed on Sep. 27, 2000.

B class CpG immunostimulatory nucleic acids strongly activate human B cells but have minimal effects inducing interferon-α. B class CpG immunostimulatory nucleic acids have been described in U.S. Pat. No. 6,194,388 B1 and 6,239, 116 B1, issued on Feb. 27, 2001 and May 29, 2001 respectively.

The CpG oligonucleotides of the invention are oligonucleotides which include at least one unmethylated CpG dinucleotide. An oligonucleotide containing at least one unmethylated CpG dinucleotide is a nucleic acid molecule which contains an unmethylated cytosine-guanine dinucleotide sequence (i.e., "CpG DNA" or DNA containing a 5' cytosine followed by 3' guanine and linked by a phosphate bond) and activates the immune system. The entire CpG oligonucleotide can be unmethylated or portions may be unmethylated but at least the C of the 5'CG 3' must be unmethylated. The terms CpG oligonucleotide or CpG nucleic acid as used herein refer to an immunostimulatory CpG oligonucleotide or a nucleic acid unless otherwise indicated.

In one embodiment the invention provides a B class CpG oligonucleotide represented by at least the formula:

wherein $X_1$, $X_2$, $X_3$, and $X_4$ are nucleotides. In one embodiment $X_2$ is adenine, guanine, or thymine. In another embodiment $X_3$ is cytosine, adenine, or thymine.

In another embodiment the invention provides an isolated B class CpG oligonucleotide represented by at least the formula:

wherein $X_1$, $X_2$, $X_3$, and $X_4$ are nucleotides and N is any nucleotide and $N_1$ and $N_2$ are nucleic acid sequences composed of from about 0-25 N's each. In one embodiment $X_1X_2$ is a dinucleotide selected from the group consisting of: GpT, GpG, GpA, ApA, ApT, ApG, CpT, CpA, CpG, TpA, TpT, and TpG; and $X_3X_4$ is a dinucleotide selected from the group consisting of: TpT, ApT, TpG, ApG, CpG, TpC, ApC, CpC, TpA, ApA, and CpA. Preferably $X_1X_2$ is GpA or GpT and $X_3X_4$ is TpT. In other embodiments $X_1$ or $X_2$ or both are purines and $X_3$ or $X_4$ or both are pyrimidines or $X_1X_2$ is GpA and $X_3$ or $X_4$ or both are pyrimidines. In another preferred embodiment $X_1X_2$ is a dinucleotide selected from the group consisting of: TpA, ApA, ApC, ApG, and GpG. In yet another embodiment $X_3X_4$ is a dinucleotide selected from the group consisting of: TpT, TpA, TpG, ApA, ApG, GpA, and CpA. $X_1X_2$ in another embodiment is a dinucleotide selected from the group consisting of: TpT, TpG, ApT, GpC, CpC, CpT, TpC, GpT and CpG; $X_3$ is a nucleotide selected from the group consisting of A and T and $X_4$ is a nucleotide, but wherein when $X_1X_2$ is TpC, GpT, or CpG, $X_3X_4$ is not TpC, ApT or ApC.

In another preferred embodiment the CpG oligonucleotide has the sequence 5' $TCN_1TX_1X_2CGX_3X_4$ 3' (SEQ ID NO.: 26). The CpG oligonucleotides of the invention in some embodiments include $X_1X_2$ selected from the group consisting of GpT, GpG, GpA and ApA and $X_3X_4$ is selected from the group consisting of TpT, CpT and TpC.

The B class CpG nucleic acid sequences of the invention are those broadly described above as well as disclosed in PCT Published Patent Applications PCT/US95/01570 and PCT/US97/19791, and U.S. Pat. No. 6,194,388 B1 and U.S. Pat. No. 6,239,116 B1, issued Feb. 27, 2001 and May 29, 2001 respectively. Exemplary sequences include but are not limited to those disclosed in these latter applications and patents.

The C class immunostimulatory nucleic acids contain at least two distinct motifs have unique and desirable stimulatory effects on cells of the immune system.

Some of these ODN have both a traditional "stimulatory" CpG sequence and a "GC-rich" or "B-cell neutralizing" motif. These combination motif nucleic acids have immune stimulating effects that fall somewhere between those effects associated with traditional "class B" CpG ODN, which are strong inducers of B cell activation and dendritic cell (DC) activation, and those effects associated with a more recently described class of immune stimulatory nucleic acids ("class A" CpG ODN) which are strong inducers of IFN-α and natural killer (NK) cell activation but relatively poor inducers of B-cell and DC activation. Krieg A M et al. (1995) *Nature* 374:546-9; Ballas Z K et al. (1996) *J Immunol* 157:1840-5; Yamamoto S et al. (1992) *J Immunol* 148:4072-6. While preferred class B CpG ODN often have phosphorothioate backbones and preferred class A CpG ODN have mixed or chimeric backbones, the C class of combination motif immune stimulatory nucleic acids may have either stabilized, e.g., phosphorothioate, chimeric, or phosphodiester backbones, and in some preferred embodiments, they have semi-soft backbones.

In one aspect the invention provides immune stimulatory nucleic acids belonging to this new class of combination motif immune-stimulatory nucleic acids. The B cell stimulatory domain is defined by a formula: 5' $X_1$DCGH$X_2$ 3'. D is a nucleotide other than C. C is cytosine. G is guanine. H is a nucleotide other than G.

$X_1$ and $X_2$ are any nucleic acid sequence 0 to 10 nucleotides long. $X_1$ may include a CG, in which case there is preferably a T immediately preceding this CG. In some embodiments DCG is TCG. $X_1$ is preferably from 0 to 6 nucleotides in length. In some embodiments $X_2$ does not contain any poly G or poly A motifs. In other embodiments the immunostimulatory nucleic acid has a poly-T sequence at the 5' end or at the 3' end. As used herein, "poly-A" or "poly-T" shall refer to a stretch of four or more consecutive A's or T's respectively, e.g., 5' AAAA 3' or 5' TTTT 3'.

As used herein, "poly-G end" shall refer to a stretch of four or more consecutive G's, e.g., 5' GGGG 3', occurring at the 5' end or the 3' end of a nucleic acid. As used herein, "poly-G nucleic acid" shall refer to a nucleic acid having the formula 5' $X_1X_2$GGG$X_3X_4$ 3' wherein $X_1$, $X_2$, $X_3$, and $X_4$ are nucleotides and preferably at least one of $X_3$ and $X_4$ is a G.

Some preferred designs for the B cell stimulatory domain under this formula comprise TTTTTCG, TCG, TTCG, TTTCG, TTTTCG, TCGT, TTCGT, TTTCGT, TCGTCGT.

The second motif of the nucleic acid is referred to as either P or N and is positioned immediately 5' to $X_1$ or immediately 3' to $X_2$.

N is a B-cell neutralizing sequence that begins with a CGG trinucleotide and is at least 10 nucleotides long. A B-cell neutralizing motif includes at least one CpG sequence in which the CG is preceded by a C or followed by a G (Krieg A M et al. (1998) *Proc Natl Acad Sci USA* 95:12631-12636) or is a CG containing DNA sequence in which the C of the CG is methylated. As used herein, "CpG" shall refer to a 5' cytosine (C) followed by a 3' guanine (G) and linked by a phosphate bond. At least the C of the 5'CG 3' must be unmethylated. Neutralizing motifs are motifs which has some degree of immunostimulatory capability when present in an otherwise non-stimulatory motif, but, which when present in the context of other immunostimulatory motifs serve to reduce the immunostimulatory potential of the other motifs.

P is a GC-rich palindrome containing sequence at least 10 nucleotides long. As used herein, "palindrome" and, equivalently, "palindromic sequence" shall refer to an inverted repeat, i.e., a sequence such as ABCDEE'D° C.'B'A' in which A and A', B and B', etc., are bases capable of forming the usual Watson-Crick base pairs.

As used herein, "GC-rich palindrome" shall refer to a palindrome having a base composition of at least two-thirds G's and C's. In some embodiments the GC-rich domain is preferably 3' to the "B cell stimulatory domain". In the case of a 10-base long GC-rich palindrome, the palindrome thus contains at least 8 G's and C's. In the case of a 12-base long GC-rich palindrome, the palindrome also contains at least 8 G's and C's. In the case of a 14-mer GC-rich palindrome, at least ten bases of the palindrome are G's and C's. In some embodiments the GC-rich palindrome is made up exclusively of G's and C's.

In some embodiments the GC-rich palindrome has a base composition of at least 81 percent G's and C's. In the case of such a 10-base long GC-rich palindrome, the palindrome thus is made exclusively of G's and C's. In the case of such a 12-base long GC-rich palindrome, it is preferred that at least ten bases (83 percent) of the palindrome are G's and C's. In some preferred embodiments, a 12-base long GC-rich palindrome is made exclusively of G's and C's. In the case of a 14-mer GC-rich palindrome, at least twelve bases (86 percent) of the palindrome are G's and C's. In some preferred embodiments, a 14-base long GC-rich palindrome is made exclusively of G's and C's. The C's of a GC-rich palindrome can be unmethylated or they can be methylated.

In general this domain has at least 3 Cs and Gs, more preferably 4 of each, and most preferably 5 or more of each. The number of Cs and Gs in this domain need not be identical. It is preferred that the Cs and Gs are arranged so that they are able to form a self-complementary duplex, or palindrome, such as CCGCGCGG. This may be interrupted by As or Ts, but it is preferred that the self-complementarity is at least partially preserved as for example in the motifs CGACGT-TCGTCG (SEQ ID NO: 27) or CGGCGCCGTGCCG (SEQ ID NO: 28). When complementarity is not preserved, it is preferred that the non-complementary base pairs be TG. In a preferred embodiment there are no more than 3 consecutive bases that are not part of the palindrome, preferably no more than 2, and most preferably only 1. In some embodiments the GC-rich palindrome includes at least one CGG trimer, at least one CCG trimer, or at least one CGCG tetramer. In other embodiments the GC-rich palindrome is not CCCCCCGGGGGG (SEQ ID NO: 29) or GGGGGGC-CCCCC (SEQ ID NO: 30), CCCCCGGGGG (SEQ ID NO: 31) or GGGGGCCCCC (SEQ ID NO: 32).

At least one of the G's of the GC rich region may be substituted with an inosine (I). In some embodiments P includes more than one I.

In certain embodiments the immunostimulatory nucleic acid has one of the following formulas 5' N$X_1$DCGH$X_2$ 3', 5' $X_1$DCGH$X_2$N 3', 5' P$X_1$DCGH$X_2$ 3', 5' $X_1$DCGH$X_2$P 3', 5' $X_1$DCGH$X_2$P$X_3$ 3', 5' $X_1$DCGHP$X_3$ 3', 5' DCGH$X_2$P$X_3$ 3', 5' TCGH$X_2$P$X_3$ 3', 5' DCGHP$X_3$ 3', or 5' DCGHP 3'.

In other aspects the invention provides immune stimulatory nucleic acids which are defined by a formula: 5' $N_1$PyG$N_2$P 3'. $N_1$ is any sequence 1 to 6 nucleotides long. Py is a pyrimidine. G is guanine. $N_2$ is any sequence 0 to 30 nucleotides long. P is a GC-rich palindrome containing sequence at least 10 nucleotides long.

$N_1$ and $N_2$ may contain more than 50% pyrimidines, and more preferably more than 50% T. $N_1$ may include a CG, in which case there is preferably a T immediately preceding this CG. In some embodiments $N_1$PyG is TCG (such as ODN 5376, which has a 5' TCGG), and most preferably a TCG$N_2$, where $N_2$ is not G.

$N_1$PyG$N_2$P may include one or more inosine (I) nucleotides. Either the C or the G in N1 may be replaced by inosine, but the CpI is preferred to the IpG. For inosine substitutions such as IpG, the optimal activity may be achieved with the use of a "semi-soft" or chimeric backbone, where the linkage between the IG or the CI is phosphodiester. $N_1$ may include at least one CI, TCI, IG or TIG motif.

In certain embodiments $N_1$PyG$N_2$ is a sequence selected from the group consisting of TTTTTCG, TCG, TTCG, TTTCG, TTTTCG, TCGT, TTCGT, TTTCGT, and TCGTCGT.

Some non limiting examples of C-Class nucleic acids include:

| SEQ ID NO | Sequence |
|---|---|
| 17 | T*C_G*C_G*T*C_G*T*T*C_G*G*C*G*C_G*C*G*C*C*G |
| 18 | T*C_G*T*C_G*A*C_G*T*T*C_G*G*C*G*C_G*C*G*C*C*G |
| 19 | T*C_G*G*A*C_G*T*T*C_G*G*C*G*C_G*C*G*C*C*G |
| 20 | T*C_G*G*A*C_G*T*T*C_G*G*C*G*C*G*C*C*G |
| 21 | T*C_G*C_G*T*C_G*T*T*C_G*G*C*G*C*G*C*C*G |
| 22 | T*C_G*A*C_G*T*T*C_G*G*C*G*C_G*C*G*C*C*G |
| 23 | T*C_G*A*C_G*T*T*C_G*G*C*G*C*G*C*C*G |
| 24 | T*C_G*C_G*T*C_G*T*T*C_G*G*C*G*C*C*G |
| 25 | T*C_G*C_G*A*C_G*T*T*C_G*G*C*G*C_G*C*G*C*C*G |

For facilitating uptake into cells, immunostimulatory nucleic acids, including CpG-containing oligonucleotides, are preferably in the range of 8 to 100 bases in length. However, nucleic acids of any size greater than 8 nucleotides (even many kb long) are capable of inducing an immune response according to the invention if sufficient immunostimulatory motifs are present, since larger nucleic acids are degraded into oligonucleotides inside of cells. Preferably the immunostimulatory nucleic acid is in the range of between 8 and 100 nucleotides in length. In some preferred embodiments the immunostimulatory nucleic acids is between 12 and 40 nucleotides in length. In more preferred embodiments the immunostimulatory nucleic acids is between 8 and 30 nucleotides in length. In most preferred embodiments the immunostimulatory nucleic acids is between 8 and 24 nucleotides in length.

"Palindromic sequence" shall mean an inverted repeat, i.e., a sequence such as ABCDEE'D° C.'B'A' in which A and A', B and B', C and C', D and D', and E and E' are bases capable of forming the usual Watson-Crick base pairs. In vivo, such palindromic sequences may form double-stranded structures. In one embodiment the CpG oligonucleotide contains a palindromic sequence. A palindromic sequence used in this context refers to a palindrome in which the CpG is part of the palindrome, and preferably is the center of the palindrome. In another embodiment the CpG oligonucleotide is free of a palindrome. A CpG oligonucleotide that is free of a palindrome is one in which the CpG dinucleotide is not part of a palindrome. Such an oligonucleotide may include a palindrome in which the CpG is not the center of the palindrome.

In some embodiments of the invention the immunostimulatory oligonucleotides include immunostimulatory motifs which are "CpG dinucleotides". A CpG dinucleotide can be methylated or unmethylated. An immunostimulatory nucleic acid containing at least one unmethylated CpG dinucleotide is a nucleic acid molecule which contains an unmethylated cytosine-guanine dinucleotide sequence (i.e., an unmethylated 5' cytidine followed by 3' guanosine and linked by a phosphate bond) and which activates the immune system; such an immunostimulatory nucleic acid is a CpG nucleic acid. CpG nucleic acids have been described in a number of issued patents, published patent applications, and other publications, including U.S. Pat. Nos. 6,194,388; 6,207,646; 6,214,806; 6,218,371; 6,239,116; and 6,339,068. An immunostimulatory nucleic acid containing at least one methylated CpG dinucleotide is a nucleic acid which contains a methylated cytosine-guanine dinucleotide sequence (i.e., a methylated 5' cytidine followed by a 3' guanosine and linked by a phosphate bond) and which activates the immune system. In other embodiments the immunostimulatory oligonucleotides are free of CpG dinucleotides. These oligonucleotides which are free of CpG dinucleotides are referred to as non-CpG oligonucleotides, and they have non-CpG immunostimulatory motifs. The invention, therefore, also encompasses nucleic acids with other types of immunostimulatory motifs. Which can be methylated or unmethylated. The immunostimulatory oligonucleotides of the invention, further, can include any combination of methylated and unmethylated CpG and non-CpG immunostimulatory motifs.

The immunostimulatory nucleic acid molecules may have a chimeric backbone. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could in one embodiment include at least one phosphodiester (phosphodiester or phosphodiester-like) linkage and at least one boranophosphonate (stabilized) linkage. In another embodiment a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vivo degradation (e.g., via an exo- or endo-nuclease), compared to a phosphodiester internucleotide linkage. Preferred stabilized internucleotide linkages include, without limitation, phosphorothioate, phosphorodithioate, methylphosphonate, and methylphosphorothioate. Other stabilized internucleotide linkages include, without limitation: peptide, alkyl, dephospho, and others as described above.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E et al. (1990) Chem Rev 90:544; Goodchild J (1990) *Bioconjugate Chem* 1:165. Methods for preparing chimeric oligonucleotides are also known. For instance patents issued to Uhlmann et al have described such techniques.

Mixed backbone modified ODN may be synthesized using a commercially available DNA synthesizer and standard phosphoramidite chemistry. (F. E. Eckstein, "Oligonucleotides and Analogues—A Practical Approach" *IRL Press, Oxford, UK,* 1991, and M. D. Matteucci and M. H. Caruthers, *Tetrahedron Lett.* 21, 719 (1980)) After coupling, PS linkages are introduced by sulfurization using the Beaucage reagent (R. P. Iyer, W. Egan, J. B. Regan and S. L. Beaucage, *J. Am. Chem. Soc.* 112, 1253 (1990)) (0.075 M in acetonitrile) or phenyl acetyl disulfide (PADS) followed by capping with acetic anhydride, 2,6-lutidine in tetrahydrofurane (1:1:8; v:v:v) and N-methylimidazole (16% in tetrahydrofurane). This capping step is performed after the sulfurization reaction to minimize formation of undesired phosphodiester (PO) linkages at positions where a phosphorothioate linkage should be located. In the case of the introduction of a phosphodiester linkage, e.g. at a CpG dinucleotide, the intermediate phosphorous-III is oxidized by treatment with a solution of iodine in water/pyridine. After cleavage from the solid support and final deprotection by treatment with concentrated ammonia (5 hrs at 50° C.), the ODN are analyzed by HPLC on a Gen-Pak Fax column (Millipore-Waters) using a NaCl-gradient (e.g. buffer A: 10 mM $NaH_2PO_4$ in acetonitrile/water=1:4/v:v pH 6.8; buffer B: 10 mM $NaH_2PO_4$, 1.5 M NaCl in acetonitrile/water=1:4/v:v; 5 to 60% B in 30 minutes at 1 ml/min) or by capillary gel electrophoresis. The ODN can be purified by HPLC or by FPLC on a Source High Performance column (Amersham Pharmacia). HPLC-homogeneous fractions are combined and desalted via a C18 column or by ultrafiltration. The ODN was analyzed by MALDI-TOF mass spectrometry to confirm the calculated mass.

The nucleic acids of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

In some embodiments the oligonucleotides may be soft or semi-soft oligonucleotides. A soft oligonucleotide is an immunostimulatory oligonucleotide having a partially stabilized backbone, in which phosphodiester or phosphodiester-like internucleotide linkages occur only within and immediately adjacent to at least one internal pyrimidine-purine dinucleotide (YZ). Preferably YZ is YG, a pyrimidine-guanosine (YG) dinucleotide. The at least one internal YZ dinucleotide itself has a phosphodiester or phosphodiester-like internucleotide linkage. A phosphodiester or phosphodiester-like internucleotide linkage occurring immediately adjacent to the at least one internal YZ dinucleotide can be 5', 3', or both 5' and 3' to the at least one internal YZ dinucleotide.

In particular, phosphodiester or phosphodiester-like internucleotide linkages involve "internal dinucleotides". An internal dinucleotide in general shall mean any pair of adjacent nucleotides connected by an internucleotide linkage, in which neither nucleotide in the pair of nucleotides is a terminal nucleotide, i.e., neither nucleotide in the pair of nucleotides is a nucleotide defining the 5' or 3' end of the oligonucleotide. Thus a linear oligonucleotide that is n nucleotides long has a total of n-1 dinucleotides and only n-3 internal dinucleotides. Each internucleotide linkage in an internal dinucleotide is an internal internucleotide linkage. Thus a linear oligonucleotide that is n nucleotides long has a total of n-1 internucleotide linkages and only n-3 internal internucleotide linkages. The strategically placed phosphodiester or phosphodiester-like internucleotide linkages, therefore, refer to phosphodiester or phosphodiester-like internucleotide linkages positioned between any pair of nucleotides in the nucleic acid sequence. In some embodiments the phosphodiester or phosphodiester-like internucleotide linkages are not positioned between either pair of nucleotides closest to the 5' or 3' end.

Preferably a phosphodiester or phosphodiester-like internucleotide linkage occurring immediately adjacent to the at least one internal YZ dinucleotide is itself an internal internucleotide linkage. Thus for a sequence $N_1$ YZ $N_2$, wherein $N_1$ and $N_2$ are each, independent of the other, any single nucleotide, the YZ dinucleotide has a phosphodiester or phosphodiester-like internucleotide linkage, and in addition (a) $N_1$ and Y are linked by a phosphodiester or phosphodiester-like internucleotide linkage when $N_1$ is an internal nucleotide, (b) Z and $N_2$ are linked by a phosphodiester or phosphodiester-like internucleotide linkage when $N_2$ is an internal nucleotide, or (c) $N_1$ and Y are linked by a phosphodiester or phosphodiester-like internucleotide linkage when $N_1$ is an internal nucleotide and Z and $N_2$ are linked by a phosphodiester or phosphodiester-like internucleotide linkage when $N_2$ is an internal nucleotide.

Soft oligonucleotides according to the instant invention are believed to be relatively susceptible to nuclease cleavage compared to completely stabilized oligonucleotides. Without meaning to be bound to a particular theory or mechanism, it is believed that soft oligonucleotides of the invention are cleavable to fragments with reduced or no immunostimulatory activity relative to full-length soft oligonucleotides. Incorporation of at least one nuclease-sensitive internucleotide linkage, particularly near the middle of the oligonucleotide, is believed to provide an "off switch" which alters the pharmacokinetics of the oligonucleotide so as to reduce the duration of maximal immunostimulatory activity of the oligonucleotide. This can be of particular value in tissues and in clinical applications in which it is desirable to avoid injury related to chronic local inflammation or immunostimulation, e.g., the kidney.

A semi-soft oligonucleotide is an immunostimulatory oligonucleotide having a partially stabilized backbone, in which phosphodiester or phosphodiester-like internucleotide linkages occur only within at least one internal pyrimidine-purine (YZ) dinucleotide. Semi-soft oligonucleotides generally possess increased immunostimulatory potency relative to corresponding fully stabilized immunostimulatory oligonucleotides. Due to the greater potency of semi-soft oligonucleotides, semi-soft oligonucleotides may be used, in some instances, at lower effective concentrations and have lower effective doses than conventional fully stabilized immunostimulatory oligonucleotides in order to achieve a desired biological effect.

It is believed that the foregoing properties of semi-soft oligonucleotides generally increase with increasing "dose" of phosphodiester or phosphodiester-like internucleotide linkages involving internal YZ dinucleotides. Thus it is believed, for example, that generally for a given oligonucleotide sequence with five internal YZ dinucleotides, an oligonucleotide with five internal phosphodiester or phosphodiester-like YZ internucleotide linkages is more immunostimulatory than an oligonucleotide with four internal phosphodiester or phosphodiester-like YG internucleotide linkages, which in turn is more immunostimulatory than an oligonucleotide with three internal phosphodiester or phosphodiester-like YZ internucleotide linkages, which in turn is more immunostimulatory than an oligonucleotide with two internal phosphodiester or phosphodiester-like YZ internucleotide linkages, which in turn is more immunostimulatory than an oligonucleotide with one internal phosphodiester or phosphodiester-like YZ internucleotide linkage. Importantly, inclusion of even one internal phosphodiester or phosphodiester-like YZ internucleotide linkage is believed to be advantageous over no internal phosphodiester or phosphodiester-like YZ internucleotide linkage. In addition to the number of phosphodiester or phosphodiester-like internucleotide linkages, the position along the length of the nucleic acid can also affect potency.

The soft and semi-soft oligonucleotides will generally include, in addition to the phosphodiester or phosphodiester-like internucleotide linkages at preferred internal positions, 5' and 3' ends that are resistant to degradation. Such degradation-resistant ends can involve any suitable modification that results in an increased resistance against exonuclease digestion over corresponding unmodified ends. For instance, the 5' and 3' ends can be stabilized by the inclusion there of at least one phosphate modification of the backbone. In a preferred embodiment, the at least one phosphate modification of the backbone at each end is independently a phosphorothioate, phosphorodithioate, methylphosphonate, or methylphosphorothioate internucleotide linkage. In another embodiment, the degradation-resistant end includes one or more nucleotide units connected by peptide or amide linkages at the 3' end.

A phosphodiester internucleotide linkage is the type of linkage characteristic of nucleic acids found in nature. As shown in FIG. 20, the phosphodiester internucleotide linkage includes a phosphorus atom flanked by two bridging oxygen atoms and bound also by two additional oxygen atoms, one charged and the other uncharged. Phosphodiester internucleotide linkage is particularly preferred when it is important to reduce the tissue half-life of the oligonucleotide.

A phosphodiester-like internucleotide linkage is a phosphorus-containing bridging group that is chemically and/or diastereomerically similar to phosphodiester. Measures of similarity to phosphodiester include susceptibility to nuclease digestion and ability to activate RNAse H. Thus for example phosphodiester, but not phosphorothioate, oligonucleotides are susceptible to nuclease digestion, while both phosphodiester and phosphorothioate oligonucleotides activate RNAse H. In a preferred embodiment the phosphodiester-like internucleotide linkage is boranophosphate (or equivalently, boranophosphonate) linkage. U.S. Pat. No. 5,177,198; U.S. Pat. No. 5,859,231; U.S. Pat. No. 6,160,109; U.S. Pat. No. 6,207,819; Sergueev et al., (1998) *J Am Chem Soc* 120:9417-27. In another preferred embodiment the phosphodiester-like internucleotide linkage is diasteromerically pure Rp phosphorothioate. It is believed that diasteromerically pure Rp phosphorothioate is more susceptible to nuclease digestion and is better at activating RNAse H than mixed or diastereomerically pure Sp phosphorothioate. Stereoisomers of CpG oligonucleotides are the subject of co-pending U.S. patent application Ser. No. 09/361,575 filed Jul. 27, 1999, and published PCT application PCT/US99/17100 (WO 00/06588). It is to be noted that for purposes of the instant invention, the term "phosphodiester-like internucleotide linkage" specifically excludes phosphorodithioate and methylphosphonate internucleotide linkages.

As described above the soft and semi-soft oligonucleotides of the invention may have phosphodiester like linkages between C and G. One example of a phosphodiester-like linkage is a phosphorothioate linkage in an Rp conformation. Oligonucleotide p-chirality can have apparently opposite effects on the immune activity of a CpG oligonucleotide, depending upon the time point at which activity is measured. At an early time point of 40 minutes, the $R_p$ but not the $S_p$ stereoisomer of phosphorothioate CpG oligonucleotide induces JNK phosphorylation in mouse spleen cells. In contrast, when assayed at a late time point of 44 hr, the $S_p$ but not the $R_p$ stereoisomer is active in stimulating spleen cell proliferation. This difference in the kinetics and bioactivity of the $R_p$ and $S_p$ stereoisomers does not result from any difference in cell uptake, but rather most likely is due to two opposing biologic roles of the p-chirality. First, the enhanced activity of the Rp stereoisomer compared to the Sp for stimulating immune cells at early time points indicates that the Rp may be more effective at interacting with the CpG receptor, TLR9, or inducing the downstream signalling pathways. On the other hand, the faster degradation of the Rp PS-oligonucleotides compared to the Sp results in a much shorter duration of signalling, so that the Sp PS-oligonucleotides appear to be more biologically active when tested at later time points.

A surprisingly strong effect is achieved by the p-chirality at the CpG dinucleotide itself. In comparison to a stereo-random CpG oligonucleotide the congener in which the single CpG dinucleotide was linked in Rp was slightly more active, while the congener containing an Sp linkage was nearly inactive for inducing spleen cell proliferation.

The size (i.e., the number of nucleotide residues along the length of the nucleic acid) of the immunostimulatory oligonucleotide may also contribute to the stimulatory activity of the oligonucleotide. For facilitating uptake into cells immunostimulatory oligonucleotides preferably have a minimum length of 6 nucleotide residues. Nucleic acids of any size greater than 6 nucleotides (even many kb long) are capable of inducing an immune response according to the invention if sufficient immunostimulatory motifs are present, since larger nucleic acids are degraded inside of cells. It is believed by the instant inventors that semi-soft oligonucleotides as short as 4 nucleotides can also be immunostimulatory if they can be delivered to the interior of the cell. In certain preferred embodiments according to the instant invention, the immunostimulatory oligonucleotides are between 4 and 100 nucleotides long. In typical embodiments the immunostimulatory oligonucleotides are between 6 and 40 nucleotides long. In certain preferred embodiments according to the instant invention, the immunostimulatory oligonucleotides are between 6 and 19 nucleotides long.

The immunostimulatory oligonucleotides generally have a length in the range of between 4 and 100 and in some embodiments 10 and 40. The length may be in the range of between 16 and 24 nucleotides.

The terms "nucleic acid" and "oligonucleotide" also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as arabinose or 2'-fluoroarabinose instead of ribose. Thus the nucleic acids may be heterogeneous in backbone composition thereby containing any possible combination of polymer units linked together such as peptide-nucleic acids (which have an amino acid backbone with nucleic acid bases).

Nucleic acids also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, thymine, 5-methylcytosine, 5-hydroxycytosine, 5-fluorocytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art.

The immunostimulatory oligonucleotides of the instant invention can encompass various chemical modifications and substitutions, in comparison to natural RNA and DNA, involving a phosphodiester internucleotide bridge, a β-D-ribose unit and/or a natural nucleotide base (adenine, guanine, cytosine, thymine, uracil). Examples of chemical modifications are known to the skilled person and are described, for example, in Uhlmann E et al. (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) *Annu Rev Pharmacol Toxicol* 36:107-129; and Hunziker J et al. (1995) *Mod Synth Methods* 7:331-417. An oligonucleotide according to the invention may have one or more modifications, wherein each modification is located at a particular phosphodiester internucleotide bridge and/or at a particular β-D-ribose unit and/or at a particular natural nucleotide base position in comparison to an oligonucleotide of the same sequence which is composed of natural DNA or RNA.

For example, the invention relates to an oligonucleotide which may comprise one or more modifications and wherein each modification is independently selected from:
a) the replacement of a phosphodiester internucleotide bridge located at the 3' and/or the 5' end of a nucleotide by a modified internucleotide bridge,
b) the replacement of phosphodiester bridge located at the 3' and/or the 5' end of a nucleotide by a dephospho bridge,
c) the replacement of a sugar phosphate unit from the sugar phosphate backbone by another unit,
d) the replacement of a β-D-ribose unit by a modified sugar unit, and
e) the replacement of a natural nucleotide base by a modified nucleotide base.

More detailed examples for the chemical modification of an oligonucleotide are as follows.

A phosphodiester internucleotide bridge located at the 3' and/or the 5' end of a nucleotide can be replaced by a modified internucleotide bridge, wherein the modified internucleotide bridge is for example selected from phosphorothioate, phosphorodithioate, $NR^1R^2$-phosphoramidate, boranophosphate, α-hydroxybenzyl phosphonate, phosphate-$(C_1-C_{21})$—O-alkyl ester, phosphate-$[(C_6-C_{12})$aryl-$(C_1-C_{21})$—O-alkyl]ester, $(C_1-C_8)$alkylphosphonate and/or $(C_6-C_{12})$arylphosphonate bridges, $(C_7-C_{12})$-α-hydroxymethyl-aryl (e.g., disclosed in WO 95/01363), wherein $(C_6-C_{12})$aryl, $(C_6-C_{20})$aryl and $(C_6-C_{14})$aryl are optionally substituted by halogen, allyl, alkoxy, nitro, cyano, and where $R^1$ and $R^2$ are, independently of each other, hydrogen, $(C_1-C_{18})$-alkyl, $(C_6-C_{20})$-aryl, $(C_6-C_{14})$-aryl-$(C_1-C_8)$-alkyl, preferably hydrogen, $(C_1-C_8)$-alkyl, preferably $(C_1-C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleotide by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

A sugar phosphate unit (i.e., a β-D-ribose and phosphodiester internucleotide bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) *Nucleic Acids Res* 17:6129-41), that is, e.g., the replacement by a morpholino-derivative unit; or to build up a polyamide nucleic acid ("PNA"; as described for example, in Nielsen P E et al. (1994) *Bioconjug Chem* 5:3-7), that is, e.g., the replacement by a PNA backbone unit, e.g., by 2-aminoethylglycine.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O—$(C_1-C_6)$alkyl-ribose, preferably 2'-O—$(C_1-C_6)$ alkyl-ribose is 2'-O-methylribose, 2'-O—$(C_2-C_6)$alkenyl-ribose, 2'-[O—$(C_1-C_6)$alkyl-O—$(C_1-C_6)$alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481).

In some preferred embodiments the sugar is 2'-O-methylribose, particularly for one or both nucleotides linked by a phosphodiester or phosphodiester-like internucleotide linkage.

Nucleic acids also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, and thymine, and other naturally and non-naturally occurring nucleobases, substituted and unsubstituted aromatic moieties.

A modified base is any base which is chemically distinct from the naturally occurring bases typically found in DNA and RNA such as T, C, G, A, and U, but which share basic chemical structures with these naturally occurring bases. The modified nucleotide base may be, for example, selected from hypoxanthine, uracil, dihydrouracil, pseudouracil, 2-thiouracil, 4-thiouracil, 5-aminouracil, 5-$(C_1-C_6)$-alkyluracil, 5-$(C_2-C_6)$-alkenyluracil, 5-$(C_2-C_6)$-alkynyluracil, 5-(hydroxymethyl)uracil, 5-chlorouracil, 5-fluorouracil, 5-bromouracil, 5-hydroxycytosine, 5-$(C_1-C_6)$-alkylcytosine, 5-$(C_2-C_6)$-alkenylcytosine, 5-$(C_2-C_6)$-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleotides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleotide bases. This list is meant to be exemplary and is not to be interpreted to be limiting.

In particular formulas described herein a set of modified bases is defined. For instance the letter Y is used to refer to a nucleotide containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g. 3-nitropyrrole, P-base), an aromatic ring system (e.g. fluorobenzene or difluorobenzene) or a hydrogen atom (dSpacer).

The letter Z is used to refer to guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6) alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. In another embodiment of the invention, the guanine base is substituted by a universal base (e.g. 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom (dSpacer).

The oligonucleotides may have one or more accessible 5' ends. It is possible to create modified oligonucleotides having two such 5' ends. This may be achieved, for instance by attaching two oligonucleotides through a 3'-3' linkage to generate an oligonucleotide having one or two accessible 5' ends. The 3'3'-linkage may be a phosphodiester, phosphorothioate or any other modified internucleotide bridge. Methods for accomplishing such linkages are known in the art. For instance, such linkages have been described in Seliger, H.; et al., Oligonucleotide analogs with terminal 3'-3'- and 5'-5'-internucleotidic linkages as antisense inhibitors of viral gene expression, Nucleotides & Nucleotides (1991), 10(1-3), 469-77 and Jiang, et al., Pseudo-cyclic oligonucleotides: in vitro and in vivo properties, Bioorganic & Medicinal Chemistry (1999), 7(12), 2727-2735.

Additionally, 3'3'-linked nucleic acids where the linkage between the 3'-terminal nucleotides is not a phosphodiester, phosphorothioate or other modified bridge, can be prepared using an additional spacer, such as tri- or tetra-ethylenglycol phosphate moiety (Durand, M. et al, Triple-helix formation by an oligonucleotide containing one (dA)12 and two (dT)12 sequences bridged by two hexaethylene glycol chains, Biochemistry (1992), 31(38), 9197-204, U.S. Pat. No. 5,658,738, and U.S. Pat. No. 5,668,265). Alternatively, the non-nucleotidic linker may be derived from ethanediol, propanediol, or from an abasic deoxyribose (dSpacer) unit (Fontanel, Marie Laurence et al., Sterical recognition by T4 polynucleotide kinase of non-nucleosidic moieties 5'-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

For use in the instant invention, the oligonucleotides of the invention can be synthesized de novo using any of a number of procedures well known in the art. For example, the b-cyanoethyl phosphoramidite method (Beaucage, S. L., and Caruthers, M. H., Tet. Let. 22:1859, 1981); nucleotide H-phosphonate method (Garegg et al., Tet. Let. 27:40514054, 1986; Froehler et al., Nucl. Acid. Res. 14:5399-5407, 1986; Garegg et al., Tet. Let. 27:4055-4058, 1986, Gaffney et al., Tet. Let. 29:2619-2622, 1988). These chemistries can be performed by a variety of automated nucleic acid synthesizers available in the market. These oligonucleotides are referred to as synthetic oligonucleotides. An isolated oligonucleotide generally refers to an oligonucleotide which is separated from components which it is normally associated with in nature. As an example, an isolated oligonucleotide may be one which is separated from a cell, from a nucleus, from mitochondria or from chromatin.

The oligonucleotides are partially resistant to degradation (e.g., are stabilized). A "stabilized oligonucleotide molecule" shall mean an oligonucleotide that is relatively resistant to in vivo degradation (e.g. via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases. Other modified oligonucleotides include phosphodiester modified nucleic acids, combinations of phosphodiester and phosphorothioate nucleic acid, methylphosphonate, methylphosphorothioate, phosphorodithioate, p-ethoxy, and combinations thereof.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (e.g., Uhlmann, E. and Peyman, A., Chem. Rev. 90:544, 1990; Goodchild, J., Bioconjugate Chem. 1:165, 1990).

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The immunostimulatory oligonucleotides may also contain one or more unusual linkages between the nucleotide or nucleotide-analogous moieties. The usual internucleoside linkage is the 3'5'-linkage. All other linkages are considered as unusual internucleoside linkages, such as 2'5'-, 5'5'-, 3'3'-, 2'2'-, 2'3'-linkages. Thereby, the nomenclature 2' to 5' is chosen according to the carbon atom of ribose. However, if unnatural sugar moieties are employed, such as ring-expanded sugar analogs (e.g. hexanose, cylohexene or pyranose) or bi- or tricyclic sugar analogs, then this nomenclature changes according to the nomenclature of the monomer. In 3'-deoxy-β-D-ribopyranose analogs (also called p-DNA), the mononucleotides are e.g. connected via a 4'2'-linkage.

If the nucleotide contains one 3'3'-linkage, then this oligonucleotide analog will have two unlinked 5'-ends. Similarly, if the nucleotide contains one 5'5'-linkage, then this oligonucleotide analog will have two unlinked 3'-ends. The accessibility of unlinked ends of nucleotides may be better accessible by their receptors. Both types of unusual linkages (3'3'- and 5'5') were described by Ramalho Ortigao et al. (Antisense Research and Development (1992) 2, 129-46), whereby oligonucleotides having a 3'3'-linkage were reported to show enhanced stability towards cleavage by nucleases.

Different types of linkages can also be combined in one molecule which may lead to branching of the oligomer. If one part of the oligonucleotide is connected at the 3'-end via a 3'3'-linkage to a second oligonucleotide part and at the 2'-end via a 2'3'-linkage to a third part of the molecule, this results e.g. in a branched oligonucleotide with three 5'-ends (3'3'-, 2'3'-branched).

In principle, linkages between different parts of an oligonucleotide or between different oligonucleotides, respectively, can occur via all parts of the molecule, as long as this does not negatively interfere with the recognition by its receptor. According to the nature of the nucleic acid, the linkage can involve the sugar moiety (Su), the heterocyclic nucleobase (Ba) or the phosphate backbone (Ph). Thus, linkages of the type Su-Su, Su-Ph, Su-Ba, Ba-Ba, Ba-Su, Ba-Ph, Ph-Ph, Ph-Su, and Ph-Ba are possible. If the oligonucleotides are further modified by certain non-nucleotidic substituents, the linkage can also occur via the modified parts of the oligonucleotides. These modifications include also modified nucleic acids, e.g. PNA, LNA, or Morpholino Oligonucleotide analogs.

The linkages are preferably composed of C, H, N, O, S, B, P, and Halogen, containing 3 to 300 atoms. An example with 3 atoms is an acetal linkage (ODN1-3'-O—CH2—O-3'-ODN2; Froehler and Matteucci) connecting e.g. the 3'-hydroxy group of one nucleotide to the 3'-hydroxy group of a second oligonucleotide. An example with about 300 atoms is PEG-40 (tetraconta polyethyleneglycol). Preferred linkages are phosphodiester, phosphorothioate, methylphosphonate, phosphoramidate, boranophosphonate, amide, ether, thioether, acetal, thioacetal, urea, thiourea, sulfonamide, Schiff' Base and disulfide linkages. Another possibility is the use of the Solulink BioConjugation System.

If the oligonucleotide is composed of two or more sequence parts, these parts can be identical or different. Thus, in an oligonucleotide with a 3'3'-linkage, the sequences can be identical 5'-ODN1-3'3'-ODN1-5' or different 5'-ODN1-3'3'-ODN2-5'. Furthermore, the chemical modification of the various oligonucleotide parts as well as the linker connecting them may be different. Since the uptake of short oligonucleotides appears to be less efficient than that of long oligonucleotides, linking of two or more short sequences results in improved immune stimulation. The length of the short oligonucleotides is preferably 2-20 nucleotides, more preferably 3-16 nucleotides, but most preferably 5-10 nucleotides. Preferred are linked oligonucleotides which have two or more unlinked 5'-ends.

The oligonucleotide partial sequences may also be linked by non-nucleotidic linkers, in particular abasic linkers (dSpacers), trietyhlene glycol units or hexaethylene glycol units. Further preferred linkers are alkylamino linkers, such as C3, C6, C12 aminolinkers, and also alkylthiol linkers, such as C3 or C6 thiol linkers. The oligonucleotides can also be linked by aromatic residues which may be further substituted by allyl or substituted allyl groups. The oligonucleotides may also contain a Doubler or Trebler unit (Glen Research), in particular those oligonucleotides with a 3'3'-linkage. Branching of the oligonucleotides by multiple doubler, trebler, or other multiplier units leads to dendrimers which are a further embodiment of this invention. The oligonucleotides may also contain linker units resulting from peptide modifying reagents or oligonucleotide modifying reagents (Glen Research). Furthermore, it may contain one or more natural or unnatural amino acid residues which are connected by peptide (amide) linkages.

Another possibility for linking oligonucleotides is via crosslinking of the heterocyclic bases (Verma and Eckstein; Annu. Rev. Biochem. (1998) 67: 99-134; page 124). Yet another possibility is a linkage between the sugar moiety of one sequence part with the heterocyclic base of another sequence part (Iyer et al. Curr. Opin. Mol. Therapeutics (1999) 1: 344-358; page 352).

The different oligonucleotides are synthesized by established methods and can be linked together on-line during solid-phase synthesis. Alternatively, they may be linked together post-synthesis of the individual partial sequences.

A "subject" shall mean a human or vertebrate animal including but not limited to a dog, cat, horse, cow, pig, sheep, goat, chicken, non-human primate (e.g., monkey), fish (aquaculture species, e.g., salmon), rabbit, rat, and mouse.

A "subject having a viral infection" is a subject that has been exposed to a virus and has acute or chronic manifestations or detectable levels of the virus in the body. In preferred embodiments of the invention, the subject is one having a chronic viral infection, more preferably a chronic hepatitis C infection. In important aspects of the invention, the subject is one that is non-responsive to prior therapy for hepatitis C infection. For example, a non-responsive subject includes one that was previously treated for hepatitis C infection with, for example, IFN-α (e.g., Intron A), and but such treatment was not successful, as described herein. The invention intends to treat subjects that are non-responsive, and in some instances to identify subjects that would be non-responsive in order to triage effective treatment.

Immunostimulatory nucleic acids can be effective in any vertebrate. Different immunostimulatory nucleic acids can cause optimal immune stimulation depending on the mammalian species. Thus an immunostimulatory nucleic acid causing optimal stimulation or inhibition in humans may not cause optimal stimulation or inhibition in a mouse, and vice versa. One of skill in the art can identify the most appropriate immunostimulatory nucleic acids useful for a particular mammalian species of interest using routine assays described herein and/or known in the art, using the guidance supplied herein.

The immunostimulatory nucleic acid may be directly administered to the subject or may be administered in conjunction with a nucleic acid delivery complex. A "nucleic acid delivery complex" shall mean a nucleic acid molecule associated with (e.g., ionically or covalently bound to, or encapsulated within) a targeting means (e.g., a molecule that results in higher affinity binding to target cell (e.g., pDCs or B cells) and/or increased cellular uptake by target cells. Examples of nucleic acid delivery complexes include nucleic acids associated with: a sterol (e.g., cholesterol), a lipid (e.g., a cationic lipid, virosome or liposome), or a target cell specific binding agent (e.g., a ligand recognized by target cell specific receptor). Preferred complexes may be sufficiently stable in vivo to prevent significant uncoupling prior to internalization by the target cell. However, the complex can be cleavable under appropriate conditions within the cell so that the nucleic acid is released in a functional form.

The immunostimulatory nucleic acid or other therapeutics may be administered alone (e.g., in saline or buffer) or using any delivery vehicles known in the art. For instance the following delivery vehicles have been described: cochleates; emulsomes; ISCOMs; liposomes; live bacterial vectors (e.g., *Salmonella, Escherichia coli, Bacillus Calmette-Guerin, Shigella, Lactobacillus*); live viral vectors (e.g., Vaccinia, adenovirus, Herpes Simplex); microspheres; nucleic acid vaccines; polymers (e.g., carboxymethylcellulose, chitosan); polymer rings; Proteosomes; sodium fluoride; transgenic plants; virosomes; virus-like particles. Those skilled in the art will recognize that other delivery vehicles that are known in the art may also be used.

Combined with the teachings provided herein, by choosing among the various active compounds and weighing factors such as potency, relative bioavailability, patient body weight, severity of adverse side-effects and preferred mode of administration, an effective therapeutic treatment regimen can be planned which does not cause substantial toxicity and yet is entirely effective to treat the particular subject as described above. The effective amount for any particular application can vary depending on such factors as the disease or condition being treated, the particular immunostimulatory nucleic acid being administered (e.g., the class of CpG immunostimulatory nucleic acid, the number of unmethylated CpG motifs or their location in the nucleic acid, the degree of chirality to the oligonucleotide, etc.), whether an antigen is also administered and the nature of such antigen, the size of the subject, or the severity of the disease or condition. One of ordinary skill in the art can empirically determine the effective amount of a particular immunostimulatory nucleic acids and/or other therapeutic agent without necessitating undue experimentation.

For adult human subjects, doses of the immunostimulatory nucleic acids compounds described herein typically range from about 50 μg/dose to 20 mg/dose, more typically from about 80 μg/dose to 8 mg/dose, and most typically from about 800 μg/dose to 4 mg/dose. Stated in terms of subject body weight, typical dosages range from about 0.5 to 500 μg/kg/dose, more typically from about 1 to 100 μg/kg/dose, and most typically from about 10 to 50 μg/kg/dose. Doses will depend on factors including the route of administration, e.g., oral administration may require a substantially larger dose than subcutaneous administration.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The immunostimulatory nucleic acids can be given in conjunction with other agents known in the art to be useful in treating viral infections. Of particular importance is the combination of immunostimulatory nucleic acids with anti-viral agents such as IFN-α, as demonstrated in the Examples section, to provide a synergistic response. Immunostimulatory nucleic acids can be used as a substitute for Ribavirin, which currently is administered together with IFN-α. Examples of such other agents currently used or under investigation for use in combination with IFN-α include amantadine, and cytokines, including IL-2, IL-10, IL-12, and IFN-γ.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g., amantadine), synthesis or translation of viral mRNA, including translation initiation (e.g., interferon, antisense, and ribozymes), virus enzymes (e.g., nonstructural serine proteases, RNA polymerases, reverse transcriptases and helicases), replication of viral RNA or DNA (e.g., nucleoside analogues), maturation of new virus proteins (e.g., protease inhibitors such as serine protease inhibitor BILN2061ZW from Boehringer Ingelheim), anti-oxidants such as Livfit (U.S. Pat. No. 6,136,316), and budding and release of the virus. Other anti-viral agents are described in U.S. Pat. Nos. 6,130,326, and 6,440,985, and published US patent application 20020095033. Ribavirin analogues are also anti-viral agents embraced by the invention.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination.

Immunoglobulin therapy is typically used for the prevention of viral infection, but can also be used to reduce levels of circulating virus and preventing newly formed cells from becoming infected. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the reduction of viremia for the period of time that the antibodies are present in the host. In general there are two types of immunoglobulin therapies, normal immunoglobulin therapy and hyper-immunoglobulin therapy. Normal immune globulin therapy utilizes an antibody product which is prepared from the serum of normal blood donors and pooled. This pooled product contains low titers of antibody to a wide range of human viruses, such as hepatitis A, parvovirus, enterovirus (especially in neonates). To use normal immune globulin therapy for HCV, the serum would have to be obtained from people who were previously infected with HCV and who have successfully cleared the infection, either spontaneously or with some form of therapy. Hyper-immune globulin therapy utilizes antibodies which are prepared from the serum of individuals who have high titers of an antibody to a particular virus. Those antibodies are then used against a specific virus. For HCV, hyper-immune globulins could be produced by vaccinating volunteers with recombinant HCV proteins to produce hepatitis C immune globulin.

Other anti-virals suitable in the methods of the invention are manufactured by Triangle Pharmaceuticals, Inc., Gilead, ICN, Procter and Gamble and ViroPharma Incorporated.

For use in therapy, an effective amount of the immunostimulatory nucleic acid can be administered to a subject by any mode that delivers the immunostimulatory nucleic acids to the desired site, e.g., mucosal, systemic. "Administering" the pharmaceutical composition of the present invention may be accomplished by any means known to the skilled artisan. Preferred routes of administration include but are not limited to oral, parenteral, intralesional, topical, transdermal, intramuscular, intranasal, intratracheal, inhalational, ocular, vaginal, and rectal.

For oral administration, the compounds (i.e., immunostimulatory nucleic acids, or other therapeutic agents) can be formulated readily by combining with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer *Science* 249:1527 (1990), which is incorporated herein by reference.

The immunostimulatory nucleic acids may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2 percent w/v); citric acid and a salt (1-3 percent w/v); boric acid and a salt (0.5-2.5 percent w/v); and phosphoric acid and a salt (0.8-2 percent w/v). Suitable preservatives include benzalkonium chloride (0.003-0.03 percent w/v); chlorobutanol (0.3-0.9 percent w/v); parabens (0.01-0.25 percent w/v) and thimerosal (0.004-0.02 percent w/v).

The pharmaceutical compositions of the invention contain a pharmaceutically-acceptable carrier. The term "pharmaceutically-acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

A variety of administration routes are available. The particular mode selected will depend, of course, upon the particular adjuvants or antigen selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer-based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In some embodiments, the immunostimulatory nucleic acid is modified. In certain embodiments, the immunostimulatory nucleic acid has a modified backbone with at least one nuclease-resistant internucleotide linkage. A nuclease-resistant internucleotide linkage can be selected from the group which includes a phosphorothioate linkage, a phosphorodithioate linkage, a methylphosphonate linkage, and a peptide linkage. In certain embodiments a modified immunostimulatory nucleic acid includes at least one nucleotide analog or at least one nucleotide analog. The immunostimulatory nucleic acid is a palindrome in certain embodiments, while in other embodiments, the immunostimulatory nucleic acid is not a palindrome. In some preferred embodiments the immunostimulatory nucleic acid is between 8 and 100 nucleotides in length, while in other preferred embodiments the immunostimulatory nucleic acid is between 12 and 40 nucleotides in length. Preferred sizes, sequences and modifications are described in greater detail below.

The following examples are included for purposes of illustration and are not intended to limit the scope of the invention.

EXAMPLES

The purpose of this study was to evaluate the ability of different classes of CpG ODN to stimulate PBMC from HCV chronic carriers. PBMC were isolated from whole blood collected from normal, healthy volunteers and chronic carriers of HCV and the ability of the different classes CpG ODNs as well as soft and semi-soft molecules to stimulate B cell proliferation, cytokine secretion (IFN-g, TNF-α, IL-10 and IFN-α) and chemokine secretion (IP-10) in vitro was evaluated.

Also evaluated were the immune stimulatory effects of exogenous IFN-α-2b (Intron A) and Ribavirin, either alone, in combination with each other, and in combination with CpG ODN (B and C classes).

Materials and Methods
Oligonucleotides

All oligonucleotide stocks were resuspended in TE buffer at pH 8.0 (OmniPer®; EM Science, Gibbstown, N.J.). Dilutions of various ODNs were made in RPMI 1640 complete media (Gibco BRL, Grand Island, N.Y.) containing 10% heat inactivated, normal human AB serum (Wisent Inc, St. Bruno, QC) and 1% penicillin/streptomycin (Gibco BRL, Grand Island, N.Y.) just prior to their use in cell assays. For the exogenous IFN-α synergy experiments, Intron A (Interferon Alfa-2b, DIN 02223406, Schering Canada Inc., Pointe-Claire, Quebec, Canada) was added to the ODN solutions to give final concentrations of 125 or 1000 IU/ml. Ribavirin (CAS 36791-04-5, Calbiochem, CN Biosciences Inc., La Jolla, Calif., USA) was reconstituted with sterile distilled water to produce a 500 μm stock and diluted in media as described above, to give a final concentration of 5 μm in wells. Cells were incubated at 37° C. with 5% $CO_2$. After 48 h, cell supernatants were collected from each well and frozen at −80° C.

ODNs used in experiments are shown in the following table:

TABLE 2

Sequences of oligos used in experiments

| SEQ ID NO: | CLASS | SEQUENCE |
|---|---|---|
| 1 | A | G-G-GGACGACGTCGTGG-G-G-G-G-G |
| 2 | B | TCG TCG TTT TGT CGT TTT GTC GTT |
| 3 | Control for B Class | TGC TGC TTT TTG CTG GCT TTT T |

TABLE 2-continued

Sequences of oligos used in experiments

| SEQ ID NO: | CLASS | SEQUENCE |
|---|---|---|
| 4 | C | TCGTCGTTTTCGGCGGCCGCCG |
| 5 | B | TCGTCGTTTCGTCGTTTTGTCGTT |
| 6 | B | TCG TCG TTT TTC GTG CGT TTT T |
| 7 | Soft C | TCGTCGTTT-T-C-G-G-CGGCCGCCG |
| 8 | semi-soft B | TC-GTC-GTTTT-GTC-GTTTTGTC-GTT |
| 9 | Semi-soft C | TCGTC-GTTTTCGGC-GGCCGCCG |
| 10 | Semi-soft C | TCGTCGTTTTC-GGCGGCC-GCCG |
| 11 | Semi-soft C | TCGTCG-TTTTC-GGCGCGC-GCCG |
| 12 | Semi-soft C | TCGTC-GTTTTC-GGC-GCGC-GCCG |
| 13 | Semi-soft C | TCGTCGTTTTAC-GGC-GCC-GTGCCG |
| 14 | Semi-soft C | TCGTCG-TTTTAC-GGCGCC-GTGCCG |
| 15 | Semi-soft C | TCGTC-GTTTTAC-GGCGCC-GTGCCG |
| 16 | Semi-soft C | TCGTC-GTTTTC-GGCGGCC-GCCG |

* A phosphodiester bond replacing a phosphorothioate bond within the oligonucleotide backbone is indicated by (-)

Isolation of PBMCs

Whole blood (200 ml) was collected by venous puncture into heparinized green top vacutainers from ten (10) normal, healthy, adult subjects and fifteen (15) adult subjects chronically infected with HCV who had a previous 6 month course of an IFN-α-based therapy and were either a treatment failure or a relapsed responder. Peripheral blood mononuclear cells (PBMCs) were purified by centrifugation over Ficoll-Hypaque (Amersham Pharmacia Biotech, Uppsala, Sweden) at 400×g for, 35 min. Cells were resuspended at a concentration of $10 \times 10^6$/ml in RPMI complete media containing 10% normal human AB serum (heat inactivated) and 1% penicillin/streptomycin.

B-Cell Proliferation

Cells were isolated as described above and resuspended at $1 \times 10^6$/ml in complete RPMI media 100 μl of cells were added to each well of round-bottom 96 well plates. ODN solutions (100 μl) were added to wells to give the selected range of final concentrations (1, 3, 6 μg/ml). Cells were cultured for 5 days and then pulsed with $^3$H-Thymidine (1 μCi/well) for 18 h, before harvesting onto filter paper for measuring radioactivity. Results are reported as stimulation index (SI) with respect to untreated media control.

Cytokine Assays

Freshly isolated PBMCs were resuspended at $10 \times 10^6$/ml (2× final concentration) and 100 μl of cells were added to each well of a 96 well flat-bottom plate containing an equal volume of ODN solution (2× final desired concentration). A range of concentrations (1, 3, 6 μg/ml) was tested for each ODN. Cells were incubated at 37° C. with 5% $CO_2$. After 48 h, cell supernatants were collected from each well and frozen at −80° C. until assayed.

IFN-α, IP-10, IL-10 and IFN-levels in supernatants were measured using commercial ELISA Kits (R&D Systems, Minneapolis, Minn., USA; IP-10, Cat# DIP 100, IL-10, Cat# D1000, IFN-g Cat# DIF50 or PBL Biomedical, IFN-α Cat# 4110S). When measured ELISA values were below the detection limit of the kit as specified by the manufacturer, a value equal to the lowest detectable limit was entered into data tables.

Results

PBMCs isolated from blood collected from 15 chronically infected HCV subjects and 10 normal healthy volunteers were incubated at 37° C. with different classes of CpG (e.g., class A, B, C, soft C, semi-soft B and semi-soft C), and cell supernatants were assessed for cytokine presence, indicative of cytokine secretion during the incubation period. Results of these experiments are presented below.

Induction of IFN-α Secretion by PBMC

When the three classes of CpG ODN were tested on PBMC from normal volunteers, very high levels of IFN-α were produced by the A class (CpG SEQ ID NO. 1), moderately high levels by the C class (CpG SEQ ID NO. 4) and only low levels were induced by the B class (CpG SEQ ID NO. 2) (FIG. 1). The main cellular source of IFN-α is pDC.

With the PBMC obtained from HCV chronic carriers, all three classes of CpG could induce secretion of IFN-α. The levels with the B and C classes were the same as those obtained with the normal PBMCs. In contrast, the A class induced only about 50% of the normal level (FIG. 1), suggesting that the dysfunction of the HCV-infected pDC has some impact on the efficacy of A class CpG to induce IFN-α, but not the C class. Thus, either A or C class CpG could be used to treat HCV chronic carriers, but in some instances the C class may be preferred.

Figure 3:
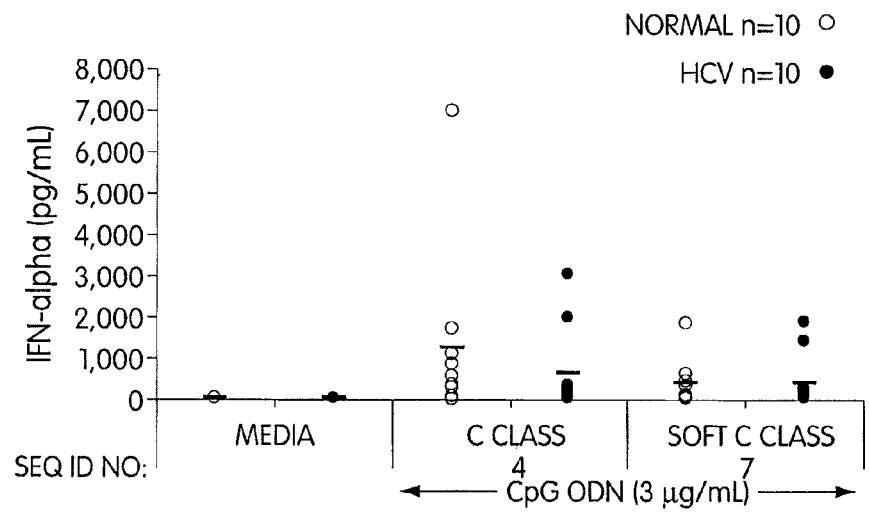
FIG. 3 shows the IFN-α induction by stimulation of PBMCs with C-class and soft-C oligonucleotides. PBMCs from normal or HCV-infected subjects were incubated with different classes of CpG for 48 h. Cell supernatants were collected and assayed for IFN-α a secretion by commercial ELISA kits. The average IFN-α secretion for 10 normal subjects and 10 HCV-infected subjects are shown by the black bars.

The number of pDC was determined by FACS analysis. A linear regression was performed against this compared to the amount of IFN-α secreted with either the A and C class CpG ODN, and a reasonable correlation for the normal subjects (e.g., R=0.43 and 0.58, respectively) was found. It was further discovered that the correlation was slightly better for the C class ODNs. In contrast, no correlation was observed between number of pDC and amount of IFN-α secreted for the HCV infected subjects (R=0.02 and 0.08, respectively) (FIG. 3). The HCV-infected DC are nevertheless capable of secreting IFN-α in response to the CpG ODN.

Figure 4:
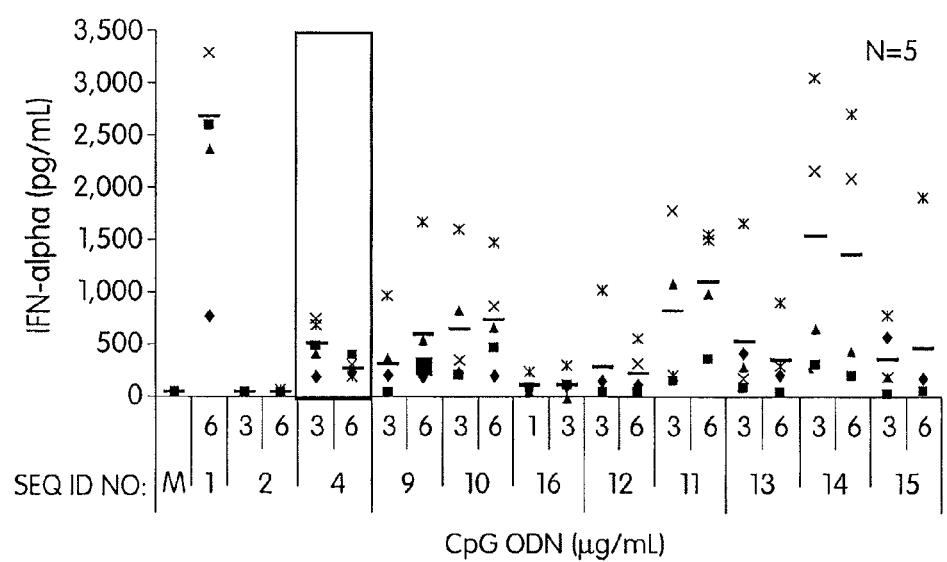
FIG. 4 shows the IFN-α induction following stimulation with a panel of semi-soft C-class CpG. PBMCs isolated from 5 HCV-infected subjects were incubated with a panel of semi-soft C-class oligonucleotides for 48 h. Cell supernatants were collected and assayed for IFN-α secretion by commercial ELISA kits. The average IFN-α secretion for 5 HCV-infected subjects are shown by the black bars.

The effect of soft and semi-soft alterations of these ODS was also analyzed. Soft molecules were synthesized that had a row of phosphodiester bonds in the central region of the molecule. Semi-soft molecules were synthesized that had one or more individual phosphodiester bonds that are between the cytosine and guanine nucleotides of the CpG motifs. Both soft (FIG. 3) and semi-soft (FIG. 4) C class CpG ODN were capable of stimulating IFN-α secretion from normal or HCV PBMC in a manner similar to the original C class CpG ODN. Several of the semi-soft C class CpG ODN were even more potent that the regular C class CpG SEQ ID NO. 4 (FIG. 4). This may be because the molecule is still sufficient stable to have maximal immune stimulation and the phosphodiester in the middle of the CpG motif?mass? increase its activity.

Induction of IFN-γ Secretion by PBMC

Figure 5:
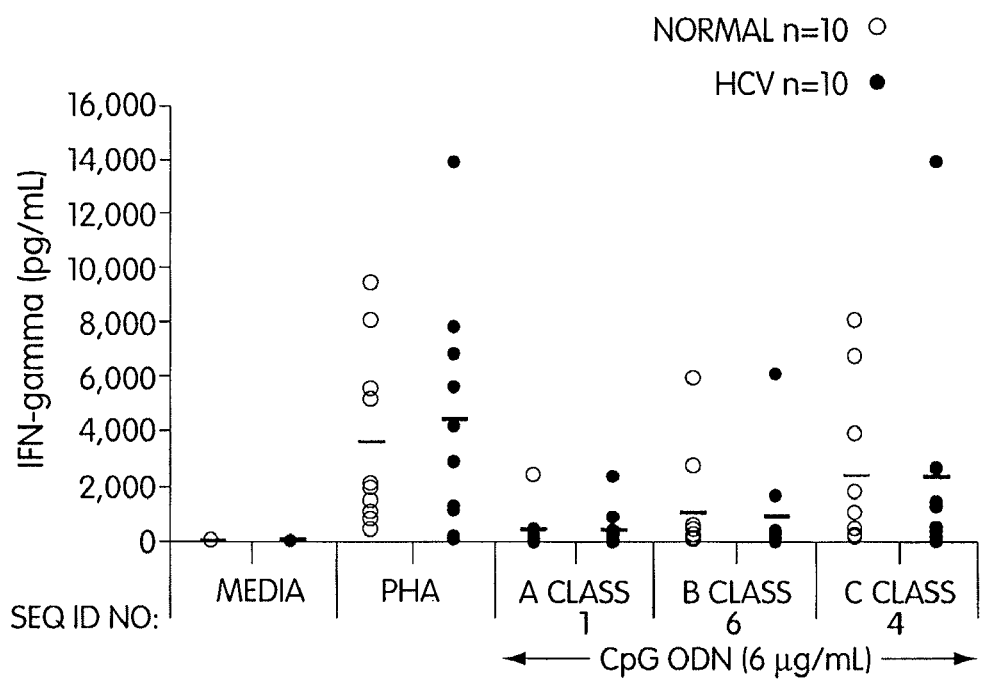
FIG. 5 shows the IFN-γ secretion following stimulation with three classes of CpG. PBMCs from normal or HCV-infected subjects were incubated with different classes of CpG for 48 h. Cell supernatants were collected and assayed for IFN-γ secretion by commercial ELISA kits. The average IFN-γ secretion for 10 normal subjects and 10 HCV-infected subjects are shown by the black bars.
Figure 6:
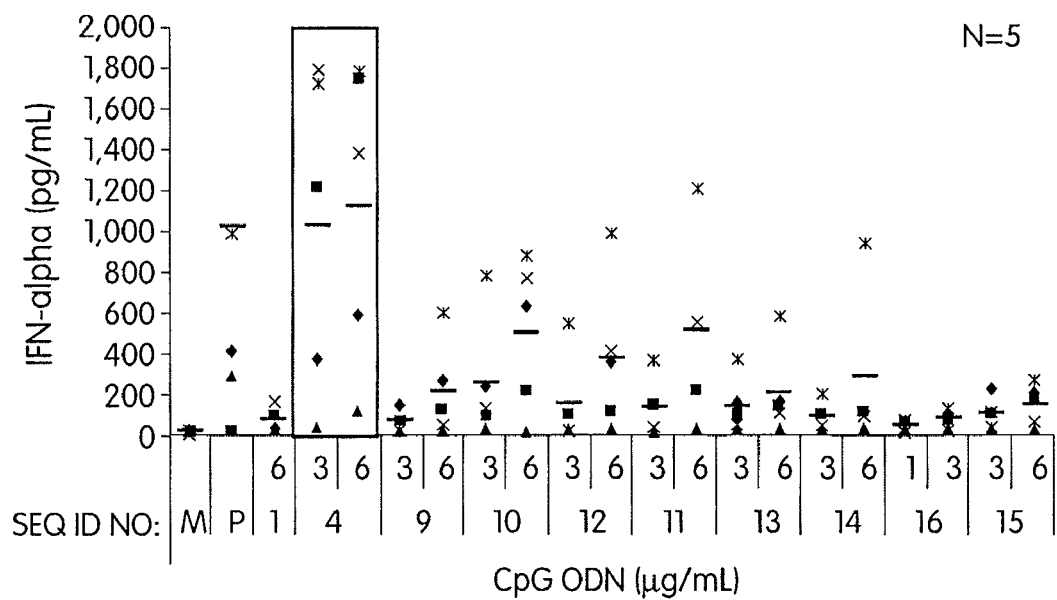
FIG. 6 shows the IFN-γ induction following stimulation with a panel of semi-soft C-class CpG. PBMCs isolated from 5 HCV-infected subjects were incubated with a panel of semi-soft C-class oligonucleotides for 48 h. Cell supernatants were collected and assayed for IFN-γ secretion by commercial ELISA kits. The average IFN-γ secretion for 5 HCV subjects are shown by the black bars.

FIG. 5 compares the ability of different classes of CpG to induce the secretion of Th1 cytokine, IFN-γ. Class A induced low levels of IFN-γ while in comparison class B produced moderate amounts and class C CpG stimulated high concentrations of IFN-γ. Both HCV-infected and normal PBMCs displayed a similar Th1 response to all three classes of CpG. Similar results were obtained with semi-soft class C CpG ODN (FIG. 6).

Induction of IP-10 Secretion by PBMC

Figure 7:
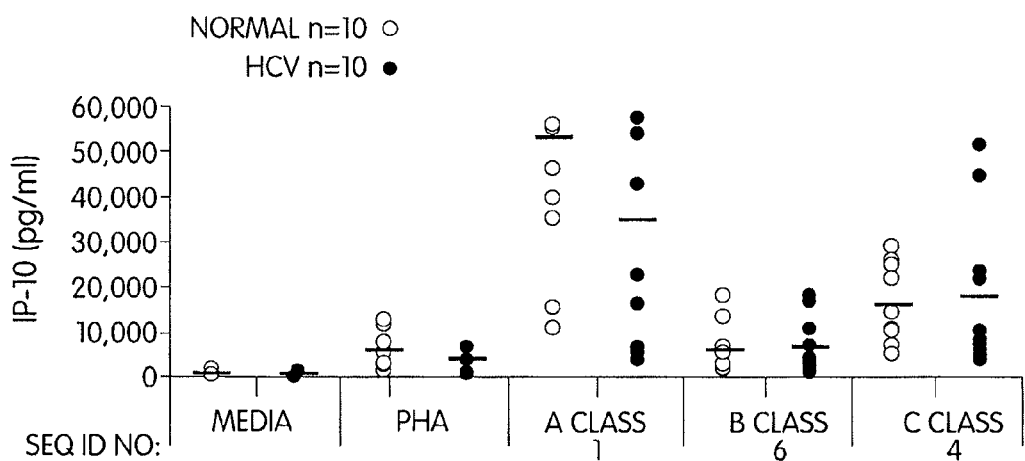
FIG. 7 shows the IP-10 secretion following stimulation with three classes of CpG. PBMCs from normal or HCV-infected subjects were incubated with different classes of CpG for 48 h. Cell supernatants were collected and assayed for IP-10 secretion by commercial ELISA kits. The average IP-10 secretion for 10 normal subjects and 10 HCV-infected subjects are shown by the black bars.

IP-10, a chemokine associated with production of type 1 and 2 interferons, is also induced by CpG ODN. Highest levels are induced with A class, next highest with C class and lowest with B class CpG ODN. Regardless of the class of CpG ODN, similar levels of IP-10 were induced with PBMCs from normal subjects and HCV chronic carriers (FIG. 7).

B Cell Stimulation by CpG ODN

Figure 8:
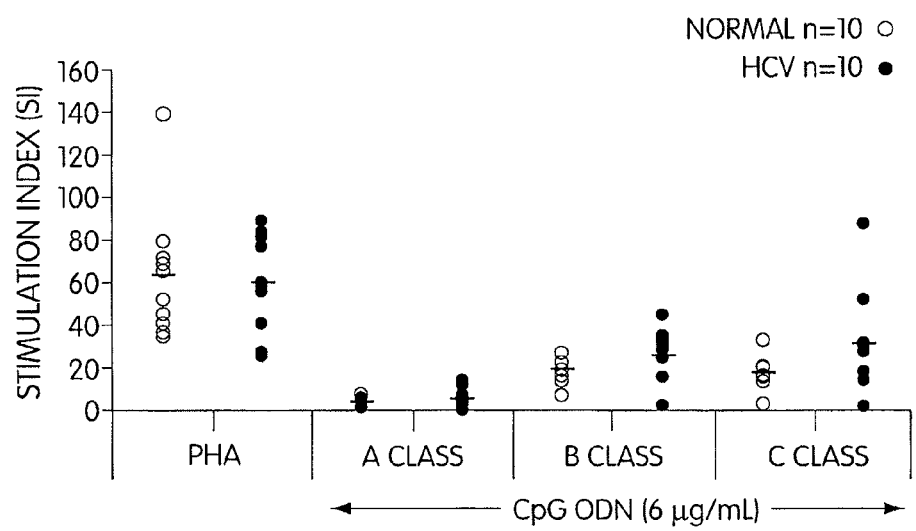
FIG. 8 shows the effect of CpG on B cell proliferation. PBMCs from HCV-infected or normal donors were incubated with class A, B or C CpG for 5 days. Cells were then pulsed with $^3$H-thymidine for 16 to 18 hours before measuring radioactivity. Values are represented as stimulation indices in comparison with media control (SI=cpm incubated with CpG/cpm of cells incubated with media alone).
Figure 9:
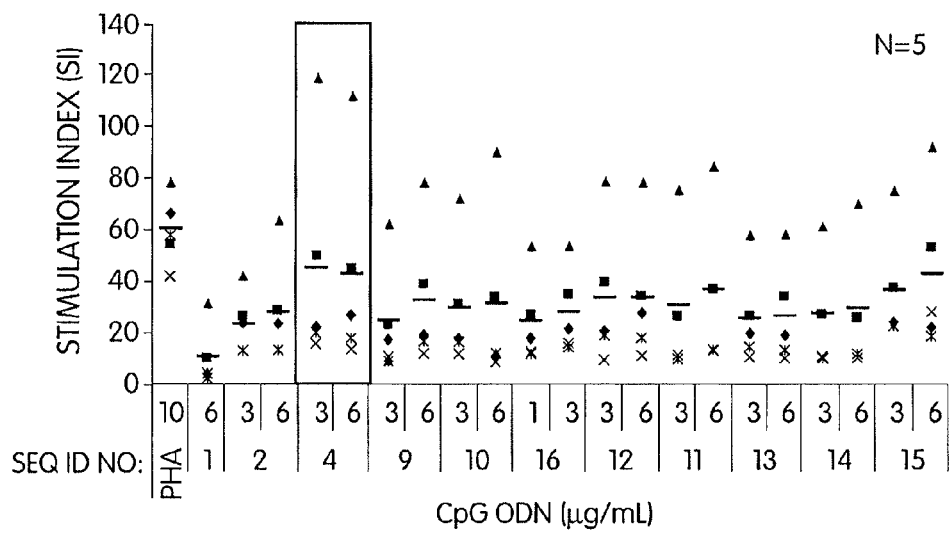
FIG. 9 shows the effect of semi-soft C-class CpG on B cell proliferation. PBMCs from 5 HCV-infected subjects were incubated with A, B, C and semi-soft-C class CpG for 5 days. Cells were then pulsed with $^3$H-thymidine for 16 to 18 hours before measuring radioactivity. Values are represented as stimulation indices in comparison with media control (SI=cpm incubated with CpG/cpm of cells incubated with media alone).

The effect of CpG on B cell stimulation was also investigated. As shown in FIGS. 8 and 9, CpG Class A was a poor stimulator of B cells for both HCV-infected and normal populations. In contrast, classes B, C and semi-soft C CpG strongly activated B cells. There were no differences between PBMCs from normal and HCV-infected subjects.

IL-10 Secretion from PBMC after Stimulation with CpG ODN

Figure 10:
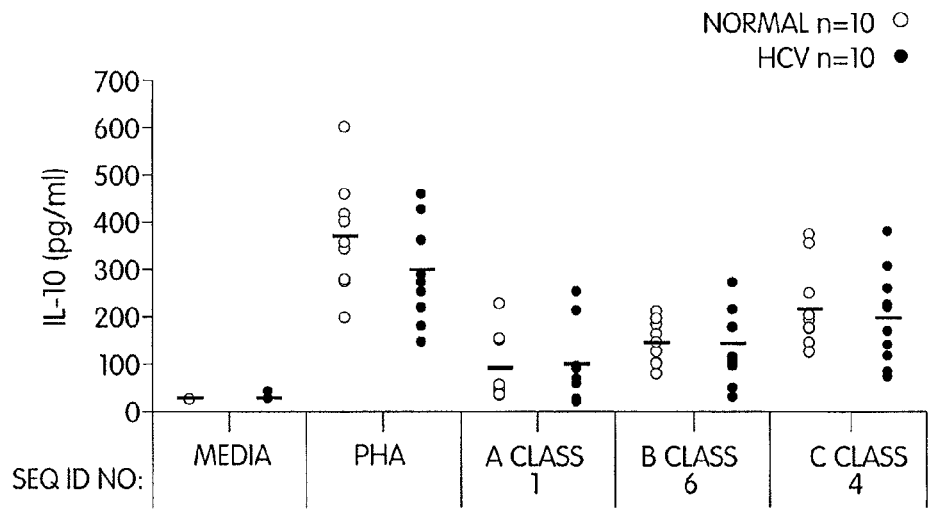
FIG. 10 shows the IL-10 secretion following stimulation with three classes of CpG. PBMCs from normal or HCV-infected subjects were incubated with different classes of CpG for 48 h. Cell supernatants were collected and assayed for IL-10 secretion by commercial ELISA kits. The average IL-10 secretion for 10 normal subjects and 10 HCV-infected subjects are shown by the black bars.

The production of cytokine IL-10 following stimulation with CpG was also assessed and these results are shown in FIG. 10. For both HCV-infected and normal subjects, all classes of CpG induced significant secretion of IL-10, and there were no differences between PBMC from normal volunteers and those from HCV chronic carriers. Several cell types can produce IL-10 after incubation with CpG; however since B cells are the major producers of this cytokine, IL-10 production can be used as an indicator of the level of B cell activation.

Effects of Intron A and Ribavirin

Figure 11:
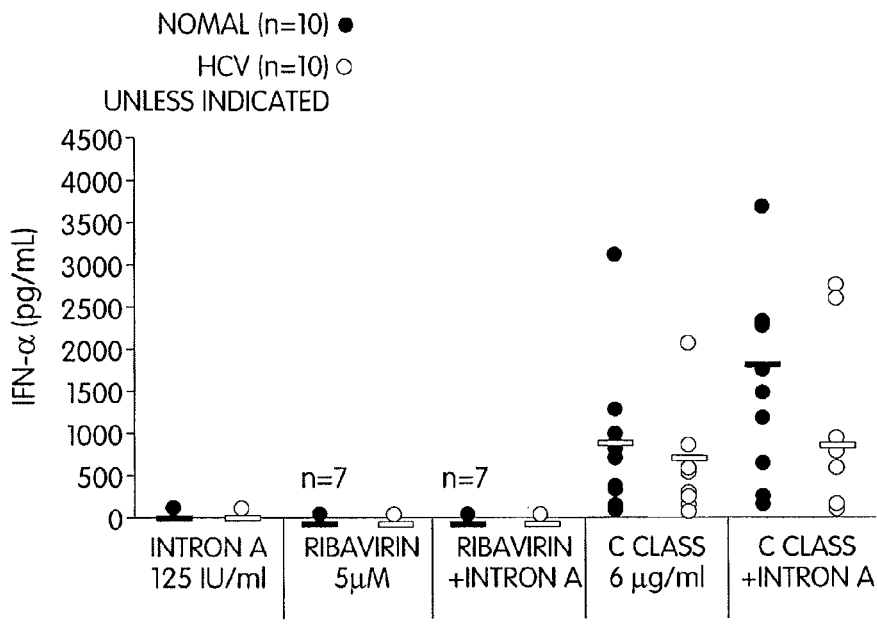
FIG. 11 shows IFN-α secretion following stimulation of HCV-infected cells with Ribavirin and CpG alone or in combination with Intron A. PBMCs from 10 HCV-infected subjects and 10 normal healthy donors were incubated with Intron A, Ribavirin or C-class CpG alone and also with and without Intron A (a purified exogenous source of IFN-α) for 48 hours. Cell supernatants were collected and assayed for IFN-α secretion by commercial ELISA kits. The amount of IFN-α measured for Intron A alone for each subject, was considered background and was subtracted from Intron A, Ribavirin+Intron A and C-Class+Intron A for these same subjects before the data was included in the graph. Mean values for normal and HCV subjects are indicated by black and white bars respectively.

The in vitro effect of Ribavirin and exogenous IFN-α, Intron A, alone or in combination with CpG was tested on HCV-infected cells. Neither Ribavirin nor Intron A, on their own or together, resulted in the induction of IFN-α secretion by HCV-infected PBMCs (FIG. 11).

Figure 12:
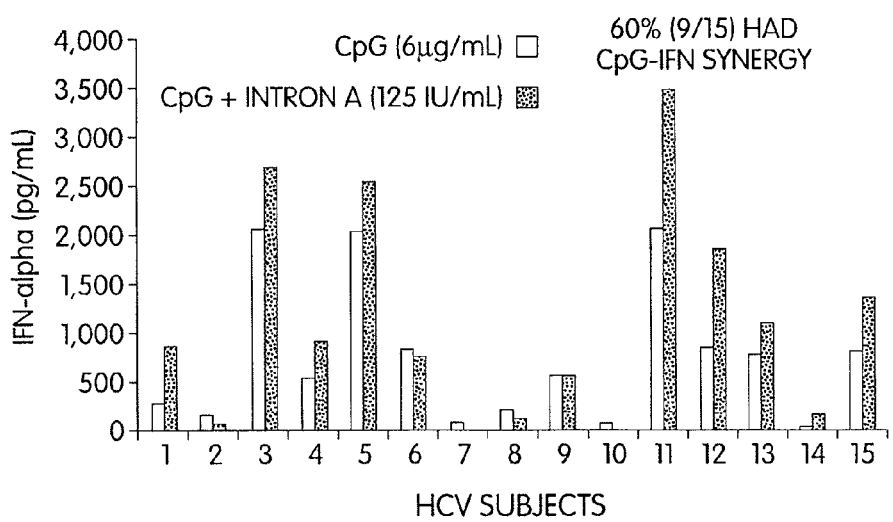
FIG. 12. Synergistic effect of CpG combined with Intron A on IFN-α secretion by HCV-infected cells. PBMCs from 15 HCV-infected subjects were incubated with C-class CpG alone or together with Intron A (a purified exogenous source of IFN-α) for 48 hours. Cell supernatants were collected and assayed for IFN-α secretion by commercial ELISA kits. The amount of IFN-α measured for Intron A alone for each subject, was subtracted from CpG+Intron A for these same subjects before the data was included in the graph.

As has been discussed above, A and C class CpG ODN result in strong induction of IFN-α secretion from pDC from normal and HCV-infected subjects. Furthermore, when CpG and Intron-A were used together, there was a synergistic response for the majority (60%) of subjects (FIG. 12).

Discussion

CpG ODN are able to induce DC from patients chronically infected with HCV, to secrete IFN-α, with higher levels using Class A and C CpG and lower levels with Class B CpG ODN. The levels of secreted IFN-α are comparable to those observed with cells from normal healthy volunteers. As well, IP-10 is induced from stimulated HCV PBMC, further indicating a Th1-type immune activation.

HCV antigen-specific immune responses are already present in persons chronically infected with HCV. These are Th2-biased and thus cannot bring about clearance of the HCV-infected cells. Th1 type responses would be required for viral clearance. Augmentation of systemic levels of Th1 cytokines, without additional antigen, allows persons chronically infected with HCV to develop Th1-type HCV-specific immune responses that are instrumental in viral clearance. All classes of CpG (A, B and C) are capable of establishing Th1-type responses. These Th1-type responses are essential for long-term clearance of HCV chronic infection, yet they are difficult to induce with exogenous IFN-α therapy, which has direct anti-viral effects but not direct effects on the immune system. CpG ODN can therefore be used in combination with exogenous IFN-α to treat HCV chronic carriers.

Alternatively, CpG ODN could also be used alone. Owing to induction of cytokines such as IFN-α and IFN-γ, CpG ODN on its own has direct anti-viral effects, in addition to the induction of Th1-type HCV-specific immune responses. In some instances, the A and C class molecules are preferred since they induce higher levels of IFNs. Depending on their characteristic sequence, CpG ODN can preferentially stimulate pDC functions, maturation and type I IFN production (Krug, A et al., Eur J Immunol, 2001; 31:2154-2163). Although according to the invention two classes of CpG ODN were shown to be superior at stimulating IFN-α production, any CpG ODN, regardless of backbone or CpG sequence, could be used in the treatment of chronic HCV. The controlled release of different type I IFN isoforms by specific CpG ODN in vivo is superior to the systemic administration of recombinant type I IFN that is of a single subtype (e.g., Intron A is only IFN-α2b). Soft and semi-soft versions of CpG ODN are capable of stimulating similar levels of IFN-α as their parent molecule. Soft or semi-soft versions of the CpG ODN, especially the C class, would preferentially be used for chronic treatment of HCV, as they are more easily degraded and would therefore not be expected to accumulate in the organs, specifically the liver, spleen and kidney.

At least 50% of the HCV subjects failed to respond to exogenous IFN-α therapy, however CpG ODN (especially A and C class) were able to induce IFN-α secretion in vitro at levels comparable to normal healthy volunteers in all subjects. CpG ODN could therefore be used to treat patients who have failed to respond to exogenous IFN-α therapy, whether the IFN is pegylated or not, and whether the treatment also includes Ribavirin or not. Classes of CpG ODN that induce high levels of IFN-α would be preferred, and ever more preferred for long-term treatment would be the semi-soft versions.

Neither commercial Intron-A (IFN-α-2b) nor Ribavirin, alone or in combination, were capable of inducing IFN-α secretion from PBMCs from normal or HCV infected subjects in vitro. However when CpG ODN was used in combination with Intron-A, a synergistic effect was observed for IFN-α secretion from PBMCs from HCV infected subjects. The C class of ODN were shown to have synergy with exogenous IFN-α; however treatment with any class of CpG ODN with commercial alpha-interferons would be therapeutically effective. As mentioned previously, due to their relative ease of degradation into non-stimulatory metabolites, semi-soft versions of the CpG ODN could be used for chronic treatment without fear of accumulation in end-organs such as the kidney.

Ribavirin is purported to have Th1 effects, but in these studies it had no immunostimulatory activity on human PBMCs. Even in combination with Intron A, Ribavirin did not enhance endogenous IFN-α production. Thus, replacing Ribavirin in combination therapy for HCV with a CpG. ODN will increase the proportion of sustained viral responses. When combined with CpG ODN, Ribavirin reduced the efficacy of CpG. CpG ODN should therefore be given in combination with alpha-interferons in the absence of Ribavirin.

CpG ODN have been administered IM, SC and IV to human subjects and were determined to be well tolerated and safe (clinical study, in progress). Any effective route of administration would be acceptable such as SC, IM, IV, inhalation etc. however subcutaneous administration would be the route of choice. CpG ODN were diluted in TE buffer and added to PBMCs however, CpG ODN could also be formulated in delivery systems such as bioadhesive polymers (Sha et al., 1999), cochleates (Gould-Fogerite et al., 1994, 1996), dendrimers (Kukowska-Latallo et al., 1996, Qin et al, 1998), enteric-coated capsules (Czerkinsky et al., 1987, Levine et al., 1987), emulsomes (Vancott et al., 1998, Lowell et al., 1997), ISCOMs (Mowat et al., 1993, Morein et al., 1999, Hu et al., 1998, Carlsson et al., 1991), liposomes (Childers et al., 1999, Michalek et al., 1989, 1992), microspheres (Gupta et al., 1998, Maloy et al., 1994, Eldridge et al., 1989), nanospheres (Roy et al., 1999), polymer rings (Wyatt et al., 1998), proteosomes (Lowell et al., 1988, 1996) and virosomes (Gluck et al., 1992, Mengiardi et al., 1995, Cryz et al., 1998).

For treatment of HCV chronic carriers, CpG ODN could be administered on a repeated basis from once daily to once monthly, but preferably every 3-10 days, and most preferably weekly, for a prolonged period. This period could be from one month to two years, but preferably 3 to 12 months, and most preferably for 6 months. Thus the most optimal therapy would be given twice weekly or weekly for 6 months. It could also be given more frequently during an inductive phase (daily or every other day or twice weekly or weekly for the first 1-3 months), then less frequently for maintenance (weekly, or every other week, or monthly for several more months).

For combination therapy, CpG and alpha-interferons (pegylated or not) could potentially be (i) mixed together and given at the same time and by the same route (subcutaneous), (ii) given at the same time and same route but not mixed, (iii) given at the same time but by different routes (e.g., the alpha-interferon could be given SC and the CpG could be IV, IM, ID, orally or topically), (iv) given at different times and schedules with same or different routes, or (v) given consecutively. In this latter case, preferably the IFN-α would be given first in order to reduce viral load, then the CpG ODN would be given afterwards to induce and sustain Th1-type adaptive immunity for long term control.

REFERENCES

1. Choo, Q. L., G. Kuo, A. J. Weiner, L. R. Overby, D. W. Bradley, M. Houghton. 1989. Isolation of a cDNA clone derived from a blood-borne non-A, non-B viral hepatitis genome. Science. 244: 359-62.
2. Choo, Q. L., K. H. Richman, J. H. Han, K. Berger, C. Lee, C. Dong, C. Gallegos, D. Coit, R. Medina-Selby, P. J. Barr, et al. 1991. Genetic organization and diversity of the hepatitis C virus. Proc Natl Acad Sci USA. 88: 2451-5.
3. van der Poel, C. L., H. T. Cuypers, H. W. Reesink. 1994. Hepatitis C virus six years on. Lancet. 344: 1475-9.
4. van der Poel, C. L. 1994. Hepatitis C virus. Epidemiology, transmission and prevention. Curr Stud Hematol Blood Transfus: 137-63.
5. Kiyosawa, K., T. Sodeyama, E. Tanaka, Y. Gibo, K. Yoshizawa, Y. Nakano, S. Furuta, Y. Akahane, K. Nishioka, R. H. Purcell, et al. 1990. Interrelationship of blood transfusion, non-A, non-B hepatitis and hepatocellular carcinoma: analysis by detection of antibody to hepatitis C virus. Hepatology. 12: 671-5.
6. Alter, M. J., H. S. Margolis, K. Krawczynski, F. N. Judson, A. Mares, W. J. Alexander, P. Y. Hu, J. K. Miller, M. A. Gerber, R. E. Sampliner, et al. 1992. The natural history of community-acquired hepatitis C in the United States. The Sentinel Counties Chronic non-A, non-B Hepatitis Study Team. N Engl J Med. 327: 1899-905.
7. Alter, M. J. 1994. Transmission of hepatitis C virus—route, dose, and titer. N Engl J Med. 330: 784-6.
8. Alter, M. J. 1994. Review of serologic testing for hepatitis C virus infection and risk of posttransfusion hepatitis C. Arch Pathol Lab Med. 118: 342-5.
9. Alter, M. J., E. E. Mast. 1994. The epidemiology of viral hepatitis in the United States. Gastroenterol Clin North Am. 23: 437-55.
10. Weiner, A. J., H. M. Geysen, C. Christopherson, J. E. Hall, T. J. Mason, G. Saracco, F. Bonino, K. Crawford, C. D. Marion, K. A. Crawford, et al. 1992. Evidence for immune selection of hepatitis C virus (HCV) putative envelope glycoprotein variants: potential role in chronic HCV infections. Proc Natl Acad Sci U S A. 89: 3468-72.
11. Kato, N., Y. Ootsuyama, H. Sekiya, S. Ohkoshi, T. Nakazawa, M. Hijikata, K. Shimotohno. 1994. Genetic drift in hypervariable region 1 of the viral genome in persistent hepatitis C virus infection. J Virol. 68: 4776-84.
12. Diepolder, H. M., R. Zachoval, R. M. Hoffmann, E. A. Wierenga, T. Santantonio, M. C. Jung, D. Eichenlaub, G. R. Pape. 1995. Possible mechanism involving T-lymphocyte response to non-structural protein 3 in viral clearance in acute hepatitis C virus infection. Lancet. 346: 1006-7.
13. Missale, G., R. Bertoni, V. Lamonaca, A. Valli, M. Massari, C. Mori, M. G. Rumi, M. Houghton, F. Fiaccadori, C. Ferrari. 1996. Different clinical behaviors of acute hepatitis C virus infection are associated with different vigor of the anti-viral cell-mediated immune response. J Clin Invest. 98: 706-14.
14. Tsai, S. L., Y. F. Liaw, M. H. Chen, C. Y. Huang, G. C. Kuo. 1997. Detection of type 2-like T-helper cells in hepatitis C virus infection: implications for hepatitis C virus chronicity. Hepatology. 25: 449-58.
15. Rehermann, B., K. M. Chang, J. G. McHutchison, R. Kokka, M. Houghton, F. V. Chisari. 1996. Quantitative analysis of the peripheral blood cytotoxic T lymphocyte response in patients with chronic hepatitis C virus infection. Journal of Clinical Investigation. 98: 1432-1440
16. Erickson, A. L., M. Houghton, Q. L. Choo, A. J. Weiner, R. Ralston, E. Muchmore, C. M. Walker. 1993. Hepatitis C virus-specific CTL responses in the liver of chimpanzees with acute and chronic hepatitis C. J Immunol. 151: 4189-99.
17. Chen, M., M. Sallberg, A. Sonnerborg, O. Weiland, L. Mattsson, L. Jin, A. Birkett, D. Peterson, D. R. Milich. 1999. Limited humoral immunity in hepatitis C virus infection. Gastroenterology. 116: 135-43.
18. Nagler, A., L. L. Lanier, J. H. Phillips. 1988. The effects of IL-4 on human natural killer cells. A potent regulator of IL-2 activation and proliferation. J Immunol. 141: 2349-51.
19. Martinez, O. M., R. S. Gibbons, M. R. Garovoy, F. R. Aronson. 1990. IL-4 inhibits IL-2 receptor expression and IL-2-dependent proliferation of human T-cells. J Immunol. 144:2211-5.
20. Moore, K. W., O. G. A, R. de Waal Malefyt, P. Vieira, T. R. Mosmann. 1993. Interleukin-10. Annu Rev Immunol. 11: 165-90.
21. de Waal Malefyt, R., J. Haanen, H. Spits, M. G. Roncarolo, A. te Velde, C. Figdor, K. Johnson, R. Kastelein, H. Yssel, J. E. de Vries. 1991. Interleukin 10 (IL-10) and viral IL-10 strongly reduce antigen-specific human T-cell proliferation by diminishing the antigen-presenting capacity of monocytes via downregulation of class II major histocompatibility complex expression. J Exp Med. 174: 915-24.
22. Fiorentino, D. F., A. Zlotnik, P. Vieira, T. R. Mosmann, M. Howard, K. W. Moore, O. G. A. 1991. IL-10 acts on the antigen-presenting cell to inhibit cytokine production by Th1 cells. J Immunol. 146: 3444-51.
23. Schlaak, J. F., T. Pitz, H. F. Lohr, K. H. Meyer zum Buschenfelde, G. Gerken. 1998. Interleukin 12 enhances deficient HCV-antigen-induced Th1-type immune response of peripheral blood mononuclear cells. J Med Virol. 56: 112-7.
24. Cacciarelli, T. V., O. M. Martinez, R. G. Gish, J. C. Villanueva, S. M. Krams. 1996. Immunoregulatory cytokines in chronic hepatitis C virus infection: pre- and post-treatment with interferon alfa. Hepatology. 24: 6-9.
25. Kuzushita, N., N. Hayashi, K. Katayama, T. Kamada. 1995. [Histological features and HLA-DNA types in HCV carriers with persistently normal ALT levels]. Nippon Rinsho. 53: 576-81.
26. Kanto, T., N. Hayashi, T. Takehara, T. Tatsumi, N. Kuzushita, A. Ito, Y. Sasaki, A. Kasahara, M. Hori. 1999.

Impaired allostimulatory capacity of peripheral blood dendritic cells recovered from hepatitis C virus-infected individuals. J Immunol. 162: 5584-91.
27. Bain, C., A. Fatmi, F. Zoulim, J. P. Zarski, C. Trepo, G. Inchauspe. 2001. Impaired allostimulatory function of dendritic cells in chronic hepatitis C infection. Gastroenterology. 120: 512-24.
28. Sansonno, D., C. Lotesoriere, V. Comacchiulo, M. Fanelli, P. Gatti, G. Iodice, V. Racanelli, F. Dammacco. 1998. Hepatitis C virus infection involves CD34(+) hematopoietic progenitor cells in hepatitis C virus chronic carriers. Blood. 92: 3328-37.
29. Auffermann-Gretzinger, S., E. B. Keeffe, S. Levy. 2001. Impaired dendritic cell maturation in patients with chronic, but not resolved, hepatitis C virus infection. Blood. 97: 3171-6.
30. Kruse, M., O. Rosorius, F. Kratzer, G. Stelz, C. Kuhnt, G. Schuler, J. Hauber, A. Steinkasserer. 2000. Mature dendritic cells infected with herpes simplex virus type 1 exhibit inhibited T-cell stimulatory capacity. J Virol. 74: 7127-36.
31. Fugier-Vivier, I., C. Servet-Delprat, P. Rivailler, M. C. Rissoan, Y. J. Liu, C. Rabourdin-Combe. 1997. Measles virus suppresses cell-mediated immunity by interfering with the survival and functions of dendritic and T-cells. J Exp Med. 186: 813-23.
32. Sarobe et. al. 2002, Journal of Virology 76:10, 5062-5070 Chisari, F. V., C. Ferrari. 1995. Hepatitis B virus immunopathogenesis. Annu Rev Immunol. 13: 29-60
33. Chisari, F. V. 1997. Cytotoxic T-cells and viral hepatitis. Journal of Clinical Investigation. 99: 1472-1477
34. Marianneau, P., A. M. Steffan, C. Royer, M. T. Drouet, D. Jaeck, A. Kirn, V. Deubel. 1999. Infection of primary cultures of human Kupffer cells by Dengue virus: no viral progeny synthesis, but cytokine production is evident. J Virol. 73: 5201-6.
35. Krieg, A. M., A. K. Yi, S. Matson, T. J. Waldschmidt, G. A. Bishop, R. Teasdale, G. A. Koretzky, D. M. Klinman. 1995. CpG motifs in bacterial DNA trigger direct B-cell activation. Nature. 374: 546-9
36. Yi, A. K., P. Hornbeck, D. E. Lafrenz, A. M. Krieg. 1996. CpG DNA rescue of murine B lymphoma cells from anti-IgM-induced growth arrest and programmed cell death is associated with increased expression of c-myc and bcl-xL. J Immunol. 157: 4918-4925
37. Yi, A. K., J. H. Chace, J. S. Cowdery, A. M. Krieg. 1996. IFN-gamma promotes IL-6 and IgM secretion in response to CpG motifs in bacterial DNA and oligodeoxynucleotides. Journal of Immunology. 156: 558-64
38. Klinman, D. M., A. K. Yi, S. L. Beaucage, J. Conover, A. M. Krieg. 1996. CpG motifs present in bacteria DNA rapidly induce lymphocytes to secrete interleukin 6, interleukin 12, and interferon gamma. Proc Natl Acad Sci USA. 93: 2879-2883
39. Klinman, D. M., D. Verthelyi, F. Takeshita, K. J. Ishii. 1999. Immune recognition of foreign DNA: a cure for bioterrorism? Immunity. 11: 123-9
40. Halpern, M. D., R. J. Kurlander, D. S. Pisetsky. 1996. Bacterial DNA induces murine interferon-gamma production by stimulation of interleukin-12 and tumor necrosis factor-alpha. Cell Immunol. 167: 72-8
41. Cowdery, J. S., J. H. Chace, A. K. Yi, A. M. Krieg. 1996. Bacterial DNA induces NK cells to produce IFN-gamma in vivo and increases the toxicity of lipopolysaccharides. J Immunol. 156: 4570-4575
42. Schwartz, D. A., T. J. Quinn, P. S. Thorne, S. Sayeed, A. K. Yi, A. M. Krieg. 1997. CpG motifs in bacterial DNA cause inflammation in the lower respiratory tract. Journal of Clinical Investigation. 100: 68-73
43. Yamamoto, S., T. Yamamoto, T. Kataoka, E. Kuramoto, O. Yano, T. Tokunaga. 1992. Unique palindromic sequences in synthetic oligonucleotides are required to induce IFN [correction of INF] and augment IFN-mediated natural killer activity. J Immunol. 148: 4072-6.
44. Ballas, Z. K., W. L. Rasmussen, A. M. Krieg. 1996. Induction of NK activity in murine and human cells by CpG motifs in oligodeoxynucleotides and bacterial DNA. J Immunol. 157: 1840-1845
45. Chace, J. H., N. A. Hooker, K. L. Mildenstein, A. M. Krieg, J. S. Cowdery. 1997. Bacterial DNA-induced NK cell IFN-gamma production is dependent on macrophage secretion of IL-12. Clinical Immunology & Immunopathology. 84: 185-93
46. Roman, M., E. Martin-Orozco, J. S. Goodman, M. D. Nguyen, Y. Sato, A. Ronaghy, R. S. Kornbluth, D. D. Richman, D. A. Carson, E. Raz. 1997. Immunostimulatory DNA sequences function as T helper-1-promoting adjuvants [see comments]. Nat Med. 3: 849-54
47. Krieg, A. M., S. Matson, K. Cheng, E. Fisher, G. A. Koretzky, J. G. Koland. 1997. Identification of an oligodeoxynucleotide sequence motif that specifically inhibits phosphorylation by protein tyrosine kinases. Antisense and Nucleic Acid Drug Development. 7: 115-23
48. Davis, H. L., R. Weeranta, T. J. Waldschmidt, L. Tygrett, J. Schorr, A. M. Krieg. 1998. CpG DNA is a potent enhancer of specific immunity in mice immunized with recombinant hepatitis B surface antigen. Journal of Immunology. 160: 870-6
49. Moldoveanu, Z., L. Love-Homan, W. Q. Huang, A. M. Krieg. 1998. CpG DNA, a novel immune enhancer for systemic and mucosal immunization with influenza virus. Vaccine. 16: 1216-24
50. Chu, R. S., O. S. Targoni, A. M. Krieg, P. V. Lehmann, C. V. Harding. 1997. CpG oligodeoxynucleotides act as adjuvants that switch on T helper 1 (Th1) immunity. Journal of Experimental Medicine. 186: 1623-31
51. Lipford, G. B., M. Bauer, C. Blank, R. Reiter, H. Wagner, K. Heeg. 1997. CpG-containing synthetic oligonucleotides promote B and cytotoxic T-cell responses to protein antigen: a new class of vaccine adjuvants. Eur J Immunol. 27: 2340-4
52. Weiner, G. J., H. M. Liu, J. E. Wooldridge, C. E. Dahle, A. M. Krieg. 1997. Immunostimulatory oligodeoxynucleotides containing the CpG motif are effective as immune adjuvants in tumor antigen immunization. Proceedings of the National Academy of Sciences of the United States of America. 94: 10833-7
53. Kline, J. N., T. J. Waldschmidt, T. R. Businga, J. E. Lemish, J. V. Weinstock, P. S. Thorne, A. M. Krieg. 1998. Modulation of airway inflammation by CpG oligodeoxynucleotides in a murine model of asthma. J Immunol. 160: 2555-9
54. Krieg, A. M. 2001. Now I know my CpGs. Trends Microbiol. 9: 249-52.
55. Krieg, A. M., L. Love-Homan, A. K. Yi, J. T. Harty. 1998. CpG DNA induces sustained IL-12 expression in vivo and resistance to *Listeria monocytogenes* challenge. J Immunol. 161: 2428-34
56. Walker, P. S., T. Scharton-Kersten, A. M. Krieg, L. Love-Homan, E. D. Rowton, M. C. Udey, J. C. Vogel. 1999. Immunostimulatory oligodeoxynucleotides promote protective immunity and provide systemic therapy for leishmaniasis via IL-12- and IFN-gamma-dependent mechanisms. Proc Natl Acad Sci U S A. 96: 6970-5

57. Gramzinski, R. A., D. L. Doolan, M. Sedegah, H. L. Davis, A. M. Krieg, S. L. Hoffman. 2001. Interleukin-12- and gamma interferon-dependent protection against malaria conferred by CpG oligodeoxynucleotide in mice. Infect Immun. 69: 1643-9.
58. Roffi, L., G. C. Mels, G. Antonelli, G. Bellati, F. Panizzuti, A. Piperno, M. Pozzi, D. Ravizza, G. Angeli, F. Dianzani, et al. 1995. Breakthrough during recombinant interferon alfa therapy in patients with chronic hepatitis C virus infection: prevalence, etiology, and management. Hepatology. 21: 645-9.
59. Imai, Y., S. Kawata, S. Tamura, I. Yabuuchi, S. Noda, M. Inada, Y. Maeda, Y. Shirai, T. Fukuzaki, I. Kaji, H. Ishikawa, Y. Matsuda, M. Nishikawa, K. Seki, Y. Matsuzawa. 1998. Relation of interferon therapy and hepatocellular carcinoma in patients with chronic hepatitis C. Osaka Hepatocellular Carcinoma Prevention Study Group. Ann Intern Med. 129: 94-9.
60. Davis H L C C, Morris M L, Efler S M, Cameron D W, Heathcote J. 2000. CpG ODN is safe and highly effective in humans as adjuvant to HBV vaccine: Preliminary results of Phase I trial with CpG ODN SEQ ID NO. 2. Presented at The Third Annual Conference on Vaccine Research. S25: 47.

EQUIVALENTS

It will be understood that various modifications may be made to the embodiments disclosed herein. Therefore, the above description should not be construed as limiting, but merely as exemplifications of preferred embodiments. Those skilled in the art will envision other modifications within the scope of the claims appended hereto.

All references, patents and patent applications disclosed herein are incorporated by reference in their entirety.

We claim:

1. A method of controlling viral replication and viral spread in a human subject having an HCV infection that was not successfully treated using a previous non-CpG therapy comprising
administering to a subject in need thereof an antiviral agent and a C class CpG immunostimulatory nucleic acid having a semi-soft backbone and comprising
a sequence of

5' $X_1DCGHX_2$ 3' wherein C is unmethylated, $X_1$ and $X_2$ are any nucleic acid sequence 0-10 nucleotides long, D is a nucleotide other than C, and H is a nucleotide other than G, and
a sequence of

5' CGG 3', wherein the nucleic acid is 8 to 100 nucleotides in length, in an amount effective to control viral replication and viral spread of HCV.

* * * * *

SEQUENCE LISTING

```
<160> NUMBER OF SEQ ID NOS: 32

<210> SEQ ID NO 1
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 1
ggggacgacg tcgtgggggg g                                                    21

<210> SEQ ID NO 2
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 2
tcgtcgtttt gtcgttttgt cgtt                                                 24

<210> SEQ ID NO 3
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 3
tgctgctttt tgctggcttt tt                                                   22

<210> SEQ ID NO 4
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 4
tcgtcgtttt cggcggccgc cg                                                   22

<210> SEQ ID NO 5
<211> LENGTH: 24
<212> TYPE: DNA
<213> ORGANISM: Artificial sequence
```

-continued

<220> FEATURE:
<223> OTHER INFORMATION: Synthetic Oligonucleotide

<400> SEQUENCE: 5
tcgtcgtttc gtcgttttgt cgtt                                    24

<210> SEQ ID NO 6
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 6
tcgtcgtttt tcgtgcgttt tt                                      22

<210> SEQ ID NO 7
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 7
tcgtcgtttt cggcggccgc cg                                      22

<210> SEQ ID NO 8
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 8
tcgtcgtttt gtcgttttgt cgtt                                    24

<210> SEQ ID NO 9
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 9
tcgtcgtttt cggcggccgc cg                                      22

<210> SEQ ID NO 10
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 10
tcgtcgtttt cggcggccgc cg                                      22

<210> SEQ ID NO 11
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 11
tcgtcgtttt cggcgcgcgc cg                                      22

```
<210> SEQ ID NO 12
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 12
tcgtcgtttt cggcgcgcgc cg                                            22

<210> SEQ ID NO 13
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 13
tcgtcgtttt acggcgccgt gccg                                          24

<210> SEQ ID NO 14
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 14
tcgtcgtttt acggcgccgt gccg                                          24

<210> SEQ ID NO 15
<211> LENGTH: 24
<212> TYPE: DNA
<213> ORGANISM: Artificial sequence
<220> FEATURE:
<223> OTHER INFORMATION: Synthetic Oligonucleotide

<400> SEQUENCE: 15
tcgtcgtttt acggcgccgt gccg                                          24

<210> SEQ ID NO 16
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 16
tcgtcgtttt cggcggccgc cg                                            22

<210> SEQ ID NO 17
<211> LENGTH: 22
<212> TYPE: DNA
<213> ORGANISM: Artificial sequence
<220> FEATURE:
<223> OTHER INFORMATION: Synthetic Oligonucleotide

<400> SEQUENCE: 17
tcgcgtcgtt cggcgcgcgc cg                                            22

<210> SEQ ID NO 18
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 18
```

-continued tcgtcgacgt tcggcgcgcg ccg    23

<210> SEQ ID NO 19
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 19
tcggacgttc ggcgcgcgcc g    21

<210> SEQ ID NO 20
<211> LENGTH: 19
<212> TYPE: DNA
<213> ORGANISM: Artificial sequence
<220> FEATURE:
<223> OTHER INFORMATION: Synthetic Oligonucleotide

<400> SEQUENCE: 20
tcggacgttc ggcgcgccg    19

<210> SEQ ID NO 21
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 21
tcgcgtcgtt cggcgcgccg    20

<210> SEQ ID NO 22
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 22
tcgacgttcg gcgcgcgccg    20

<210> SEQ ID NO 23
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 23
tcgacgttcg gcgcgccg    18

<210> SEQ ID NO 24
<211> LENGTH: 18
<212> TYPE: DNA
<213> ORGANISM: Artificial sequence
<220> FEATURE:
<223> OTHER INFORMATION: Synthetic Oligonucleotide

<400> SEQUENCE: 24
tcgcgtcgtt cggcgccg    18

<210> SEQ ID NO 25
<211> LENGTH: 22
<212> TYPE: DNA
<213> ORGANISM: Artificial sequence

```
<220> FEATURE:
<223> OTHER INFORMATION: Synthetic Oligonucleotide

<400> SEQUENCE: 25
tcgcgacgtt cggcgcgcgc cg                                              22

<210> SEQ ID NO 26
<211> LENGTH: 10
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(6)
<223> OTHER INFORMATION: n is selected from GpT, GpG, GpA, or ApA
<220> FEATURE:
<221> NAME/KEY: misc_feature
<222> LOCATION: (9)..(10)
<223> OTHER INFORMATION: n is selected from TpT, CpT, or TpC

<400> SEQUENCE: 26 tcntnncgnn                                                            10

<210> SEQ ID NO 27
<211> LENGTH: 12
<212> TYPE: DNA
<213> ORGANISM: Artificial sequence
<220> FEATURE:
<223> OTHER INFORMATION: Synthetic Oligonucleotide

<400> SEQUENCE: 27
cgacgttcgt cg                                                         12

<210> SEQ ID NO 28
<211> LENGTH: 13
<212> TYPE: DNA
<213> ORGANISM: Artificial sequence
<220> FEATURE:
<223> OTHER INFORMATION: Synthetic Oligonucleotide

<400> SEQUENCE: 28
cggcgccgtg ccg                                                        13

<210> SEQ ID NO 29
<211> LENGTH: 12
<212> TYPE: DNA
<213> ORGANISM: Artificial sequence
<220> FEATURE:
<223> OTHER INFORMATION: Synthetic Oligonucleotide

<400> SEQUENCE: 29
ccccccgggg gg                                                         12

<210> SEQ ID NO 30
<211> LENGTH: 12
<212> TYPE: DNA
<213> ORGANISM: Artificial sequence
<220> FEATURE:
<223> OTHER INFORMATION: Synthetic Oligonucleotide

<400> SEQUENCE: 30
ggggggcccc cc                                                         12
```

```
<210> SEQ ID NO 31
<211> LENGTH: 10
<212> TYPE: DNA
<213> ORGANISM: Artificial sequence
<220> FEATURE:
<223> OTHER INFORMATION: Synthetic Oligonucleotide

<400> SEQUENCE: 31
cccccggggg                                                            10

<210> SEQ ID NO 32
<211> LENGTH: 10
<212> TYPE: DNA
<213> ORGANISM: Artificial sequence
<220> FEATURE:
<223> OTHER INFORMATION: Synthetic Oligonucleotide

<400> SEQUENCE: 32
gggggccccc                                                            10
```